US007666420B2

(12) United States Patent
Marche et al.

(10) Patent No.: US 7,666,420 B2
(45) Date of Patent: Feb. 23, 2010

(54) COMPOSITION FOR TREATING PATHOLOGY ASSOCIATED WITH MSRV/HERV-W

(75) Inventors: Patrice Marche, Meylan (FR); Alexandre Rolland, Sassenage (FR); Evelyne Jouvin-Marche, Meylan (FR); Herve Perron, Saint Genis les Ollieres (FR)

(73) Assignees: Biomerieux, Marcy l'Etoile (FR); Institut National de la Sante et de la Recherche Medicale, Paris (FR)

( * ) Notice: Subject to any disclaimer, the term of this patent is extended or adjusted under 35 U.S.C. 154(b) by 103 days.

(21) Appl. No.: 10/586,742

(22) PCT Filed: Jan. 24, 2005

(86) PCT No.: PCT/FR2005/000156

§ 371 (c)(1),
(2), (4) Date: Sep. 26, 2006

(87) PCT Pub. No.: WO2005/080437

PCT Pub. Date: Sep. 1, 2005

(65) Prior Publication Data

US 2008/0038279 A1     Feb. 14, 2008

(30) Foreign Application Priority Data

Jan. 23, 2004    (FR) .................................. 04 00675

(51) Int. Cl.
| | |
|---|---|
| A61K 39/395 | (2006.01) |
| A61K 39/42 | (2006.01) |
| C07K 16/00 | (2006.01) |
| C07K 16/08 | (2006.01) |
| C12P 21/08 | (2006.01) |

(52) U.S. Cl. .............. 424/147.1; 424/130.1; 424/139.1; 424/141.1; 424/159.1; 530/387.1; 530/387.9; 530/388.1; 530/388.3; 530/389.4

(58) Field of Classification Search ........................ None
See application file for complete search history.

(56) References Cited

FOREIGN PATENT DOCUMENTS

| WO | WO 95/21256 | 8/1995 |
|---|---|---|
| WO | WO 99/67395 | 12/1999 |
| WO | WO 01/16171 | 3/2001 |
| WO | WO 01/31021 A1 | 5/2001 |
| WO | WO 03/035110 A1 | 5/2003 |

OTHER PUBLICATIONS

Wang et al. "Involvement of CD14 and Toll-Like Receptors in Activation of Human Monocytes by *Aspergillus fumigatus* Hyphae," Infection and Immunity, vol. 69 No. 4, pp. 2402-2406 (Apr. 2001).*
Abaza et al., "Effects of amino acid substitutions outside an antigenic site on protein binding to monoclonal antibodies of predetermined specificity obtained by peptide immunization: Demonstration with region 94-100 (antigenic site 3) of myoglobin ," Journal of Protein Chemistry, vol. 11 No. 5, pp. 433-444 (Oct. 1992).*
Antony et al., "Comparative Expression of Human Endogenous Retrovirus-W Genes in Multiple Sclerosis," AIDS Research and Human Retroviruses, vol. 23 No. 10, pp. 1251-1256 (2007).*
Antony et al., "The human endogenous retrovirus envelope glycoprotein, syncytin-1, regulates neuroinflammation and its receptor expression in multiple sclerosis: a role for endoplasmic reticulum chaperones in astrocytes.," Journal of Immunology, vol. 179 No. 2, pp. 1210-1224 (Jul. 2007).*
Kim et al., "Human Endogenous Retrovirus HERV-W Family: Chromosomal Localization, Identification, and Phylogeny," AIDS Research and Human Retroviruses, vol. 17 No. 7, pp. 643-648 (2001).*
Riffkin et al., "A single amino-acid change between the antigenically different extracellular serine proteases V2 and B2 from *Dichelobacter nodosus*," Gene, vol. 167 No. 1-2, pp. 279-283 (Dec. 1995).*
Conrad, Bernard et al. "A Human Endogenous Retroviral Superantigen as Candidate Autoimmune Gene in Type 1 Diabetes," *Cell*, vol. 90, pp. 303-313, Jul. 25, 1997.
Perron, H. et al. "Molecular identification of a novel retrovirus repeatedly isolated from patients with multiple sclerosis," *Proc. National Academy of Science USA*, vol. 94, pp. 7583-7588, Jul. 1997.
Deb-Rinker, Paromita et al. "Molecular Characterization of a MSRV-like Sequence Identified by RDA from Monozygotic Twin Pairs Discordant for Schizophrenia," *Genomics*, vol. 61, pp. 133-144, 1999.
Perron, H. et al. "Isolation of a Retrovirus from Patients with Multiple Sclerosis," *The Lancet*, vol. 337, pp. 862-863, Apr. 6, 1991.
Blond, Jean-Luc et al. "Molecular Characterization and Placental Expression of HERV-W, a New Human Endogenous Retrovirus Family," *Journal of Virology*, vol. 73, No. 2, pp. 1175-1185, Feb. 1999.
Perron, Herve et al. "Particle-associated retroviral RNA and tandem RGH/HERV-W copies on human chromosome 7q: possible components of a 'chain-reaction' triggered by infectious agents in multiple sclerosis?," *Journal of NeuroVirology*, vol. 16, Supplement 2, pp. S67-S75, 2000.
Dolei, A. et al. "Multiple sclerosis-associated retrovirus (MSRV) in Sardinian MS patients," *Neurology*, vol. 58, pp. 471-473, 2002.
Garson, J. A. et al. "Detection of virion-associated MSRV-RNA in serum of patients with multiple sclerosis," *The Lancet*, vol. 351, p. 33, Jan. 3, 1998.
Olsson, Patrik et al. "Retroviral RNA Related to ERV9/MSRV in a Human Serum: A New Sequence Variant," *Aids Research and Human Retroviruses*, vol. 15, No. 6, pp. 591-593, 1999.

(Continued)

*Primary Examiner*—Zachariah Lucas
(74) *Attorney, Agent, or Firm*—Oliff & Berridge, PLC

(57) ABSTRACT

The inventive composition comprises at least one type of antibody selected in a group (i) of anti-Env-SU MSRV/HERV-W antibodies or in a group of anti-TLR4 antibodies specifically linkable with the soluble fraction of an Env protein of MSRV/HERV-W or to a TLR4 receptor of the soluble fraction of the Env protein of MSRV/HERV-W.

8 Claims, 26 Drawing Sheets

OTHER PUBLICATIONS

Figure 1:
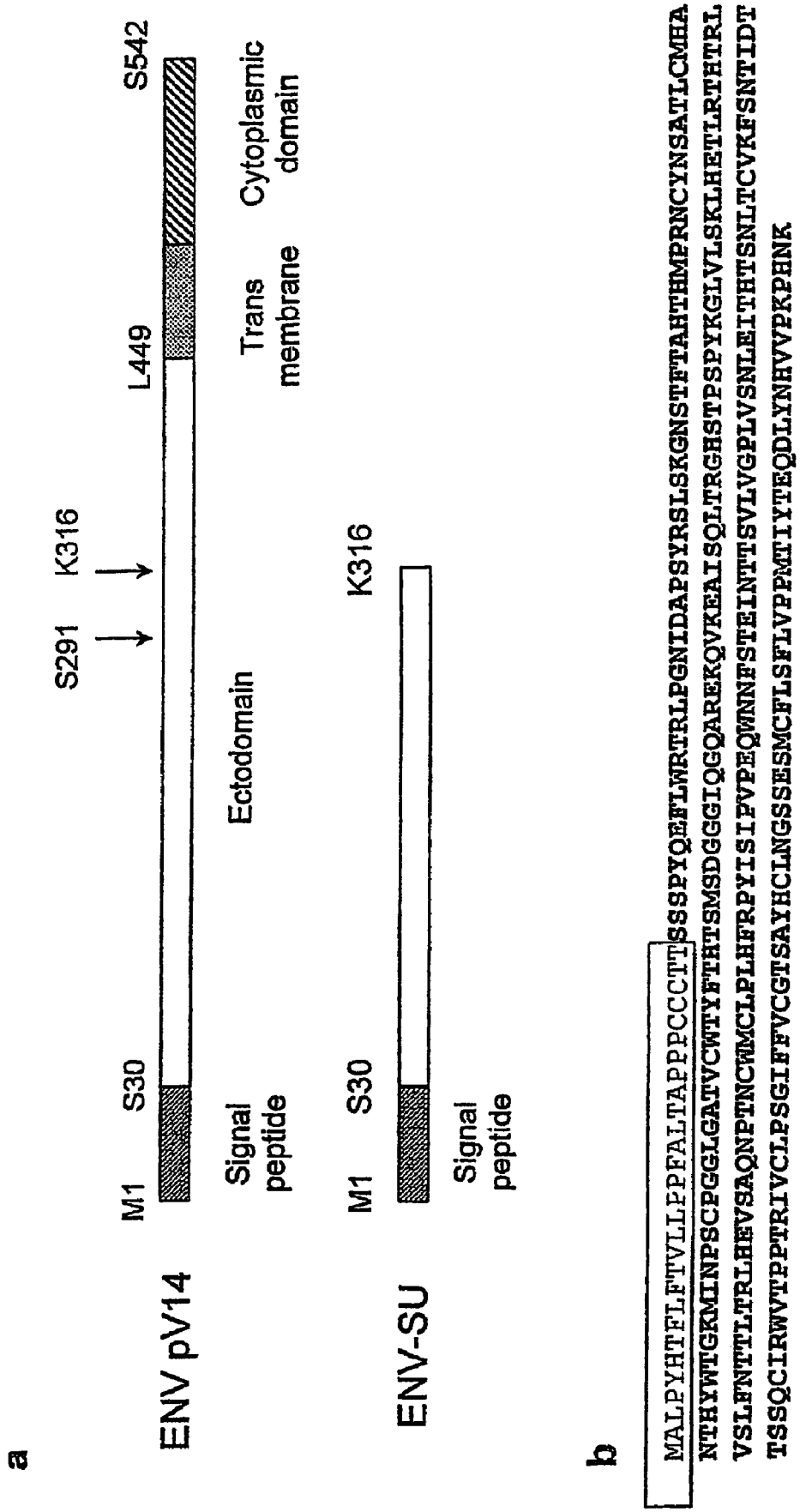

Sotgiu, S. et al. "Multiple sclerosis-associated retrovirus and MS prognosis; an observational study," *Neurology*, vol. 59, pp. 1071-1073, 2002.

Perron, H. et al. "Multiple Sclerosis Retrovirus Particles and Recombinant Envelope Trigger an Abnormal Immune Response in Vitro, by Inducing Polyclonal $V_\beta 16$ T-Lymphocyte Activation," *Virology*, vol. 287, pp. 321-332, 2001.

Firouzi, R. et al. "Multiple sclerosis-associated retrovirous particles cause T-lymphocyte-dependent death with brain hemorrhage in humanized SCID mice model," *Journal of NeuroVirology*, vol. 9, pp. 79-93, 2003.

Lin, A. et al. "The inflammatory response system in treatment-resistant schizophrenia: increased serum interleukin-6," *Schizophrenia Research*, vol. 32, pp. 9-15, 1998.

Stevens, Janice R. "Neuropathology of Schizophrenia," *Arch. Gen. Psychiatry*, vol. 39, pp. 1131-1139, Oct. 1982.

Karlsson, Hakan et al. "Retroviral RNA identified in the cerebrospinal fluids and brains of individuals with schizophrenia," *PNAS*, vol. 98, No. 8, pp. 4634-4639, Apr. 10, 2001.

Perron, H. et al. "Microbial Agents Triggering Endogenous Retroviruses within Genetic Susceptibility Loci Resulting in Expression of Superantigen and Gliotoxic Molecules: a plausible 'Immunovirogenetic' Cascade Causing Multiple Sclerosis," *Mod. Asp. Immunobiol*, vol. 1, No. 5, pp. 198-203, 2001.

Liu, Yuxin et al. "Dextromethorphan Protects Dopaminergic Neurons against Inflammation-Mediated Degeneration through Inhibition of Microglial Activation," *Journal of Pharmacology and Experimental Therapeutics*, vol. 305, pp. 212-218, 2003.

Morimoto, Kiyoshi et al. "Acute Neuroinflammation Exacerbates Excitotoxicity in Rat Hippocampus in Vivo,"*Experimental Neurology*, vol. 177, pp. 95-104, 2002.

Stoll, G. "Inflammatory cytokines in the nervous system: multifunctional mediators in autoimmunity and cerebral ischemia," *Rev. Neurol*, vol. 158, No. 10, pp. 887-891, 2002.

Guillemin, Gilles J. et al. "Implications of the kynurenine pathway and quinolinic acid in Alzheimer's disease," *Redox Report*, vol. 7, No. 4, 2002.

Kim, Eun Joo et al. "Neuroprotective Effects of Prostaglandin $E_2$ or cAMP Against Microglial and Neuronal Free Radical Mediated Toxicity Associated With Inflammation," *Journal of Neuroscience Research*, vol. 70, pp. 97-107, 2002.

Kim, Won-Gon. "Regional Difference in Susceptibility to Lipopolysaccharide-Induced Neurotoxicity in the Rat Brain: Role of Microglia," *Journal of Neuroscience*, vol. 20, pp. 6309-6316, Aug. 15, 2000.

Klein, Christine et al. "Association Studies of Parkinson's Disease and *parkin* Polymorphisms," Letters to the Editor: *Annals of Neurology*, vol. 48, No. 1, pp. 126-127, Jul. 2000.

Licinio, J. et al. "The Role of inflammatory mediators in the biology of major depression: central nervous system cytokines modulate the biological substrate of depressive symptoms, regulate stress-responsive systems, and contribute to neurotoxicity and neuroprotection," *Molecular Psychiatry*, vol. 4, pp. 317-327, 1999.

Cotter, Robin et al. "Insights into the neurodegenerative process of Alzheimer's disease: a role for mononuclear phagocyte-associated inflammation and neurotoxicity," *Journal of Luekocyte Biology*, vol. 65, pp. 416-427, Apr. 1999.

Heese, Klaus. "Inflammatory Signals Induce Neurotrophin Expression in Human Microglial Cells," *Journal of Neurochemistry*, vol. 70, No. 2, pp. 699-707, 1998.

Sasser, L. B. et al. "Subchronic Toxicity Evaluation of Lewisite in Rats," *Journal of Toxicology and Environmental Health*, vol. 47, pp. 321-334, 1996.

Chao, Chun C. "Interleukin-1 and Tumor Necrosis Factor-$\alpha$ Synergistically Mediate Neurotoxicity: Involvement of Nitric Oxide and of N-Methyl-$_D$-aspartate Receptors," *Brain, Behavior and Immunity*, vol. 9, pp. 355-365, 1995.

Chao, Chun C. et al. "Tumor Necrosis Factor-Alpha Potentiates Glutamate Neurotoxicity in Human Fetal Brain Cell Cultures," *Dev. Neurosci.*, vol. 16, pp. 172-179, 1994.

Bal-Price, Anna et al. "Inflammatory Neurodegeneration Mediated by Nitric Oxide from Activated Glia-Inhibition Neuronal Respiration, Causing Glutamate Release and Excitotoxicity," *Journal of Neuroscience*, vol. 21, No. 17, pp. 6480-6491, Sep. 2001.

Obrenovitch, T. P. "Quinolinic Acid Accumulation During Neuroinflammation," *Annals New York Academy of Sciences*, vol. 239, pp. 1-10, 2001.

Law, A. et al. "Say NO to Alzheimer's disease: the putative links between nitric oxide and dementia of the Alzheimer's type," *Brain Research Reviews*, vol. 35, pp. 73-96, 2001.

Werner, P. et al. "Glutamate excitotoxicity—a mechanism for axonal damage and oligodendrocyte death in Multiple Sclerosis?," *Journal Neural. Transm.*, vol. 60, Supplement, pp. 375-385, 2000.

Pitt, David et al. "Glutamate excitotoxicity in a model of multiple sclerosis," *Nature Medicine*, vol. 6, No. 1, pp. 67-70, Jan. 2000.

Carlson, Noel G. et al. "Inflammatory Cytokines IL-$1_\alpha$, IL-$1_\beta$, IL-6, and TFN-$\alpha$ Impart Neuroprotection to an Excitotoxin Through Distict Pathways," *Journal of Immunology*, vol. 163, pp. 3963-3968, 1999.

Wang, Yushan S. et al. "The Bacterial Endotoxin Lipopolysaccharide Causes Rapid Inappropriate Excitation in Rat Cortex," *Journal of Neurochemistry*, vol. 72, No. 2, pp. 652-660, 1999.

Yolken, R. H. "Endogenous Retroviruses and Schizophrenia," *Brain Research Reviews*, vol. 31, pp. 193-199, 2000.

Kleine, Tilmann O. et al. "Approach to discriminate subgroups in multiple sclerosis with cerebrospinal fluid (CSF) basic inflammation indices and TNF-$\alpha$, IL-$1_\beta$, IL-6, IL-8," *Brain Research Bulletin*, vol. 61, pp. 327-346, 2003.

Aarli, Johan A. "Role of Cytokines in Neurological Disorders," *Current Medicinal Chemistry*, vol. 10, pp. 1931-1937, 2003.

Vladic, Anton et al. "Cerebrospinal Fluid and Serum Protein Levels of Tumour Necrosis Factor-Alpha (TNF-$\alpha$), Interleukin-6 (IL-6) and Soluble Interleukin-6 Receptor (sIL-6R gp80) in Multiple Sclerosis Patients," *Cytokine*, vol. 20, No. 2, pp. 86-89, Oct. 21, 2002.

Miljkovic, Dj. et al. "Nitric oxide metabolites and interleukin-6 in Cerebrospinal fluid from multiple sclerosis patients," *European Journal of Neurology*, vol. 9, pp. 413-418, 2002.

Clerici, Mario. "Single-cell analysis of cytokine production shows different immune profiles in multiple sclerosis patients with active or quiescent disease," *Journal of Neuroimmunology*, vol. 121, pp. 88-101, 2001.

Fedetz, Maria. "The -174/-597 promoter polymorphisms in the interleukin-6 gene are not associated with susceptibility to multiple sclerosis," *Journal of Neurological Sciences*, vol. 190, pp. 69-72, 2001.

Stelmasiak, Zbigniew et al. "IL-6 and sIL-6R concentration in the cerebrospinal fluid and serum of MS patients," *Med. Sc. Monit.*, vol. 7, No. 5, pp. 914-918, 2001.

Vandenbroeck, K. "High-resolution analysis of IL-6 minisatellite polymorphism in Sardinian multiple sclerosis: effect on course and onset of disease," *Genes and Immunology*, vol. 1, pp. 460-463, 2000.

Stelmasiak, Zbigniew. "Interleukin-6 concentration in serum and cerebrospinal fluid in multiple sclerosis patients," *Med Sci Monit*, vol. 6, No. 6, pp. 1104-1108, 2000.

Schonrock, Lisa et al. "Interleukin-6 expression in human multiple sclerosis lesions," *Neuroscience Letters*, vol. 294, pp. 45-48, 2000.

Cornford, Eain M. et al. "New systems for delivery of drugs to the brain in neurological disease," *Lancet Neurology*, vol. 1, pp. 306-315, Sep. 2002.

Schmidt, Jens et al. "Drug targeting by long-circulating liposomal glucocorticosteroids increases therapeutic efficacy in a model of multiple sclerosis," *Brain*, vol. 126, pp. 1895-1904, 2003.

Pardridge, William M. "Blood-Brain Barrier Drug Targeting Enables Neuroprotection in Brain Ischemia Following Delayed Intravenous Administration of Neurotrophins," *Adv. Exp. Med. Biol.*, pp. 397-430, 2002.

Watanabe, Satoru et al. "Chemotherapeutic Targeting of Etoposide to Regions of the Brain on the Basis of Polyamine Level," *Journal of Drug Targeting*, vol. 10, No. 6, pp. 457-461, 2002.

Lahiri, Debomoy K. et al. "A Critical Analysis of New Molecular Targets and Strategies for Drug Developments in Alzheimer's Disease," *Current Drugs Targets*, vol. 4, pp. 97-112, 2003.

Scherrmann, J. M. "Drug delivery to brain via the blood-brain barrier," *Vascular Pharmacology*, vol. 38, pp. 349-354, 2002.
Wang, Jian-Xin et al. "Enhanced brain targeting by synthesis of 3', 5'-dioctanoyl-5-fluoro-2'-deoxyuridine and incorporation into solid lipid nanoparticles," *European Journal of Pharmaceuticals and Biopharmaceuticals*, vol. 54, pp. 285-290, 2002.
Doan, Kelly M. Mahar et al. "Passive Permeability and P-Glycoprotein-Mediated Efflux Differentate Central Nervous System (CNS) and Non-CNS Marketed Drugs," *Journal of Pharmacology and Experimental Therapeutics*, vol. 303, pp. 1029-1037, 2002.
Hosoya, Ken-ichi et al. "Recent advances in the brain-to-blood efflux transport across the blood-brain barrier," *International Journal of Pharmaceuticals*, vol. 248, pp. 15-29, 2002.
Mora, Margarita. "Design and Characterization of Liposomes Containing Long-Chain-N AcylPE$_s$ for Brain Delivery: Penetration of Liposome Incorporating $GM_1$ into the Rat Brain," *Pharmaceutical Research*, vol. 19, No. 10, Oct. 2002.
Perron, H. et al. "Herpes simplex virus ICP0 and ICP4 immediate early proteins strongly enhance expression of a retrovirus harboured by a leptomeningeal cell line from a patient with multiple sclerosis," *Journal of General Virology*, vol. 74, pp. 65-72, 1993.
Soldan, Samantha S. "Association of human herpes virus 6 (HHV-6) with multiple sclerosis: Increased IgM response to HHV-6 early antigen and detection of serum HHV-6 DNA," *Nature Medicine*, vol. 3, No. 12, pp. 1394-1397, 1997.
Haahr, S. "Is Multiple Sclerosis Caused by a Dual Infection with Retrovirus and Epstein-Barr Virus?," *Neuroepidemiology*, vol. 11, pp. 229-303, 1992.
Bergstrom, Tomas et al. "Isolation of Herpes Simplex Virus Type 1 During First Attack of Multiple Sclerosis," *Ann. Neurol.*, vol. 26, pp. 283-285, 1989.
Marx, Christine E. et al. "Cytokine Effects on Cortical Neuron MAP-2 Immunoreactivity: Implications for Schizophrenia," *Biol. Psychiatry*, vol. 50, pp. 743-749, 2001.
Maes, Michael et al. "Effects of atypical antipsychotics on the inflammatory response system in schizophrenic patients resistant to treatment with typical neuroleptics," *European Neuropsychopharmacology*, vol. 10, pp. 119-124, 2000.
Minagar, Alireza et al.. "The role of macrophage/microglia and astrocytes in the pathogenesis of three neurologic disorders: HIV-associated dementia, Alzheimer's disease, and multiple sclerosis," *Journal of the Neurological Sciences*, vol. 202, pp. 13-23, 2002.
Jeohn, Gwang-Ho et al. "Go6976 Protects Mesencephalic Neurons from Lipopolysaccharide-Elicited Death by Inhibiting p38 MAP Kinase Phosphorylation," *Annals New York Academy of Sciences*, pp. 347-359.
Gaser, Christian et al. "Ventricular Enlargement in Schizophrenia Related to Volume Reduction of the Thalmus, Striatum, and Superior Temportal Cortex," *American Journal of Psychiatry*, vol. 161, pp. 154-156, 2004.
Kurtzke, John F. "Disability Rating Scales in Multiple Sclerosis," *Annals New York Academy of Sciences*, vol. 36, pp. 347-360, 1984.
Karlsson, H. et al. "HERV-W-related RNA detected in plasma from individuals with recent-onset schizophrenia or schizoaffective disorder," *Molecular Psychiatry*, vol. 9, pp. 12-13, 2004.
Qiu, Zhihua et al. "Interleukin-6, β-amyloid peptide and NMDA interactions in rat cortical neurons," *Journal of Neuroimmunology*, vol. 139, pp. 51-57, 2003.
Jenner, Peter. "Oxidative Stress in Parkinson's Disease," *Annals of Neurology*, vol. 53, Supp. 3, pp. S26-S38, 2003.
Woodland, David L. "Human viral superantigens: to be or not to be transactivated?", *Trends in Immunology*, vol. 23, No. 5, p. 239, May 2002.

Pranzatelli, Michael R. "Innovations in Drug Delivery to the Central Nervous System," *Drugs of Today*, vol. 35, No. 6, pp. 435-448, 1999.
Merlo, A. et al. "Comparing monoclonal antibodies and small peptidic hormones for local targeting of malignant gliomas," *Acta Neurochir*, vol. 88, Supp., pp. 83-91, 2003.
Antony, Joseph M. et al. "Human endogenous retrovirus glycoprotein-mediated induction of redox reactants causes oligodendrocyte death and demyelination," *Nature Neuroscience*, vol. 7, No. 10, pp. 1088-1095, Oct. 2004.
Ng, Phillip C. et al. "Preparation and characterization of the Fab and $F(ab')_2$ fragments of aromatase activity-suppressing monoclonal antibody," *Steroids*, vol. 62, pp. 776-781, 1997.
Perron, H. et al. "In Vitro transmission and antigenicity of a retrovirus isolated from a multiple sclerosis patient," *Res. Virol*, vol. 143, pp. 337-350, 1992.
Serra, C. et al. "Multiple sclerosis and multiple sclerosis-associated retrovirus in Sardinia," *Neurol. Sci.*, vol. 22, pp. 171-173, 2001.
Zawada, Mariola et al. "MSRV *POL* Sequence Copy Number as a Potential Marker of Multiple Sclerosis," *Polish Journal of Pharmacology*, vol. 55, pp. 869-875, 2003.
Rolland, Alexandre. "Correlation between disease severity and in vitro cytokine production mediated by MSRV (Multiple Sclerosis associated Retro Viral element) envelope protein in patients with multiple sclerosis," *Journal of Neuroimmunology*, vol. 160, pp. 195-203, 2005.
Komurian-Pradel, F. et al. "Molecular Cloning and Characterization of MSRV-Related Sequences Associated with Retrovirus-like particles," *Virology*, vol. 260, pp. 1-9, 1999.
Perron, H. et al. "Human endogenous retrovirus (HERV)-W ENV and GAG proteins: Physiological expression in human brain and pathophysiological modulation in multiple sclerosis lesions," *Journal of NeuroVirology*, vol. 11, pp. 23-33, 2005.
Blazar, Bruce R. et al. "Anti-$CD3_e F(ab')_2$ Fragments Inhibit T Cell Expansion in Vivo During Graft-Versus-Host Disease or the Primary Immune Response to Nominal Antigen," *Journal of Immunology*, vol. 159, pp. 5821-5833, 1997.
Bird, Robert E. et al. "Single-Chain Antigen-Binding Proteins," *Science Reports*, vol. 242, pp. 423-426, Oct. 21, 1988.
Arakawa, Fumiko et al. "Cloning and Sequencing the $V_H$ and $V_K$ Genes of an Anti-CD3 Monoclonal Antibody, and Construction of a Mouse/Human Chimeric Antibody," *Journal Biochem*, vol. 120, pp. 657-662, 1996.
Chaudhary, Vijay K. et al. "A recombinant immunotoxin consisting of two antibody variable domains fused to *Pseudomonas* exotoxin," *Nature*, vol. 339, pp. 394-397, Jun. 1, 1989.
Mishra, Nirmal K. et al. "Continuous cultures of fused cells secreting antibody of predefined specificity," *Nature*, vol. 256, pp. 495-550, Aug. 7, 1975.
Galfre, G. et al. "Antibodies to major histocompatability antigens produced by hybrid cell lines," *Nature*, vol. 256, pp. 550-552, Aug. 7, 1975.
Jiang, Qingqi et al. "Cutting Edge: Lipopolysaccharide Induces Physical Proximity Between CD14 and Toll-Like Receptor 4 (TLR4) Prior to Nuclear Translocation of AF-$_κ$B," *Journal of Immunology*, vol. 165, pp. 3541-3544, 2000.
Lehnardt, Seija. "The Toll-Like Receptor TLR4 is Necessary for Lipopolysaccharide-Induced Oligodendrocyte Injury in the CNS," *Journal of Neuroscience*, vol. 22, No. 7, pp. 2478-2486, Apr. 1, 2002.
Serra, Caterina et al. "In Vitro modulation of the multiple sclerosis (MS)-associated retrovirus by cytokines: Implications for MS pathogenesis," *Journal of NeuroVirology*, vol. 9, pp. 637-643, 2003.

\* cited by examiner

A

B

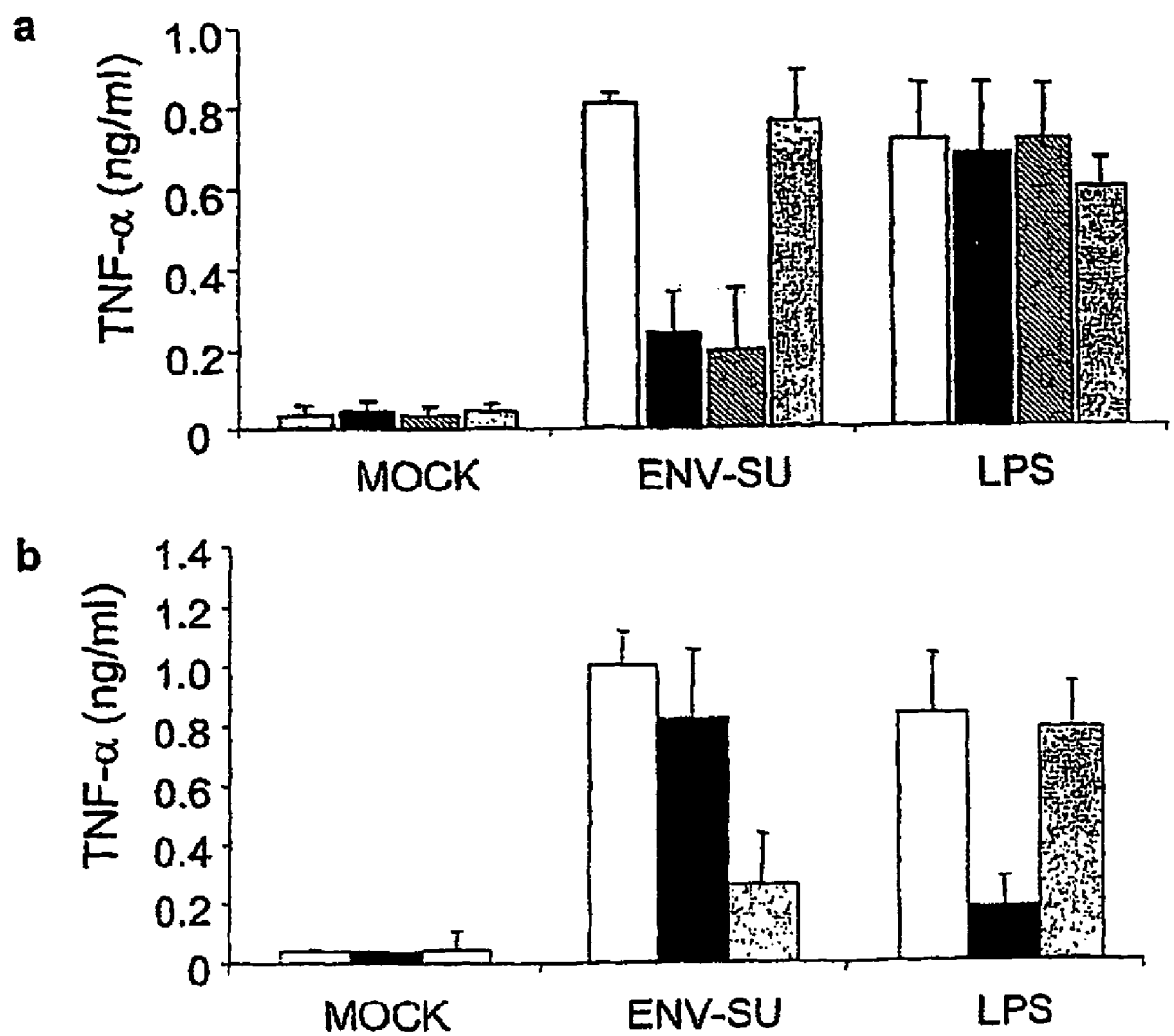
Fig. 15A-B

C

Fig. 23

SEQUENCE LISTING

```
<160> NUMBER OF SEQ ID NOS: 5

<210> SEQ ID NO 1
<211> LENGTH: 287
<212> TYPE: PRT
<213> ORGANISM: virus - MSRV/HERV-W

<400> SEQUENCE: 1

Ser Ser Ser Pro Tyr Gln Glu Phe Leu Trp Arg Thr Arg Leu Pro Gly
1               5                   10                  15

Asn Ile Asp Ala Pro Ser Tyr Arg Ser Leu Ser Lys Gly Asn Ser Thr
            20                  25                  30

Phe Thr Ala His Thr His Met Pro Arg Asn Cys Tyr Asn Ser Ala Thr
        35                  40                  45

Leu Cys Met His Ala Asn Thr His Tyr Trp Thr Gly Lys Met Ile Asn
    50                  55                  60

Pro Ser Cys Pro Gly Gly Leu Gly Ala Thr Val Cys Trp Thr Tyr Phe
65                  70                  75                  80

Thr His Thr Ser Met Ser Asp Gly Gly Gly Ile Gln Gly Gln Ala Arg
                85                  90                  95

Glu Lys Gln Val Lys Glu Ala Ile Ser Gln Leu Thr Arg Gly His Ser
            100                 105                 110
```

```
Thr Pro Ser Pro Tyr Lys Gly Leu Val Leu Ser Lys Leu His Glu Thr
        115                 120                 125

Leu Arg Thr His Thr Arg Leu Val Ser Leu Phe Asn Thr Thr Leu Thr
130                 135                 140

Arg Leu His Glu Val Ser Ala Gln Asn Pro Thr Asn Cys Trp Met Cys
145                 150                 155                 160

Leu Pro Leu His Phe Arg Pro Tyr Ile Ser Ile Pro Val Pro Glu Gln
                165                 170                 175

Trp Asn Asn Phe Ser Thr Glu Ile Asn Thr Thr Ser Val Leu Val Gly
                180                 185                 190

Pro Leu Val Ser Asn Leu Glu Ile Thr His Thr Ser Asn Leu Thr Cys
            195                 200                 205

Val Lys Phe Ser Asn Thr Ile Asp Thr Thr Ser Ser Gln Cys Ile Arg
210                 215                 220

Trp Val Thr Pro Pro Thr Arg Ile Val Cys Leu Pro Ser Gly Ile Phe
225                 230                 235                 240

Phe Val Cys Gly Thr Ser Ala Tyr His Cys Leu Asn Gly Ser Ser Glu
                245                 250                 255

Ser Met Cys Phe Leu Ser Phe Leu Val Pro Pro Met Thr Ile Tyr Thr
                260                 265                 270

Glu Gln Asp Leu Tyr Asn His Val Val Pro Lys Pro His Asn Lys
            275                 280                 285

<210> SEQ ID NO 2
<211> LENGTH: 29
<212> TYPE: PRT
<213> ORGANISM: virus - MSRV/HERV-W

<400> SEQUENCE: 2

Met Ala Leu Pro Tyr His Thr Phe Leu Phe Thr Val Leu Leu Pro Pro
1               5                   10                  15

Phe Ala Leu Thr Ala Pro Pro Cys Cys Cys Thr Thr
                20                  25

<210> SEQ ID NO 3
<211> LENGTH: 316
<212> TYPE: PRT
<213> ORGANISM: virus - HSRV/HERV-W

<400> SEQUENCE: 3

Met Ala Leu Pro Tyr His Thr Phe Leu Phe Thr Val Leu Leu Pro Pro
1               5                   10                  15

Phe Ala Leu Thr Ala Pro Pro Cys Cys Cys Thr Thr Ser Ser Ser
                20                  25                  30

Pro Tyr Gln Glu Phe Leu Trp Arg Thr Arg Leu Pro Gly Asn Ile Asp
            35                  40                  45

Ala Pro Ser Tyr Arg Ser Leu Ser Lys Gly Asn Ser Thr Phe Thr Ala
            50                  55                  60

His Thr His Met Pro Arg Asn Cys Tyr Asn Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Ala Thr Val Cys Trp Thr Tyr Phe Thr His Thr
            100                 105                 110

Ser Met Ser Asp Gly Gly Gly Ile Gln Gly Gln Ala Arg Glu Lys Gln
            115                 120                 125
```

```
Val Lys Glu Ala Ile Ser Gln Leu Thr Arg Gly His Ser Thr Pro Ser
130                 135                 140

Pro Tyr Lys Gly Leu Val Leu Ser Lys Leu His Glu Thr Leu Arg Thr
145                 150                 155                 160

His Thr Arg Leu Val Ser Leu Phe Asn Thr Thr Leu Thr Arg Leu His
                165                 170                 175

Glu Val Ser Ala Gln Asn Pro Thr Asn Cys Trp Met Cys Leu Pro Leu
            180                 185                 190

His Phe Arg Pro Tyr Ile Ser Ile Pro Val Pro Glu Gln Trp Asn Asn
                195                 200                 205

Phe Ser Thr Glu Ile Asn Thr Thr Ser Val Leu Val Gly Pro Leu Val
210                 215                 220

Ser Asn Leu Glu Ile Thr His Thr Ser Asn Leu Thr Cys Val Lys Phe
225                 230                 235                 240

Ser Asn Thr Ile Asp Thr Thr Ser Ser Gln Cys Ile Arg Trp Val Thr
                245                 250                 255

Pro Pro Thr Arg Ile Val Cys Leu Pro Ser Gly Ile Phe Phe Val Cys
                260                 265                 270

Gly Thr Ser Ala Tyr His Cys Leu Asn Gly Ser Ser Glu Ser Met Cys
                275                 280                 285

Phe Leu Ser Phe Leu Val Pro Pro Met Thr Ile Tyr Thr Glu Gln Asp
290                 295                 300

Leu Tyr Asn His Val Val Pro Lys Pro His Asn Lys
305                 310                 315

<210> SEQ ID NO 4
<211> LENGTH: 538
<212> TYPE: PRT
<213> ORGANISM: virus - HERV-W7q

<400> SEQUENCE: 4

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
                20                  25                  30

Pro Tyr Gln Glu Phe Leu Trp Arg Met Gln Arg Pro Gly Asn Ile Asp
            35                  40                  45

Ala Pro Ser Tyr Arg Ser Leu Ser Lys Gly Thr Pro Thr Phe Thr Ala
        50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Gly Val Gln Asp Gln Ala Arg Glu Lys His
        115                 120                 125

Val Lys Glu Val Ile Ser Gln Leu Thr Arg Val His Gly Thr Ser Ser
130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190
```

```
Asn Phe Arg Pro Tyr Val Ser Ile Pro Val Pro Glu Gln Trp Asn Asn
            195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Leu Phe
225                 230                 235                 240

Ser Asn Thr Thr Tyr Thr Thr Asn Ser Gln Cys Ile Arg Tyr Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Ala Val Val Leu Gln Asn Arg Arg
    370                 375                 380

Ala Leu Asp Leu Leu Thr Ala Cys Arg Gly Gly Thr Cys Leu Phe Leu
385                 390                 395                 400

Gly Glu Glu Cys Cys Thr Thr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
    530                 535

<210> SEQ ID NO 5
<211> LENGTH: 542
<212> TYPE: PRT
<213> ORGANISM: virus - MSRV

<400> SEQUENCE: 5

Met Ala Leu Pro Tyr His Thr Phe Leu Phe Thr Val Leu Leu Pro Pro
1               5                   10                  15

Phe Ala Leu Thr Ala Pro Pro Pro Cys Cys Cys Thr Thr Ser Ser Ser
```

```
                    20                  25                  30
Pro Tyr Gln Glu Phe Leu Trp Arg Thr Arg Leu Pro Gly Asn Ile Asp
         35                  40                  45
Ala Pro Ser Tyr Arg Ser Leu Ser Lys Gly Asn Ser Thr Phe Thr Ala
 50                  55                  60
His Thr His Met Pro Arg Asn Cys Tyr Asn Ser Ala Thr Leu Cys Met
 65                  70                  75                  80
His Ala Asn Thr His Tyr Trp Thr Gly Lys Met Ile Asn Pro Ser Cys
                 85                  90                  95
Pro Gly Gly Leu Gly Ala Thr Val Cys Trp Thr Tyr Phe Thr His Thr
            100                 105                 110
Ser Met Ser Asp Gly Gly Ile Gln Gly Gln Ala Arg Glu Lys Gln
        115                 120                 125
Val Lys Glu Ala Ile Ser Gln Leu Thr Arg Gly His Ser Thr Pro Ser
130                 135                 140
Pro Tyr Lys Gly Leu Val Leu Ser Lys Leu His Glu Thr Leu Arg Thr
145                 150                 155                 160
His Thr Arg Leu Val Ser Leu Phe Asn Thr Thr Leu Thr Arg Leu His
                165                 170                 175
Glu Val Ser Ala Gln Asn Pro Thr Asn Cys Trp Met Cys Leu Pro Leu
            180                 185                 190
His Phe Arg Pro Tyr Ile Ser Ile Pro Val Pro Glu Gln Trp Asn Asn
        195                 200                 205
Phe Ser Thr Glu Ile Asn Thr Thr Ser Val Leu Val Gly Pro Leu Val
210                 215                 220
Ser Asn Leu Glu Ile Thr His Thr Ser Asn Leu Thr Cys Val Leu Phe
225                 230                 235                 240
Ser Asn Thr Ile Asp Thr Thr Ser Ser Gln Cys Ile Arg Tyr Val Thr
                245                 250                 255
Pro Pro Thr Arg Ile Val Cys Leu Pro Ser Gly Ile Phe Phe Val Cys
            260                 265                 270
Gly Thr Ser Ala Tyr His Cys Leu Asn Gly Ser Ser Glu Ser Met Cys
        275                 280                 285
Phe Leu Ser Phe Leu Val Pro Pro Met Thr Ile Tyr Thr Glu Gln Asp
290                 295                 300
Leu Tyr Asn His Val Val Pro Lys Pro His Asn Lys Arg Val Pro Ile
305                 310                 315                 320
Leu Pro Phe Val Ile Arg Ala Gly Val Leu Gly Arg Leu Gly Thr Gly
                325                 330                 335
Ile Gly Ser Ile Thr Thr Ser Thr Gln Phe Tyr Tyr Lys Leu Ser Gln
            340                 345                 350
Glu Ile Asn Gly Asp Met Glu Gln Val Thr Asp Ser Leu Val Thr Leu
        355                 360                 365
Gln Asp Gln Leu Asn Ser Leu Ala Ala Val Val Leu Gln Asn Arg Arg
370                 375                 380
Ala Leu Asp Leu Leu Thr Ala Lys Arg Gly Gly Thr Cys Leu Phe Leu
385                 390                 395                 400
Gly Glu Glu Arg Cys Thr Thr Val Asn Gln Ser Arg Ile Val Thr Glu
                405                 410                 415
Lys Val Lys Glu Ile Arg Asp Arg Ile Gln Cys Arg Ala Glu Glu Leu
            420                 425                 430
Gln Asn Thr Cys Arg Trp Gly Leu Leu Ser Gln Trp Met Pro Trp Thr
        435                 440                 445
```

```
Leu Pro Phe Leu Gly Pro Leu Ala Ala Ile Ile Phe Leu Leu Leu Phe
    450             455             460

Gly Pro Cys Ile Phe Asn Phe Leu Val Lys Phe Val Ser Ser Arg Ile
465             470             475                     480

Glu Ala Val Lys Leu Gln Ile Val Leu Gln Met Glu Pro Gln Met Gln
            485             490                 495

Ser Met Thr Lys Ile Tyr Arg Gly Pro Leu Asp Arg Pro Ala Arg Leu
            500             505             510

Cys Ser Asp Val Asn Asp Ile Cys Val Thr Pro Pro Glu Glu Ile Ser
        515             520             525

Thr Ala Gln Pro Leu Leu His Ser Asn Ser Val Gly Ser Ser
    530             535             540
```

COMPOSITION FOR TREATING PATHOLOGY ASSOCIATED WITH MSRV/HERV-W

For several years, many studies have demonstrated the important expression of various retroviruses, in particular endogenous retroviruses (HERVs), in pathologies such as diabetes [1], multiple sclerosis (MS) [2] and schizophrenia (SCZ) [3]. HERVs possess homologies with the known animal retroviruses and probably originate from their integration into the human germ line. The sequences of these HERVs in the human genome are generally incomplete even though whole proviral sequences have already been identified.

Retroviral particles in cultures of leptomeningeal cells from patients suffering from MS have already been isolated [4]. The study of these particles has shown that they possess genetic sequences homologous to human DNA but define a new family of endogenous retroviruses (HERV-W) [2, 5, 6]. The presence of MSRV in the serum and/or the cerebrospinal fluid (CSF) of patients has now been confirmed by various teams [7-9] and a correlation between the viral load and the evolution of the disease has been demonstrated [10]. It has subsequently been demonstrated that MSRV and its envelope protein have T-lymphocyte-mediated pro-inflammatory properties, of superantigen (SAg) type [11]. An animal model (humanized SCID mice) has been developed, confirming in vivo the immunopathogenic potential of such particles, and in particular their ability to induce the secretion of pro-inflammatory cytokines, mediated by T lymphocytes [12].

In the subsequent description, the viruses of the MSRV/HERV-W family will be called MSRV or MSRV/HERV-W, without distinction.

Other pathologies exhibit, like MS, an immune system activation profile characterized by the presence of large amounts of IL-6. Among them, schizophrenia (SCZ), —a neuropsychiatric disease associated with genetic and environmental factors—, presents, depending on the case, serum-IL-6 levels which are much higher than normal [13]. Moreover, retroviral sequences similar to those of MSRV have been identified in SCZ patients [3]. In addition, more recently, it has been demonstrated that the SCF of newly diagnosed SCZ patients exhibits retroviral sequences of the MSRV/HERV-W family associated with circulating particles [14].

Such an expression is compatible with MSRV/HERV-W having a role in various neurological pathologies by means of the pro-inflammatory effects of its envelope protein and of the activation pathway involved. This retroviral element (itself under the control of activation cofactors) and its associated effects are entirely relevant in the case of inflammatory demyelinating diseases [15]. In the case of schizophrenia, such an inflammation revealed at the systemic level through the overexpression of IL-6 is also relevant, locally at the level of the gray matter in the brain, with regard to the known neurotoxic and excitotoxic effects of the inflammation mediated by microgliocytes/macrophages in the brain [16-30].

The differential expression of MSRV/HERV-W RNA sequences has also been reported in the frontal cortex tissue of schizophrenic patients, and not in controls, including in particular manic depressive psychoses (bipolar disorders) [31]. Furthermore, the systemic reflection of this "MSRV/HERV-W" retroviral differential has been demonstrated in the blood of homozygous twins with conflicting schizophrenic pathology, thus corroborating the existence of a "systemic" replica that can in particular play a role in the hyperexpression of circulating IL-6 previously reported [3].

The effects of the MSRV/HERV-W envelope protein in schizophrenic patients are part of the pathogenic cascade of schizophrenia, at the level of the role of specific inflammatory factors in the generation of cortical or subcortical, neurotoxic and/or excitotoxic signals.

At this time, corroborating publications from various independent teams exist, which show an association between the elements of the MSRV/HERV-W family and pathologies such as MS and SCZ, but other diseases could also prove to be involved.

The present inventors have now shown, unexpectedly, that the Env protein of MSRV/HERV-W has another pro-inflammatory activity, independent of that mediated by T lymphocytes, this novel pro-inflammatory activity involving cells other than T cells and involving a receptor other than the T cell receptor (TCR), and resulting in the activation of a pro-inflammatory pathway other than that which results from the activation of the TCR by a superantigen. This novel pro-inflammatory activity is therefore different from the pro-inflammatory activation caused by a superantigenic function which, by definition, involves binding to the T lymphocyte TCR. The inventors have found that it is precisely the soluble fraction domain (Env-SU) of the MSRV/HERV-W envelope protein which is responsible for these novel pro-inflammatory effects mediated by antigen-presenting cells (macrophages, monocytes, dendritic cells and micrdgliocites) and a receptor not identified, up until now, for its role in the triggering of the pro-inflammatory effects mediated by MSRV/HERV-W Env-SU. Thus, Env-SU, naturally present at the surface of the retroviral particles, targets the antigen-presenting cells (APCs), activates them and induces the secretion of large amounts of TNF-α, of IL-1β and of IL-6. These pro-inflammatory effects have been studied in patients suffering from MS and then compared with those obtained in donors. The inventors have thus shown that the production of IL-6 induced by Env-SU is increased in MS patients and correlates with their clinical score (EDSS). The increased presence of IL-6 in the serum, the SCF and the lesions of MS patients [32-37] is presumed to play an important role in the development and the persistence of the lesions observed in the central nervous system of MS patients.

The present inventors have therefore found, surprisingly, that the Env-SU receptor involved in these novel pro-inflammatory effects is the human TLR4 (Toll-like receptor 4) protein. The gene encoding TLR4 is located on chromosome 9 (9q32-q33). The protein consists of 839 amino acids and has a molecular weight of 95679 Da. It was known that TLR4 cooperates with another molecule, called MD-2, and that, together with CD14, this complex is involved in the recognition of bacterial lipopolysaccharides (LPSs), resulting in activation of the NF-kappa-B factor, in cytokine secretion and in the inflammatory response, but its role of receptor for the soluble fraction of the MSRV/HERV-W envelope protein (Env-SU) was not known before the present invention. Since the TLR4 protein is not expressed on T lymphocytes, the latter are not the primary targets of the effects demonstrated here with the TLR4 receptor. The inventors have also shown that the MSRV retroviral particles associated with circulating RNA detected in the biological fluids of patients are, irrespective of any retroviral replication, inducers of this novel early pro-inflammatory activation pathway involving the TLR4 receptor present on antigen-presenting cells such as macrophages, monocytes, dendritic cells and microgliocytes. For this, they inactivated the MSRV virions purified from producer culture supernatants [4] and tested their activity related to the presence of the MSRV/HERV-W Env protein. The results presented in the experimental section confirm that the early pathway for inactivation of innate immunity by the TLR4 receptor is targeted by the envelope protein in the soluble form, Env-SU, and in the membrane-bound form at the surface of the MSRV virions.

The results obtained in the context of the present invention therefore make it possible to establish immunotherapy strategies in pathologies, in particular neurological pathologies, such as MS and SCZ, and have in particular made it possible to identify the vectors capable of transporting one or more therapeutic agents across the blood-brain barrier. One of the essential aspects of the results of the invention, in the context of therapy, is that they made it possible to target an inflammatory component associated with the activation of brain microgliocytes/macrophages, with a unique specificity in this domain by virtue of the identification of the "MSRV/HERV-W Env-SU and TLR4" ligand/receptor system involved in the generation of the early inflammatory signals which, for example, initiate a demyelinating cascade when they originate from microgliocytes/macrophages located in the white matter (MS) or an excitotoxic/neurotoxic cascade when they are produced by these same cells in the gray matter (SCZ).

Thus, a subject of the present invention is a method for treating an individual exhibiting a pathology associated with the presence of MSRV/HERV-W, comprising the administration to the individual of a therapeutic composition or medicament comprising at least one antibody chosen from the group (i) of anti-MSRV/HERV-W Env-SU antibodies capable of binding specifically (which bind specifically) to the soluble fraction of the MSRV/HERV-W Env protein or from the group (ii) of antibodies capable of binding specifically (which bind specifically) to the TLR4 receptor for the soluble fraction of the MSRV/HERV-W Env-SU protein, so as to inhibit the pro-inflammatory cascade induced by the activation of MSRV/HERV-W, and a carrier plus, if necessary, a pharmaceutically acceptable vector. Said antibodies inhibit the pro-inflammatory cascade induced by the activation of MSRV/HERV-W Env-SU. Said method is in particular used for the treatment of MS and SCZ, but can be applied to the treatment of other diseases if they are associated with expression of the pro-inflammatory protein of MSRV/HERV-W in a context where the latter initiates a pathological cascade.

Said anti-Env-SU antibodies are in particular capable of binding to a region which corresponds to amino acids 122-131 (inclusive) and/or to a region which corresponds to amino acids 312-316 (inclusive) and/or to a region which corresponds to amino acids 181-186 (inclusive) of the sequence identified in SEQ ID NO: 3.

According to the method of the invention, a composition or medicament comprising at least one anti-MSRV/HERV-W Env-SU antibody or at least one anti-TLR4 antibody can be administered to the patient. In one embodiment of the method of the invention, a composition or a medicament comprising at least one anti-MSRV/HERV-W Env-SU antibody and at least one anti-TLR4 antibody is administered to the patient.

Preferably, in the method of the invention, the anti-Env-SU antibody is chosen from the following antibodies: anti-MSRV/HERV-W Env-SU monoclonal antibodies (antibodies 3B2H4, 13H5A5 and 3H10F10 (bioMérieux)), and the anti-TLR4 antibody is the anti-human TLR4 antibody HTA125 (sold by the company eBioscience). The method of obtaining the bioMérieux monoclonal antibodies is described in the description which follows. The abovementioned antibodies have the original, and up until then unknown, characteristic of being neutralizing with respect to the pro-inflammatory activity newly demonstrated on antigen-presenting cells by the TLR4 receptor.

The anti-TLR4 or anti-Env-SU antibodies are administered to the individual by means of a pharmaceutically acceptable carrier, associated, if necessary, with a pharmaceutically acceptable vector for transporting them across the blood-brain barrier (BBB). If, as is the case for MS, at a certain stage of the evolution of the pathology there is opening of the blood-brain barrier, it is not necessary to use such vectors, but when there is no opening of the blood-brain barrier, which is also the case for SCZ, such vectors are necessary. These vectors are well known [38-45]. The therapeutic approach targets an inflammatory component associated with the activation of brain microgliocytes/macrophages, with a unique specificity in this domain. This specificity is associated with the identification of the "MSRV Env-SU and TLR4" ligand-receptor system involved in the generation of the early inflammatory signals which, for example, initiate a demyelinating cascade when they originate from microgliocytes/macrophages located in the white matter (MS) or an excitotoxic/neurotoxic cascade when they are produced by these same cells in the gray matter (SCZ).

The utility of the anti-MSRV Env-SU or anti-TLR4 antibodies is to block "at the source" the pro-inflammatory cascade induced by the expression of MSRV/HERV-W (itself induced by infectious cofactors of herpesvirus type, by hormone signals or by specific cytokines, which are variable depending on pathologies) in the various diseases associated with a pathological expression of MSRV/HERV-W.

Thus, a subject of the present invention is a composition, it being understood that this composition is for therapeutic purposes, which comprises at least one antibody chosen from the group (i) of anti-MSRV/HERV-W Env-SU antibodies or from the group (ii) of anti-TLR4 antibodies, capable of binding specifically (which bind specifically) to the soluble fraction of the MSRV/HERV-W Env protein or to the TLR4 receptor for the soluble fraction of the MSRV/HERV-W Env protein, and a pharmaceutically acceptable carrier. If necessary, said composition also comprises a pharmaceutically acceptable vector; said antibodies inhibiting the pro-inflammatory cascade induced by the activation of MSRV/HERV-W Env-SU. Preferably, the composition comprises at least one anti-MSRV/HERV-W Env-SU antibody and at least one anti-TLR4 antibody. The antibodies that are preferred in this composition are the anti-MSRV/HERV-W Env-SU antibodies (3B2H4, 13H5A5 and 3H10F10) and the anti-TLR4 antibody HTA125. The abovementioned antibodies are monoclonal antibodies which are "neutralizing" with respect to the newly demonstrated pro-inflammatory activity on antigen-presenting cells via the TLR4 receptor.

Said anti-Env-SU antibodies are in particular capable of binding to a region which corresponds to amino acids 122-131 (inclusive) and/or to a region which corresponds to amino acids 312-316 (inclusive) and/or to a region which corresponds to amino acids 181-186 (inclusive) of the sequence identified in SEQ ID NO: 3.

A subject of the invention is also the use of at least one antibody chosen from the group (i) of anti-MSRV/HERV-W Env-SU antibodies or from the group (ii) of anti-TLR4 antibodies, capable of binding specifically to the soluble fraction of the MSRV/HERV-W Env protein or to the TLR4 receptor for the soluble fraction of the MSRV/HERV-W Env protein, for the preparation of a medicament; said antibodies inhibiting the pro-inflammatory cascade induced by the activation of MSRV/HERV-W Env-SU. In particular, at least one anti-MSRV/HERV-W Env-SU antibody and at least one anti-TLR4 antibody are used. The anti-HERV-W Env-SU antibody is chosen from the antibodies 3B2H4, 13H5A5 and 13H10F10 and the anti-TLR4 antibody is the antibody HTA125. This use is implemented for the treatment of a pathology associated with MSRV/HERV-W, such as multiple sclerosis or schizophrenia.

Said anti-Env-SU antibodies are in particular capable of binding to a region which corresponds to amino acids 12-131 (inclusive) and/or to a region which corresponds to amino acids 312-316 (inclusive) and/or to a region which corresponds to amino acids 181-186 (inclusive) of the sequence identified in SEQ ID NO: 3.

A subject of the invention is also antibodies chosen from the anti-MSRV/HERV-W Env-SU and anti-TLR4 antibodies capable of binding specifically (which bind specifically) to the soluble fraction of the MSRV/HERV-W Env protein or capable of binding specifically (which bind specifically) to the TLR4 receptor for the soluble fraction of the MSRV/HERV-W Env protein, for inhibiting the pro-inflammatory cascade induced by the activation of MSRV/HERV-W, in particular the antibodies 3B2H4, 13H5A5 and 13H10F10. However, it is within the scope of those skilled in the art to produce and to select other antibodies, the condition for the selection being that the antibodies selected are capable of inhibiting the pro-inflammatory effect of Env-SU in the in vitro assay described in the experimental section which follows.

The term "antibodies" used in the present invention includes monoclonal antibodies, chimeric antibodies, humanized antibodies, recombinant antibodies and fragments of said antibodies, which are characterized by a high affinity for the soluble fraction of the MSRV/HERV-W envelope protein and which exhibit no toxicity or a very weak toxicity. In particular, it is preferable to use an antibody whose variable region and/or constant region is weakly immunogenic for the individual to whom it is administered. The antibodies of the present invention are characterized by their ability to treat patients exhibiting pathologies associated with MSRV/HERV-W, while at the same time exhibiting no toxicity or a very weak toxicity. The weak immunogenicity and/or the high affinity of these antibodies may contribute to the therapeutic results achieved.

The term "antibody fragment" is intended to mean the F(ab)2, Fab, Fab' and sFv fragments (Blazar et al., 1997, Journal of Immunology 159: 5821-5833 and Bird et al., 1988, Science 242: 423-426) of a native antibody, and the term "chimeric antibody" is intended to mean, inter alia, a chimeric derivative of a native antibody (see, for example, Arakawa et al., 1996, J. Biochem 120: 657-662 and Chaudray et al., 1989, Nature 339: 394-397).

The production of monoclonal antibodies is part of the general knowledge of those skilled in the art. By way of reference, mention may be made of Köhler G. and Milstein C. (1975): Continuous culture of fused cells secreting antibody of predefined specificity, Nature 256: 495-497 and Galfre G. et al. (1977) Nature, 266: 522-550. The immunogen can be coupled to keyhole lymphet hemocyanin (KLH peptide) as a support for the immunization or to serum albumin (SA peptide). The animals are subjected to an injection of the immunogen using Freund's adjuvant. The sera and the hybridoma culture supernatants derived from the immunized animals are analyzed for their specificity and their selectivity using conventional techniques, such as, for example, ELISA assays or Western blotting. The hybridomas producing the most specific and most sensitive antibodies are selected. Monoclonal antibodies can also be produced in vitro by cell culture of the hybridomas produced or by recovery of ascites fluid, after intraperitoneal injection of the hybridomas into mice. Irrespective of the method of production, a supernatant or as ascites, the antibodies are then purified. The purification methods used are essentially filtration on ion exchange gel and exclusion chromatography or affinity chromatography (protein A or G). The antibodies are screened in functional assays so as to select the most effective antibodies. The in vitro production of antibodies, of antibody fragments and of chimeric antibodies produced by genetic engineering is well known to those skilled in the art. By way of example, antibodies can be produced by cloning of the cDNA obtained from the RNA encoding the variable fragment (scFv) of the antibody. The "humanized" forms of nonhuman antibodies, for example murine antibodies, are chimeric antibodies which comprise a minimum sequence derived from a nonhuman immunoglobulin. For the most part, humanized antibodies are human immunoglobulins (recipient antibody) in which residues of a hypervariable region of the receptor are replaced with residues of a hypervariable region of nonhuman donor species (donor antibody), such as mouse, rat, rabbit or nonhuman primate, having the specificity, the affinity and the capacity desired. In certain cases, the residues (FR) of the Fv region of the human immunoglobulin are replaced with corresponding nonhuman residues. Furthermore, the humanized antibodies can comprise residues which are not found in the recipient antibody or in the donor antibody. These modifications can be made so as to improve the effectiveness of the antibody. In general, the humanized antibody will comprise at least one, and preferably two, variable domains, in which all or virtually all of the hypervariable loops correspond to a nonhuman immunoglobulin and all or virtually all of the FR regions will be those of a human immunoglobulin. The humanized antibodies may optionally also comprise at least one portion of a constant region (Fc) of an immunoglobulin, such as a human immunoglobulin. In general, the variable region is derived from a nonhuman mammalian antibody and the constant region is derived from a human immunoglobulin. Preferably, the variable region chosen exhibits a weak immunogenicity and is combined with a constant region which also exhibits a weak immunogenicity.

These antibodies are preferably the following "neutralizing" antibodies:
  anti-MSRV/HERV-W Env-SU monoclonal antibodies: antibodies 3B2H4, 13H5A5 and 13H10F10 (bioMérieux),
  anti-TLR4 antibodies: anti-human TLR4 monoclonal antibody HTA125 (sold by the company eBioscience).

The anti-MSRV/HERV-W Env-SU antibodies are produced according to the protocols described below.

Production of the antibody 3B2H4:

The mice are immunized according to the following protocol: on day D0, intraperitoneal injection of 20 μg of immunogen, consisting of the purified recombinant MSRV/Env protein, as described previously [11] in the presence of complete Freund's adjuvant. On days D14 and D28, further intraperitoneal injection of the same amount of immunogen in the presence of incomplete Freund's adjuvant. Four, three and two days before the fusion, intraperitoneal injection of 100 μg of immunogen diluted in physiological saline.

400 supernatants were screened by the indirect ELISA technique. The plates were coated with 100 μl of antigen at 1 μg/ml in 0.05 M bicarbonate buffer, pH 9.6. The coated plates were incubated overnight at a temperature of 18-22° C. The plates were saturated with 200 μl of PBS-1% milk and subjected to incubation for 1 hour at 37°+/−2° C. 100 μl of supernatants or of ascites fluid diluted in PBS buffer-0.05% Tween 20 were added and the plates were incubated for 1 hour at 37°+/−2° C. 100 μl of goat anti-mouse Ig (H+L) polyclonal antibody conjugated to alkaline phosphatase (AP) (Jackson Immunoresearch ref: 115-055-062), diluted in PBS buffer- 1% BSA, to 1/2000, were added and the plates were then incubated for 1 hour at 37°+/−2° C. 100 µl of PNPP (Biomérieux ref 60002990) at a concentration of 2 mg/ml in DEA-HCL (Biomérieux ref 60002989), pH=9.8, were added. The plates were then subjected to incubation for 30 minutes at a temperature of 37°+/−2° C. The reaction was blocked by the addition of 100 µl of 1N NaOH. Three washes were performed between each step, with 300 µl of PBS-0.05% Tween 20. An additional wash in distilled water is performed before the PNPP is added.

22 supernatants were found to be positive by indirect ELISA with an OD>0.2, corresponding to four times the background noise. After the specificity assays, a single antibody is produced.

Production of the antibodies 13H5A5 and 3H10F10:

The mice are immunized according to the following protocol: on day D0, intraperitoneal injection of 40 µg of immunogen, consisting of the purified recombinant MSRV/Env protein as described [11], in the presence of complete Freund's adjuvant. On days D14, D28 and D78, a further intraperitoneal injection of the same amount of immunogen in the presence of incomplete Freund's adjuvant. Four, three and two days before the fusion, an intraperitoneal injection of 50 µg of immunogen diluted in physiological saline.

1350 supernatants were screened by the indirect ELISA technique, as described above.

39 supernatants were found to be positive by indirect ELISA with an OD>0.4, corresponding to four times the background noise. After the specificity assays, two antibodies are produced.

The abovementioned anti-Env-SU and anti-TLR4 antibodies are used for the preparation of a medicament or therapeutic composition for the treatment of pathologies associated with MSRV/HERV-W, as described above. In the composition for therapeutic purposes of the present invention, the antibody or active ingredient is combined with a pharmaceutically acceptable carrier and, optionally, with a pharmaceutically acceptable vector. The pharmaceutically acceptable carriers are determined and chosen as a function of the method of administration selected and of the standard practice in the pharmaceutical field. Because the proteins are subjected to digestion when they are administered orally, a parenteral, such as intravenous, subcutaneous or intramuscular, administration should normally be used to optimize the absorption. The pharmaceutically acceptable carriers are described, for example, in Remington's Pharmaceutical Sciences 16$^{th}$ ed., Mack Publishing Co. For example, a parenteral composition suitable for administration by injection is prepared by dissolving 1.5% by weight of the active ingredient in a 0.9% sodium chloride solution. It may be necessary to combine the antibody with a selected vector which allows the antibody to cross the BBB. The nontransportable antibody can thus be coupled to a transportable vector, such as cationized albumin, transferrin, insulin or insulin-like growth factor, or to a fragment of said proteins. It has in particular already been shown that nontransportable monoclonal antibodies (IgG3), linked to a transporting vector, such as transferrin or insulin-like growth factor, not only are capable of crossing the BBB, but also that the functional properties of these antibodies are conserved. Other studies have already shown that neuro-pharmaceutical products can be delivered into the brain via liposomes. This approach is also important since it offers a mechanism via which any molecule which can be encapsulated in a liposome can be directed to the brain.

The antibodies can be administered either as individual therapeutic agents, or in combination with other therapeutic agents so as to increase and improve the treatment. The dosage will of course depend on known factors, such as the pharmacodynamic characteristics of the specific agent, and on its route of administration, but also on factors such as age, weight, frequency of treatment and the desired and expected effect. Usually, a daily dose for an active ingredient is between 0.01 and 100 milligrams per kilogram for a human being. Normally, 1 to 40 milligrams per kilogram per day, administered as one or more daily doses, is an effective amount for obtaining the desired effect.

The invention also relates to the use of MSRV/HERV-W Env-SU for determining the state of reactivity of blood mononuclear cells of patients suffering from multiple sclerosis or from schizophrenia by assaying cytokines, chosen from IL-6, IL-12-p40 and TNF-α.

FIGURES

FIG. 1 represents the structures of the Env pV14 envelope, of the signal peptide and of the soluble fraction of the Env-SU envelope and the amino acid sequence of the signal peptide and of the soluble fraction of the Env-SU envelope. FIG. 1(a) corresponds to the structure of Env pV14 (the complete envelope protein of MSRV) and to the structure of the signal peptide and of the soluble fraction of the Env-SU envelope. The soluble fraction of the envelope (Env-SU) corresponds to a fraction of 287 amino acids representing the soluble extracellular unit, cleaved at position K316 of the complete Env pV14 protein. FIG. 1(b) (SEQ ID NO: 3) represents the amino acid sequence of the signal peptide (SEQ ID NO: 2) and of Env SU (SEQ ID NO: 1). In FIG. 1(b), the amino acid sequence of the signal peptide is boxed in and the soluble fraction of the envelope (Env-SU) is indicated in bold characters. The complete sequence of the Env pV14 envelope is available in GenBank under the accession number AF331500. The various parts of the Env pV14 protein are generally defined as described now, with reference to FIG. 1(a):

the signal peptide begins at amino acid 1 and ends at amino acid 29 (inclusive)(amino acid residues 1-29 of SEQ ID NO: 5), Env-SU begins at amino acid 30 and ends at amino acid 316 (inclusive)(amino acids residues 30-316 of SEQ ID NO: 5), and the transmembrane domain begins at amino acid 317 and ends at amino acid 542 (inclusive)(amino acid residues 317-542 of SEQ ID NO: 5).

The calculated average molecular mass of Env-SU is equal to 32061.59. Its estimated pI is equal to 9.61. Its amino acid composition is as follows:

| Nonpolar amino acids: | | |
| --- | --- | --- |
| | Number | Percentage |
| A | 9 | 3.14 |
| V | 16 | 5.57 |
| L | 25 | 8.71 |
| I | 13 | 4.53 |
| P | 21 | 7.32 |
| M | 7 | 2.44 |
| F | 11 | 3.83 |
| W | 6 | 2.09 |

| Polar amino acids: | | |
|---|---|---|
| | Number | Percentage |
| G | 16 | 5.57 |
| S | 31 | 10.80 |
| T | 34 | 11.85 |
| C | 12 | 4.18 |
| Y | 10 | 3.48 |
| N | 18 | 6.27 |
| Q | 9 | 3.14 |

| Acidic amino acids: | | |
|---|---|---|
| | Number | Percentage |
| D | 4 | 1.39 |
| E | 10 | 3.48 |

| Basic amino acids: | | |
|---|---|---|
| | Number | Percentage |
| K | 9 | 3.14 |
| R | 12 | 4.18 |
| H | 14 | 4.88 |

Figure 2:
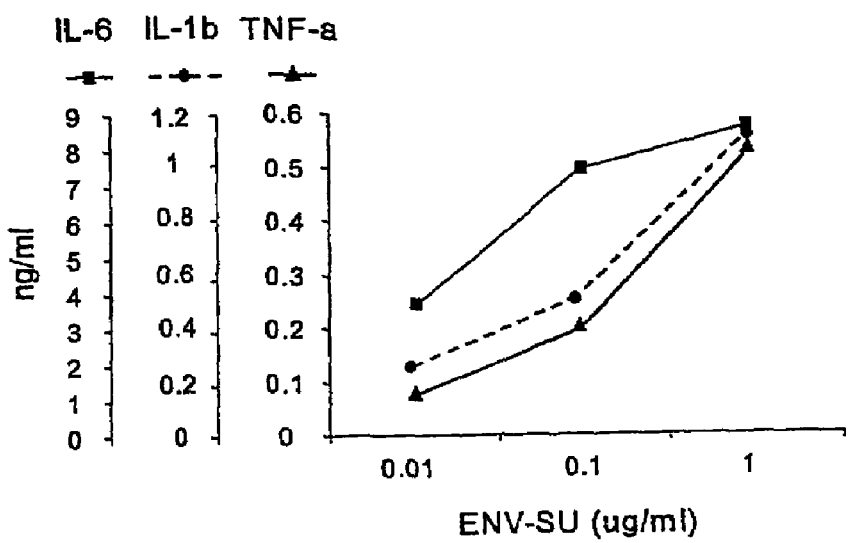
Figure 2:
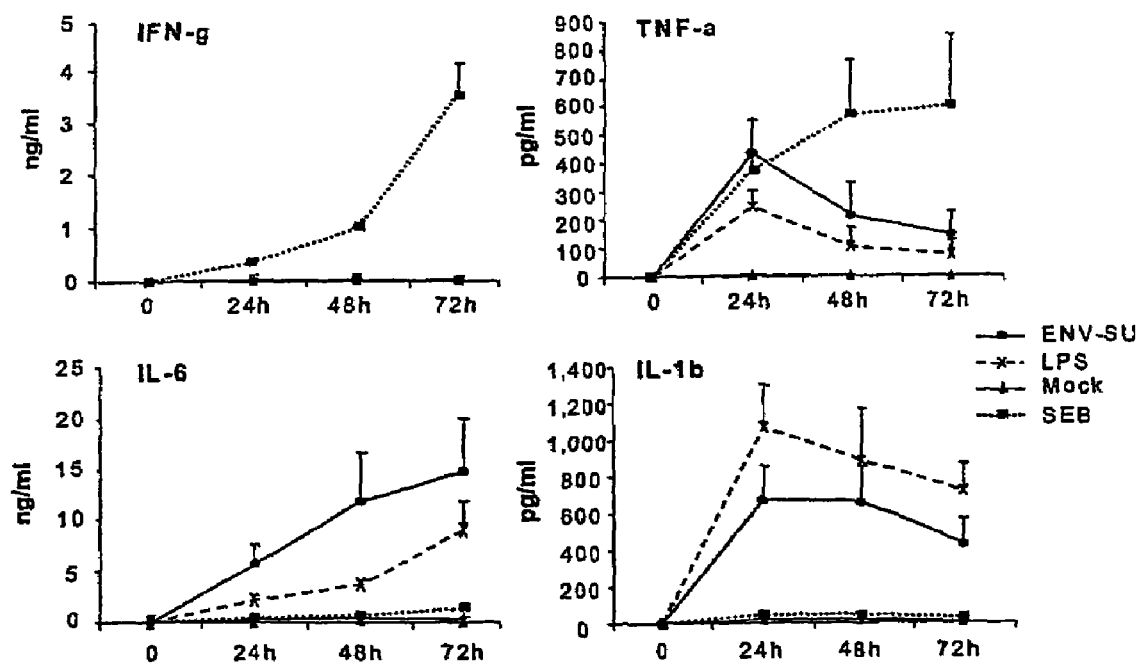

FIG. 2: Env-SU induces the production of pro-inflammatory cytokines in cultures of human PBMCs (mononuclear cells). FIG. 2A represents the secretion of TNF-α, IL-1β and IL-6, analyzed by ELISA assay (enzyme-linked immunosorbent assay) of the culture supernatants of PBMCs from normal donors, stimulated for 24 hours with increasing doses of Env-SU. The results correspond to three independent experiments. The doses of Env-SU are represented along the x-axis (in μg/ml). The y-axis corresponds to the amounts of cytokines (in ng/ml). In the curves, the symbol ■ corresponds to the secretion of IL-6, the symbol ● corresponds to the secretion of IL-1β and the symbol ▲ corresponds to the secretion of TNF-α. In FIG. 1 B, the PBMCs were stimulated with 1 μg/ml of autologous control, of Env-SU, of LPS or of SEB and incubated for 24, 48 and 72 hours before analysis of the cytokine secretion by ELISA. The x-axes correspond to the time in hours and the y-axes correspond to the production of cytokines IFNγ, TNFα, IL-6 and IL-1β in ng/ml for IFNγ and IL-6 (FIGS. 1B (a) and 1B (c)) and in pg/ml for TNFα and IL-1β (FIGS. 1B (b) and 1B (d)). In this figure, -●- corresponds to Env-SU, --x-- corresponds to LPS, -▲- corresponds to the autologous control and ······■······ corresponds to SEB.

Figure 3:
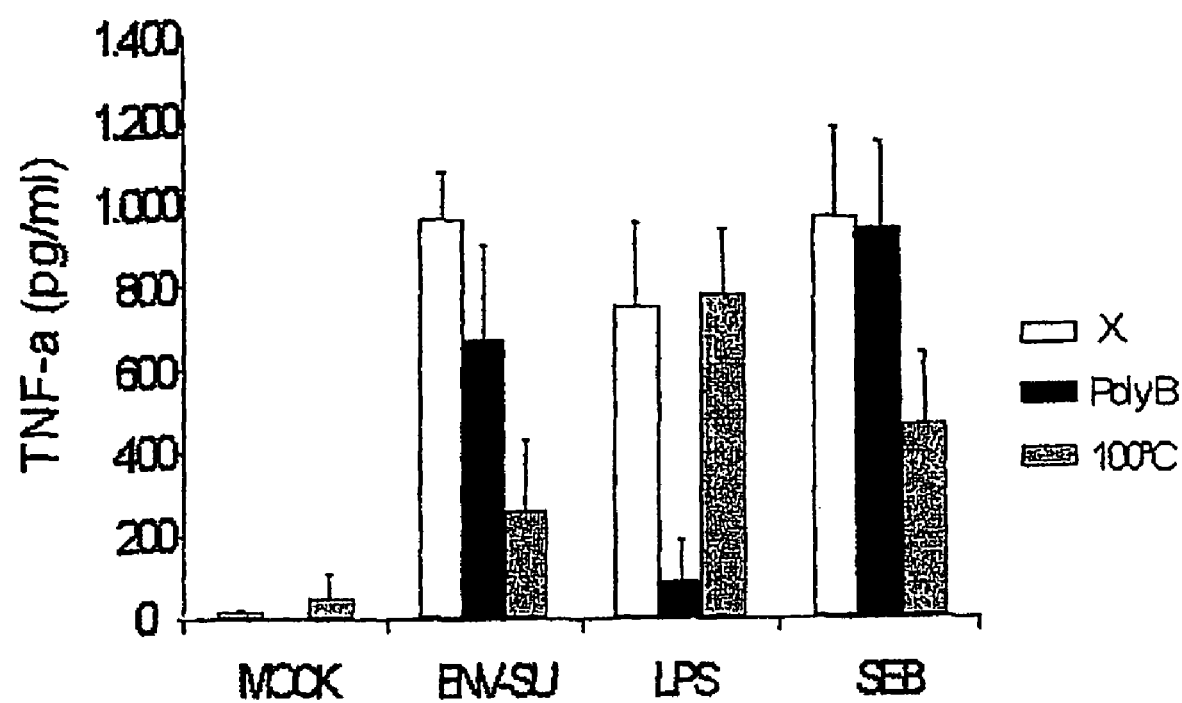

FIG. 3: The cytokine-stimulating activities of Env-SU are not due to a contamination with endotoxins. The PBMCs were stimulated for 24 hours with the autologous control (MOCK), Env-SU, LPS or SEB. When this is indicated, the cells were treated with 10 μg/ml of Polymyxin B (PdyB) before the stimulation (represented in black in the figure). In parallel, the cells were also incubated with proteins and toxins boiled (100° C.) for 30 minutes (represented in gray in the figure). The culture supernatants were harvested and tested for the release of TNF-α by ELISA. The results presented in this figure correspond to the mean of three experiments. The y-axis corresponds to the amounts of TNF-α released, in pg/ml.

Figure 4:
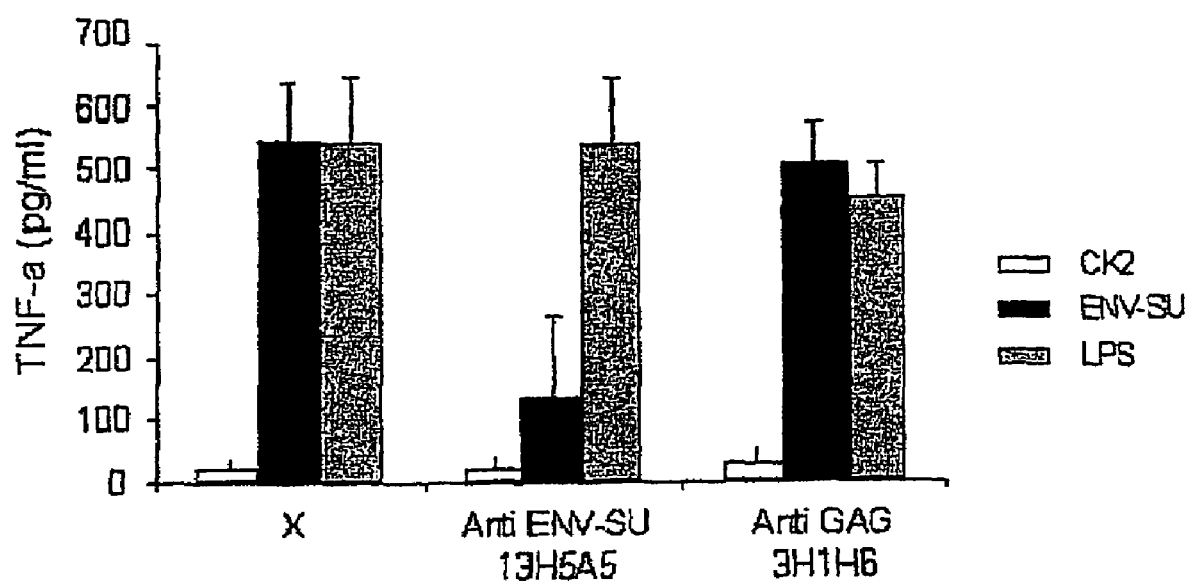

FIG. 4: The anti-Env-SU monoclonal antibody (13H5A5) blocks the cytokine-stimulating activity of Env-SU. The PBMCs were stimulated for 24 hours with 1 μg/ml of the autologous control CK2, Env-SU and LPS and preincubated or not with 30 μg/ml of anti-Env-SU monoclonal antibody and of anti-Gag monoclonal antibody (3H1H6). The culture supernatants were harvested and tested for the secretion of TNF-α. The results presented in this figure correspond to the mean of three experiments. The y-axis corresponds to the amounts of TNF-α released, in pg/ml.

Figure 5:
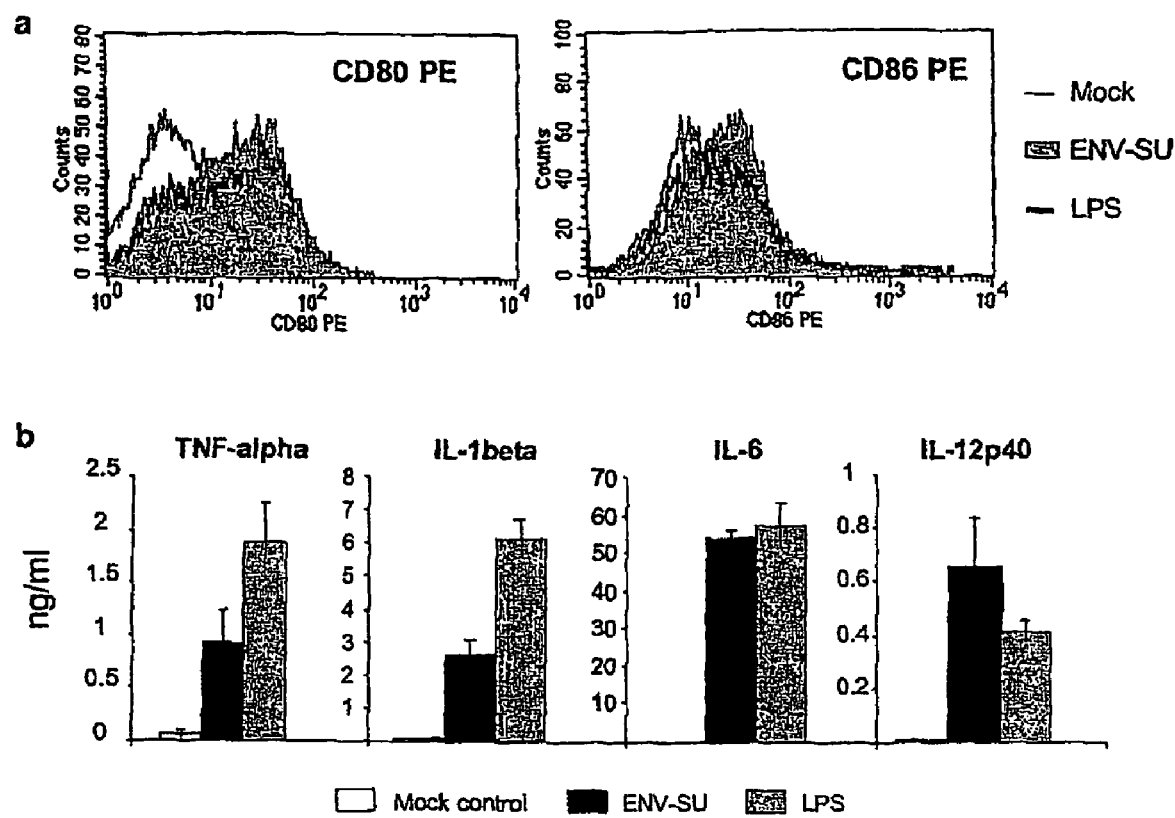

FIG. 5: Env-SU directly activates purified human monocytes. Human monocytes were purified from human PBMCs (purity greater than 95%) and were then stimulated with the autologous control (Mock), Env-SU or LPS, at a concentration of 1 μg/ml, for 24 hours. FIG. 5a represents the expression of the activation markers CD80 (left figure) and CD86 (right figure) analyzed by flow cytometry. Represented along the x-axes is the number of cells counted and along the y-axes is the fluorescence intensity per cell ("counts"). The resultant represents the number of cells counted for each fluorescence intensity. The area defined by the curves represents the total number of cells for each condition tested. The cell distribution as a function of fluorescence intensity is shown by the appearance of the curve. The white area represents the results obtained with the control (Mock), the shaded area, with fine outlines, represents the results obtained with Env-SU and the shaded area with very thick outlines represents the results obtained with the LPS. FIG. 5b represents the secretions of TNF-α, IL-1β, IL-6 and IL-12p40, analyzed by ELISA. Represented in white are the results obtained after stimulation with the autologous control. The results obtained after stimulation with Env-SU and LPS are respectively represented in black and gray. The y-axis corresponds to the amounts of cytokines secreted, in ng/ml. The results represent the mean of three experiments.

Figure 6:
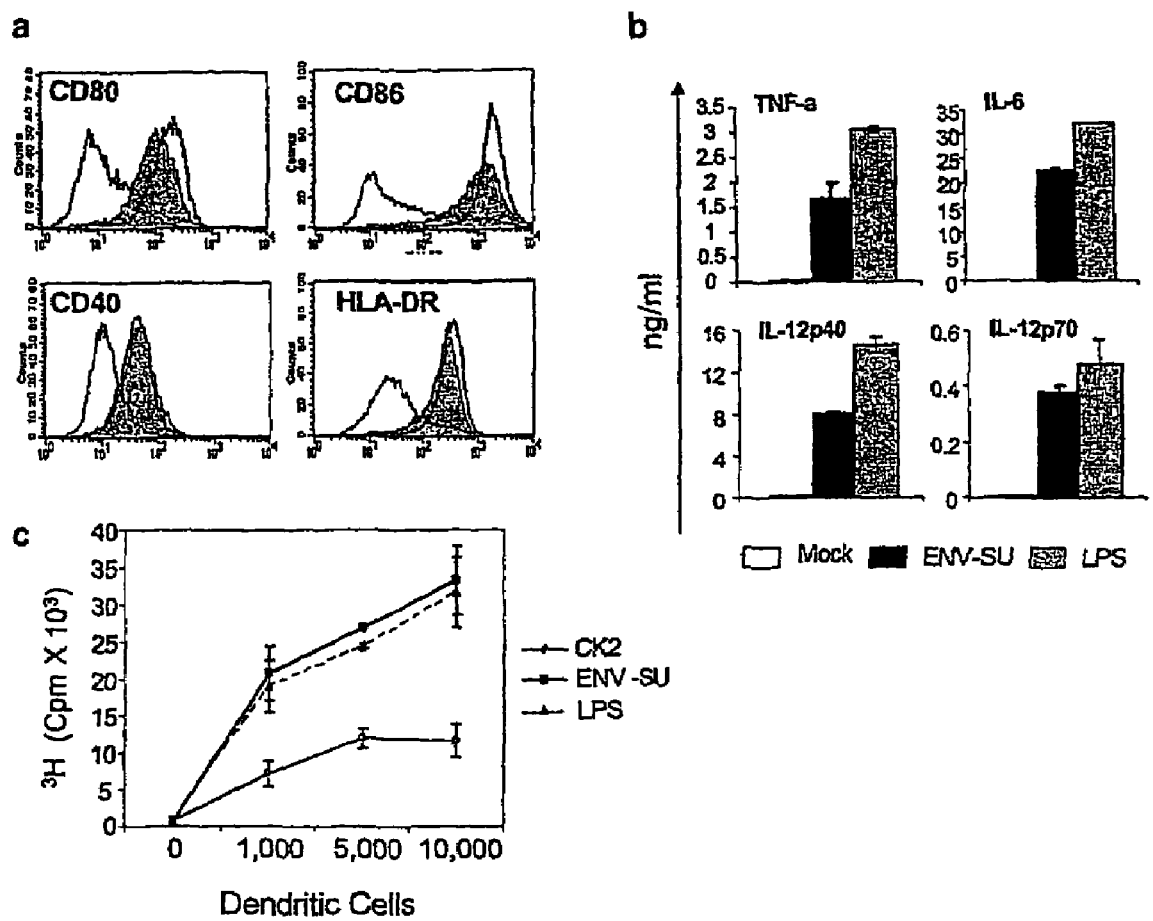

FIG. 6: Env-SU activates monocyte-derived dendritic cells (MDDCs). The MDDCs were generated from purified monocytes and then stimulated with the autologous control, Env-SU or LPS, at a concentration of 1 μg/ml, for 24 hours. FIG. 6a represents the expression of the activation markers CD80, CD86, CD40 and HLA-DR, analyzed by flow cytometry. Represented along the x-axis is the number of cells counted and along the y-axis the fluorescence intensity per cell ("counts"). The top left image represents the analysis of CD80, the top right image that of CD86, the bottom left image represents that of CD40 and the bottom right image that of HLA-DR. The resultant represents the number of cells counted for each fluorescence intensity. The area defined by the curves represents the number of total cells for each condition tested. The cell distribution as a function of fluorescence intensity is shown by the appearance of the curve. The white area to the left represents the results obtained with the control (Mock), the white area to the right, outlined in a thicker line, represents the results obtained with Env-SU and the shaded area represents the results obtained with LPS. FIG. 6b represents the secretion of TNF-α, IL-6, IL-12p40 and IL-12p70, analyzed by ELISA, in the culture supernatants. The y-axis corresponds to the amounts of cytokines secreted, in ng/ml. In the histograms represented in FIG. 6b, Mock corresponds to the results obtained after stimulation with the autologous control, Env-SU (in black) corresponds to the results obtained after stimulation with Env-SU, and LPS (in gray) corresponds to the results obtained after stimulation with LPS. FIG. 6c represents the allogenic proliferation of T cells by dendritic cells stimulated beforehand with: Env-SU -■-, LPS --▲--, control CK2-●-. The x-axis represents the number of dendritic cells (respectively, 0, 1000, 5000 and 10

000). The y-axis represents the number of counts per minute emitted by the cells having incorporated $^3$H-thymidine.

Figure 7:
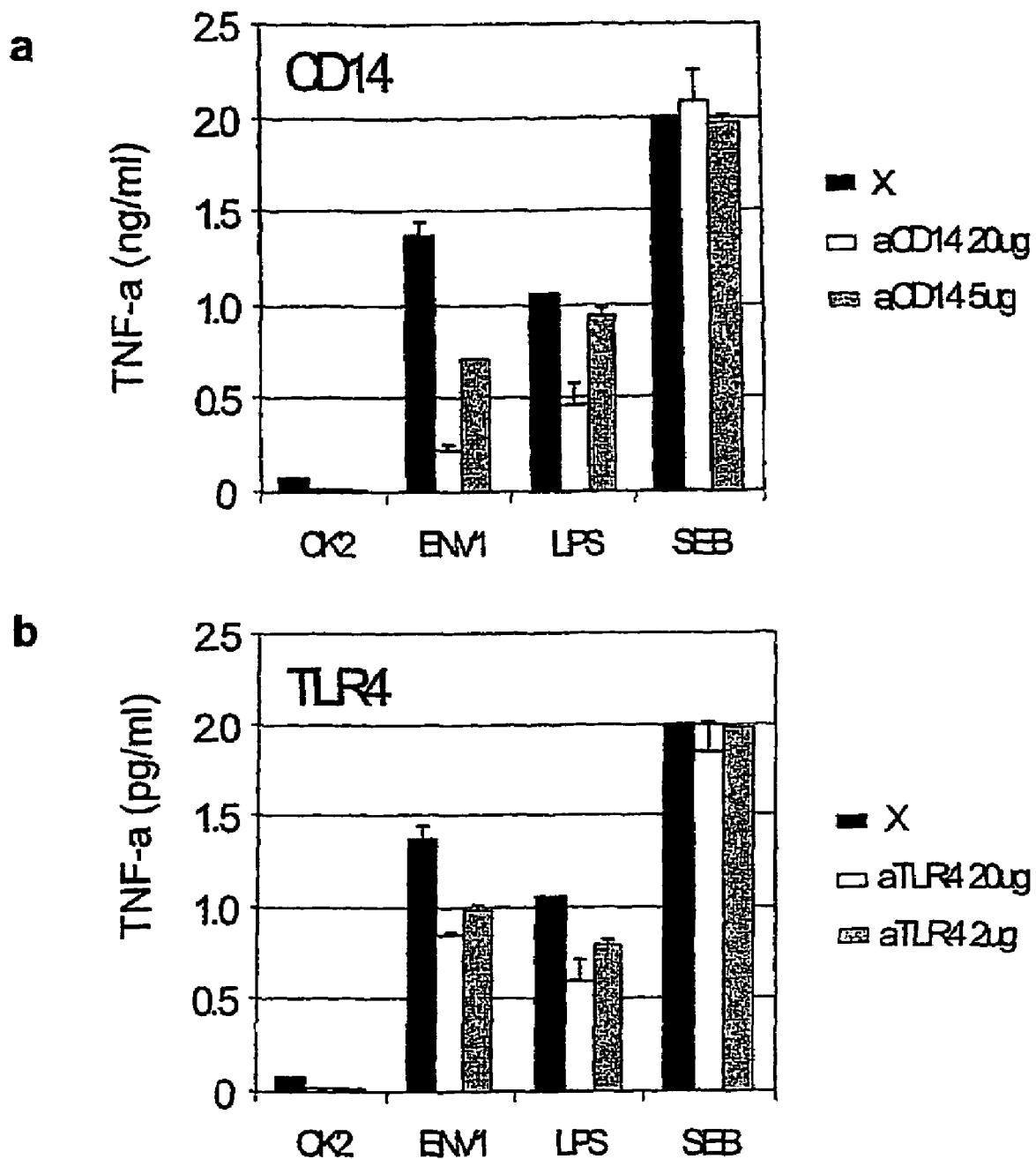

FIG. 7: CD14 and TLR4 are involved in the pro-inflammatory properties of Env-SU. The PBMCs were preincubated for one hour without or with anti-CD14 (rhCD14, ref.: AB383, R&D Systems-UK) (FIG. 7a) and anti-TLR4 (FIG. 7b) neutralizing antibodies, at a concentration of 20 µg/ml and 5 µg/ml. The cells were then stimulated for 24 hours with the CK2 control, Env-SU(ENV1), LPS and SEB, at a concentration of 1 µg/ml. TNF-α release was analyzed, in the culture supernatants, by ELISA. The results are shown in the histograms of FIGS. 7a and 7b. The y-axis corresponds to the amount of TNF-α released, in ng/ml. The histograms in black correspond to the results obtained without the addition of antibodies, the histograms in white correspond to the results obtained in the presence of anti-CD14 and anti-TLR4 antibodies, at 20 µg/ml, and the histograms in gray correspond to the results obtained in the presence of anti-CD14 and anti-TLR4 antibodies at 5 µg/ml. The results correspond to the mean of three experiments.

Figure 8:
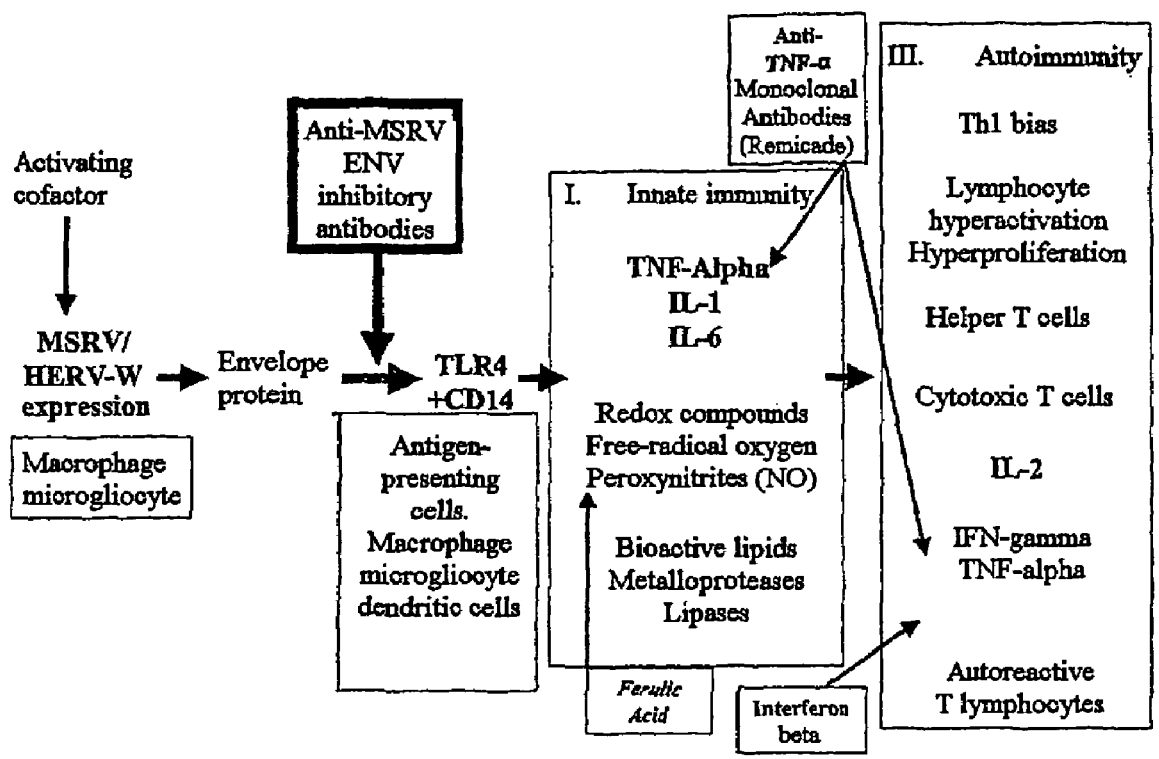

FIG. 8: Immunological amplification cascade subsequent to the activation of the TLR4 pathway. Example of the therapeutic targets in this cascade.

FIG. 8 represents diagrammatically the activation cascade resulting from the pathological expression of an MSRV/HERV-W envelope protein. The latter initially stimulates the TLR4 receptor, possibly associating the CD14 coreceptor. Before this interaction, there is only an agonist, the MSRV-ENV protein. After this activation, the cells of innate immunity are activated and tens of molecular effectors (cytokines, enzymes, lipids, free-radical or redox compounds, etc.) and activated cells come together. In the case of multiple sclerosis, a second component is activated after destruction of the white matter of the brain and presentation of myelin antigens to T lymphocytes, namely the autoimmune component associated with the autoreactive T cells of adaptive immunity. At this stage, hundreds or even thousands of different molecules and cells are involved in mediating the immunopathological effects. This typically gives an immunopathological amplification cascade whose potential bears no resemblance to the initial stimulus (MSRV/HERV-W ENV).

The treatments available or proposed to date target "downstream" of the pro-inflammatory or pathogenic agonists among the numerous other agonists present at the stage of the amplification cascade where they appeared (examples given with anti-TNF-alpha antibodies, interferon beta and a free-radical scavenger molecule such as ferulic acid). In this context, they cannot inhibit the effect of the very large number of other effectors (molecules and cells) which are not sensitive to their pharmacological effect. This explains the partial and relative effect of many current treatments in a disease such as MS.

Furthermore, these treatments do not prevent other cells expressing (under the effect of iterative environmental cofactors, for instance herpesviridae) a pathogenic MSRV/HERV-W copy from producing pro-inflammatory envelope at the same lesional site, or in another cerebral site, at the same time or at a different time (principle of multifocal lesions and relapses/remissions which define MS in terms of the cerebral space and in terms of the evolution time of the disease).

Thus, a treatment which inhibits the initial effect at a stage of the cascade where not all the downstream effectors inducible by the protein-target are produced is much more relevant and has a much greater potential effectiveness than the approaches commonly designed and used in these pathologies associated with the pro-inflammatory effects of this MSRV/HERV-W envelope protein. In fact, even if the cascade is activated, it will be "dried up" upstream by this therapeutic strategy, whereas the upstream stimulation will continue in the other "downstream" therapeutic approaches. Finally, in an approach to prevent further relapses during the periods of remission of the disease, these antibodies can neutralize the "MSRV/HERV-W ENV" proteins before they set off the cascade described here, whereas the other therapies targeting the "downstream" molecules or cells can only intervene after this inflammatory cascade has been triggered into action!

Figure 9:
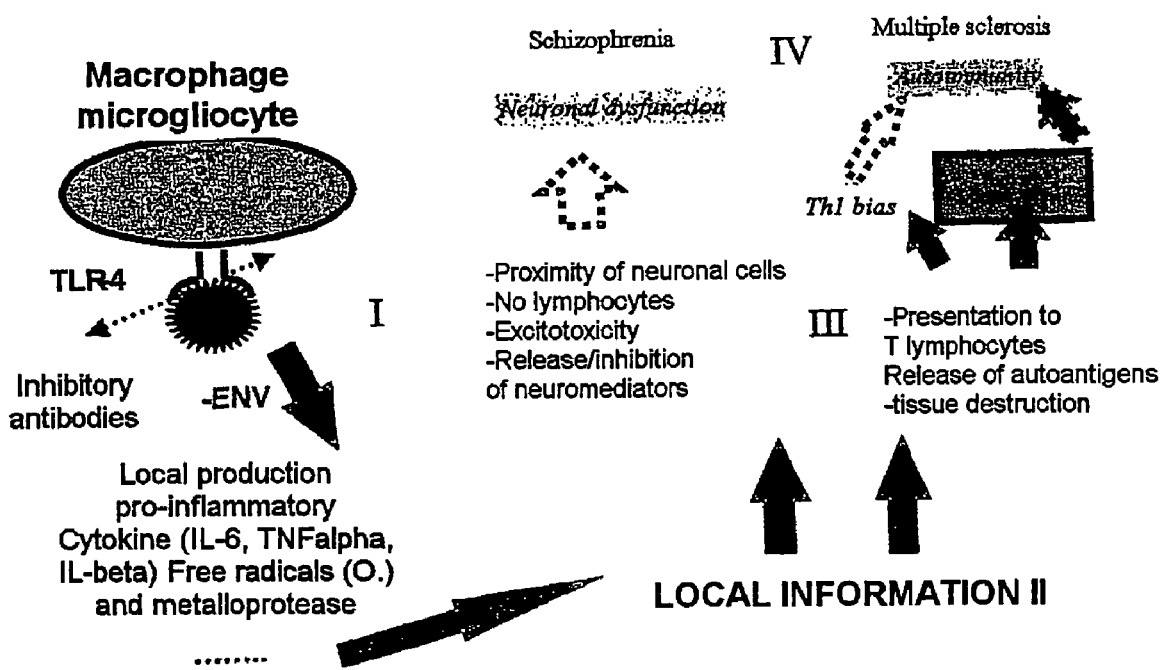

FIG. 9: Four key steps for bringing about two diseases from the pro-inflammatory effect of the MSRV/HERV-W ENV protein:
(i) two common "upstream" steps: I—activation of TLR4 receptors and II—local inflammation,
(ii) two different "downstream" steps: III—neuronal demyelination or excitotoxicity and IV—multiple sclerosis or schizophrenia.

The envelope protein (Env) is produced by a retroviral copy of the MSRV/HERV-W family, in a context of pathological activation such as, for example, after transactivation with an infectious cofactor of the herpesviridae family [46-49] in a tissue region determined by the tropism of this cofactor and by the presence of cells in the target tissue harboring at least one proviral MSRV/HERV-W copy that can be activated by this cofactor and that encodes an envelope protein.

This ENV protein thus produced binds to the TLR4 receptor and, depending on the context, to the TLR4 coreceptors such as CD14, of the macrophage or microgliocyte type cells present in the cerebral tissue in the vicinity of the cell producing MSRV/HERV-W ENV and/or MSRV virions. If the latter cell is a macrophage or a microgliocyte, it is possible that there will be an autocrine effect on the TLR4 receptors of this same cell.

After this step, of interaction with the TLR4 receptor, the immunopathological amplification cascade creates, with the production of tens of pro-inflammatory and tissue destruction-mediating molecules, a local inflammation in the tissue concerned, around the site of MSRV/HERV-W reactivation.

After this stage, the situation diverges according to whether the MSRV/HERV-W reactivation cofactors and the localization of the cells harboring these ",responder" proviruses have converged toward an expression in the white matter or in the gray matter.

In the first case, which determines the pathological pathway resulting in a pathology such as schizophrenia, the induced reactivation or induced overexpression of an MSRV/HERV-W element in the vicinity of the neuronal structures of the frontal cortex induces a local inflammation which, in the gray matter tissue context, will not allow a major pro-lesional activity and a specific immune recruitment. This local inflammation will not allow an infiltration of T lymphocytes at this level. On the other hand, the pro-inflammatory mediators produced in the proximity of the neuronal cells responsible for the "intellectual" and cognitive activities cause a focal neuronal excitotoxicity which determines a dysfunction of the associated neuronal networks in the affected cerebral space and for the period of time during which this pro-inflammatory production occurs [17, 20, 22-26, 29, 50, 51]. Depending on the areas affected, the "psychic" conditions resulting from the excitotoxic neuronal activations are reflected by hallucinatory and delirious manifestations which characterize the clinicopathological attacks of schizophrenia. In the end, it is known that this neuronal excitotoxicity can result in cell death (neurotoxicity), which is objectified by the ventricular enlargement measured by MRI in the brain of patients suffering from schizophrenia [52].

In the second case, which determines the pathological pathway resulting in multiple sclerosis, the myelin in the white matter is extremely sensitive to free-radical and pro-inflammatory agents which generate primary demyelination with the presentation of autoantigens to the lymphocytes recruited by the prior inflammation. Under these conditions, lymphocyte reactivity biases are conditioned by the cytokines secreted beforehand by the microgliocyte/macrophage type cells (Th1 bias), which can be sufficient to generate an autoimmune response in the face of "self" antigens presented under these conditions. However, in addition, it has been shown that the whole MSRV envelope protein or the MSRV virions can exercise a different activity on T lymphocytes, namely a superantigenic activity characterized by an interaction with the "TCR" receptor. The latter property, in this "downstream" context where T lymphocytes recruited by the primary inflammation infiltrate the tissue, ultimately adds a polyclonal activation of the T lymphocytes which even further promotes the specific autoimmune T lymphocyte response to the myelin antigens exposed in the tissue damaged beforehand by the primary inflammation. In this context, a second dimension of the immunopathological reaction then occurs with the effects of the autoimmunity and of the inflammation mediated by the activated T lymphocytes.

Figure 10:
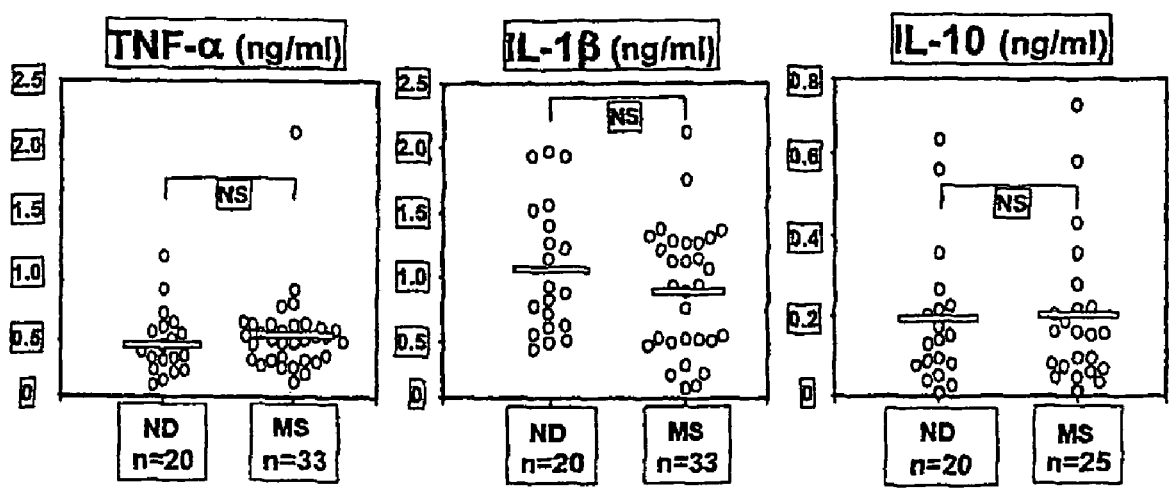

FIG. 10: Production of cytokines induced by ENV-SU on PBMCs from patients suffering from multiple sclerosis (MS) and from normal donors (ND): TNF-alpha, IL-1beta and IL-10

FIG. 10 represents the cytokine production induced by the MSRV ENV-SU protein in the blood mononuclear cells (PB-MCs) taken ex vivo, firstly, from patients suffering from multiple sclerosis (MS) and, secondly, from normal donors (ND). The indication "n=" next to ND or to MS gives the number of individuals tested for each population with respect to the cytokine represented.

The x-axis represents the dosage of the cytokines in the stimulated PBMC culture supernatant in ng/ml. Each graph compares the results for each individual tested, represented by a point (circle) in each population (ND and MS). The three graphs represent, from left to right, the production of tumor necrosis factor (TNF)-alpha, of interleukin(IL)-1beta and of interleukin(IL)-10. As was calculated, the results compared between the ND and MS populations are not significantly different for these three cytokines (not significant, NS). The statistical analysis was carried out with the Student's t test.

Figure 11:
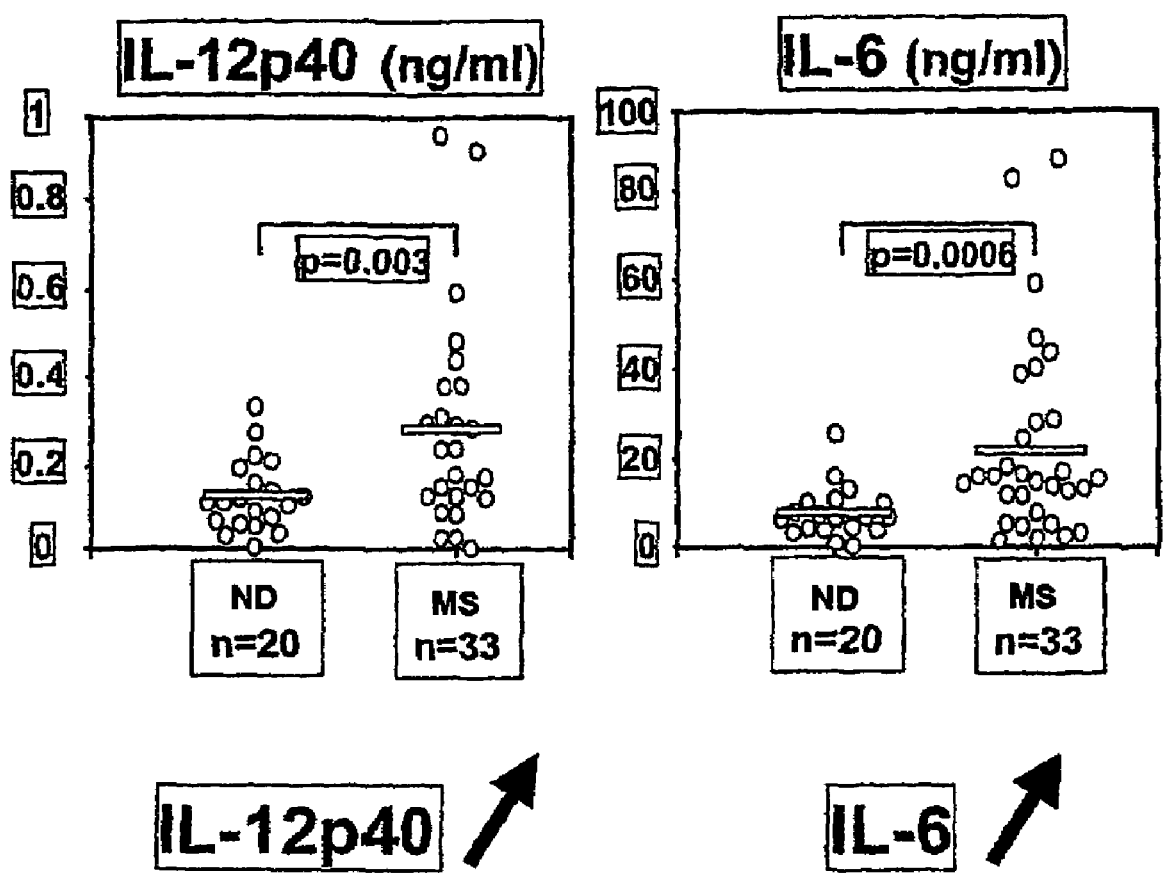

FIG. 11: Production of cytokines induced by ENV-SU on PBMCs from patients suffering from multiple sclerosis (MS) and from normal donors (ND): IL-12p40 and IL-6

FIG. 11 represents the cytokine production induced by the MSRV ENV-SU protein in the blood mononuclear cells (PB-MCs) taken ex vivo, firstly, from patients suffering from multiple sclerosis (MS) and, secondly, from normal donors (ND). The indication "n=" next to ND or to MS gives the number of individuals tested for each population with respect to the cytokine represented.

The x-axis represents the dosage of the cytokines in the stimulated PBMC culture supernatant in ng/ml. Each graph compares the results for each individual tested, represented by a point (circle) in each population (ND and MS). The two graphs represent, from left to right, the production of interleukin (IL)-12p40 and of interleukin(IL)-6. As was calculated, the results compared between the ND and MS populations are very significantly higher in the MS population for these two cytokines (p=0.003 for IL-12p40 and p=0.0006 for IL-6). The statistical analysis was carried out with the Student's t test.

Figure 12:
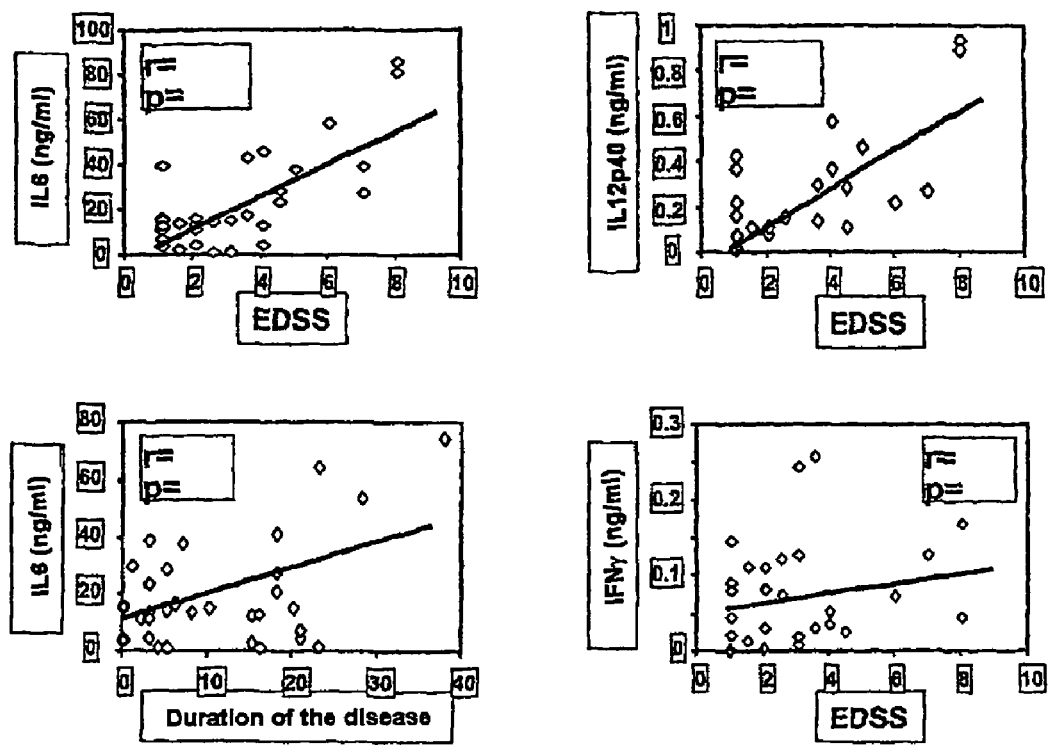

FIG. 12: Correlations between the cytokine productions and the clinical parameters of the patients FIG. 12 represents the graphic results of the analysis of correlation between clinical parameters of the MS population studied (along the x-axis) and the amounts of certain cytokines (along the y-axis) produced in response to the stimulation of their PBMCs by the MSRV-SU ENV protein. For each graph, the value of "r" represents the statistical calculation of the point distribution relative to the correlation line. The value of "p" represents the statistical probability that this correlation is obtained randomly; thus, any value of p greater than 0.05 is "nonsignificant" and any value less than 0.05 signifies an existing correlation between the factors analyzed.

The two top graphs show the parameters which were found with a significant correlation between the clinical score of the MS patients, EDSS [53] measured on a severity scale of 1 to 10, and IL-6 (on the left) or IL12p40 (on the right).

The two bottom graphs show two examples of parameters which were not found to be significantly correlative: the duration of the disease and IL-6 (on the left), or gamma interferon and the clinical score EDSS (on the right).

Figure 13:
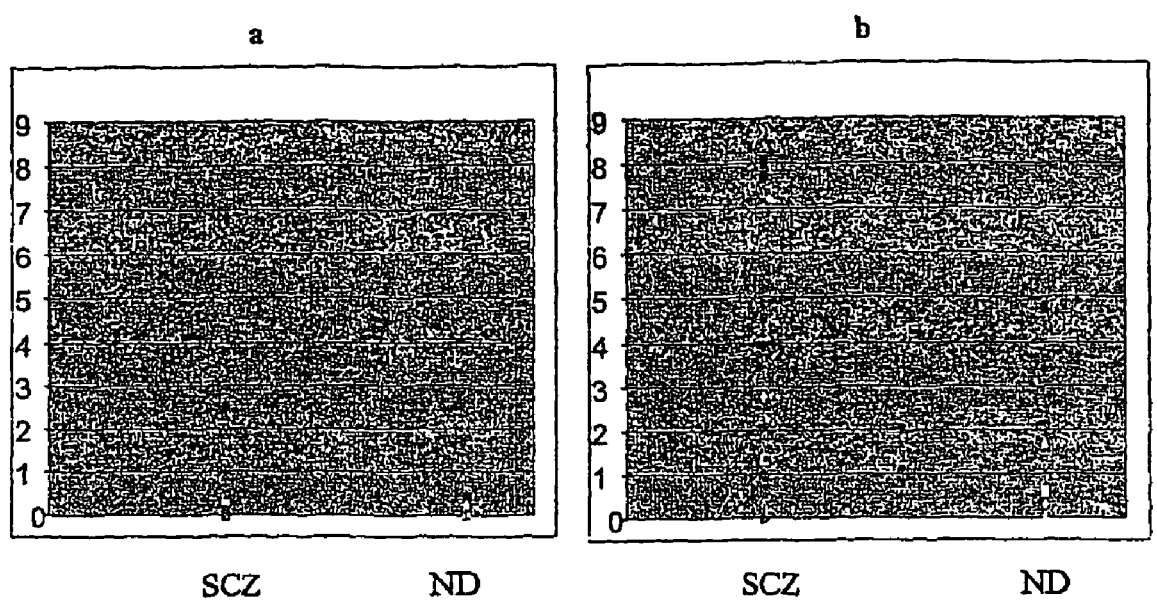

FIG. 13: Spontaneous production (a) or ENV-SU-induced production (b) of cytokines in PBMCs from patients suffering from schizophrenia (SCZ) and from normal donors (ND): IL-10.

FIG. 13 represents the cytokine production induced by the MSRV ENV-SU protein in the blood mononuclear cells (PB-MCs) taken ex vivo, firstly, from patients suffering from schizophrenia (SCZ) and, secondly, from normal donors (ND).

The x-axis represents the dosage of the cytokines in the stimulated PBMC culture supernatant in ng/ml. Each graph compares the results for each individual tested, represented by a point in each population (ND and MS). The two graphs represent, from left to right, the spontaneous production of interleukin (IL)-10 in culture and the production of interleukin(IL)-10 induced after stimulation with ENV-SU.

Figure 14:
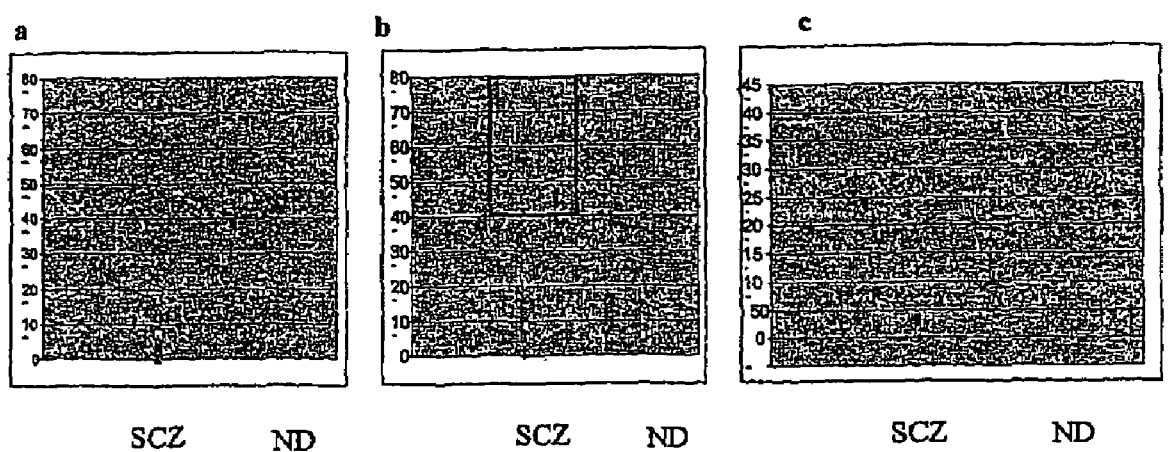

FIG. 14: Spontaneous production (a) or ENV-SU induced production (b) of cytokines in PBMCS from patients suffering from schizophrenia (SCZ) and from normal donors (ND), with calculation of the relative increase (c): IL-12p40.

FIG. 14 represents the cytokine production induced by the MSRV ENV-SU protein in the blood mononuclear cells (PB-MCs) taken ex vivo, firstly, from patients suffering from schizophrenia (SCZ) and, secondly, from normal donors (ND).

The x-axis represents the dosage of the cytokines in the stimulated PBMC culture supernatant in ng/ml. Each graph compares the results for each individual test, represented by a point in each population (ND and MS). The three graphs represent, from left to right: a) the spontaneous production of interleukin(IL)-12p40 in culture, b) the production of interleukin(IL)-10 induced after stimulation with ENV-SU and c) the relative increase in production of IL12p40 calculated according to the formula: (amount after ENV-SU stimulation−spontaneous amount)/spontaneous amount.

FIG. 15: Identification and selection of anti-MSRV/HERV-W ENV monoclonal antibodies which inhibit the proinflammatory activation of monocyte-macrophages induced by the ENV-SU protein, in cultures of human PBMCs originating from normal donors. a) Analysis with two anti-ENV antibodies and a control antibody b) verification of the conditions for specificity of the analysis c) example of independent experiment d) d) other example of independent experiment:

FIG. 15a represents, along the y-axis, the secretion of TNF-alpha (ng/ml) induced by (along the x-axis) the "Mock"

control protein (1 microgram/ml), ENV-SU (1 microgram/ml) and LPS (1 microgram/ml), in a culture of PBMCs from a normal donor. From left to right for each stimulation condition: the white bar represents the result in the absence of antibodies, the black bar represents the result in the presence of anti-MSRV ENV antibody 3B2H4 (30 micrograms/ml), the hashed bar represents the result in the presence of anti-MSRV ENV antibody 13H5A5 (30 micrograms/ml) and the shaded bar represents the result in the presence of anti-MSRV GAG antibody 3H1H6 (30 micrograms/ml).

FIG. 15b represents, along the y-axis, the secretion of TNF-alpha (ng/ml) induced by (along the x-axis) the "Mock" control protein (1 microgram/ml), ENV-SU (1 microgram/ml) and LPS (1 microgram/ml), in a culture of PBMCs from the same normal donor as in 15a. From left to right for each stimulation condition: the white bar represents the result in the absence of antibodies, the black bar represents the result in the presence of polymyxin B (25 micrograms/ml) and the shaded bar represents the result obtained with MOCK, ENV-SU or LPS heated at 100° C. for 30 minutes, prior to their addition to the PBMC culture.

Figure 15C:
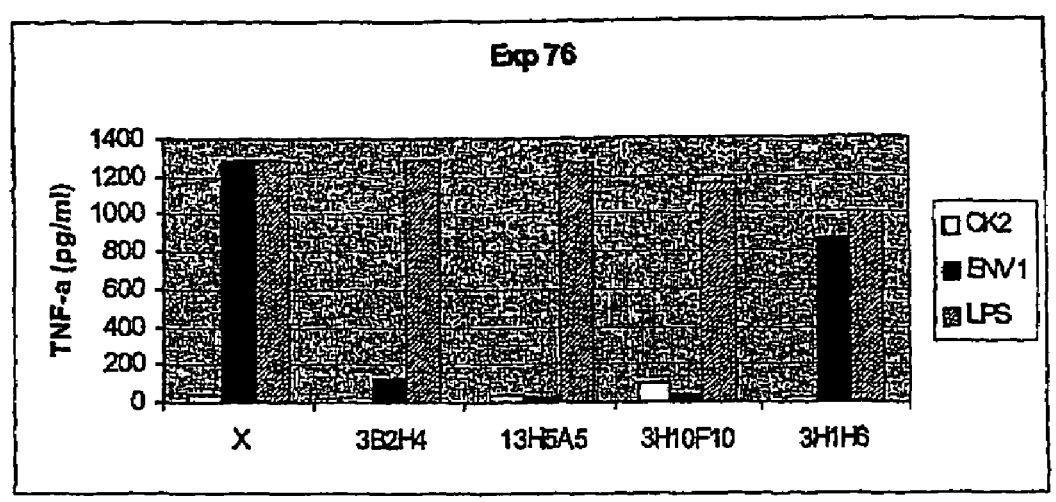

FIG. 15c represents, along the y-axis, the secretion of TNF-alpha (pg/ml) induced by the "Mock" control protein illustrated by a white bar (1 microgram/ml), ENV-SU illustrated by a black bar (1 microgram/ml) and LPS illustrated by a hatched bar (1 microgram/ml), in a culture of PBMCs from a normal donor. From left to right for each stimulation condition, the results are given for the antibodies indicated along the x-axis: anti-toxoplasma antibody "X" of the same isotype as 3B2H4 (30 micrograms/ml), anti-MSRV ENV antibody 3B2H4 (30 micrograms/ml), anti-MSRV ENV antibody 13H5A5 (30 micrograms/ml), anti-MSRV ENV antibody 3H10F10 (30 micrograms/ml), anti-MSRV GAG antibody 3H1H6 (30 micrograms/ml).

Figure 15D:
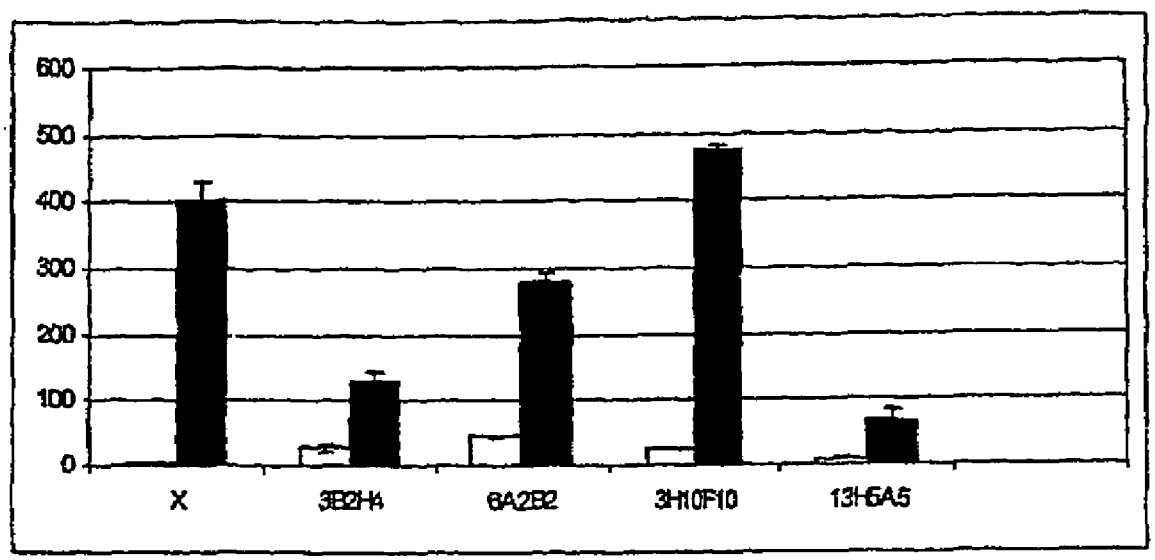

FIG. 15d represents, along the y-axis, the secretion of TNF-alpha (pg/ml) induced by the "Mock CK2" control protein illustrated by a white bar (1 microgram/ml) and ENV-SU illustrated by a black bar (1 microgram/ml), in a culture of PBMCs from a normal donor. From left to right for each stimulation condition, the results are given for the antibodies indicated along the x-axis: anti-toxoplasma antibody "X" of the same isotype as 3B2H4 (30 micrograms/ml), anti-MSRV ENV antibody 3B2H4 (30 micrograms/ml), anti-MSRV ENV antibody 6A2B2 (30 micrograms/ml), anti-MSRV EV antibody 3H10F10 (30 micrograms/ml) and anti-MSRV ENV antibody 13H5A5 (30 micrograms/ml).

Figure 16:
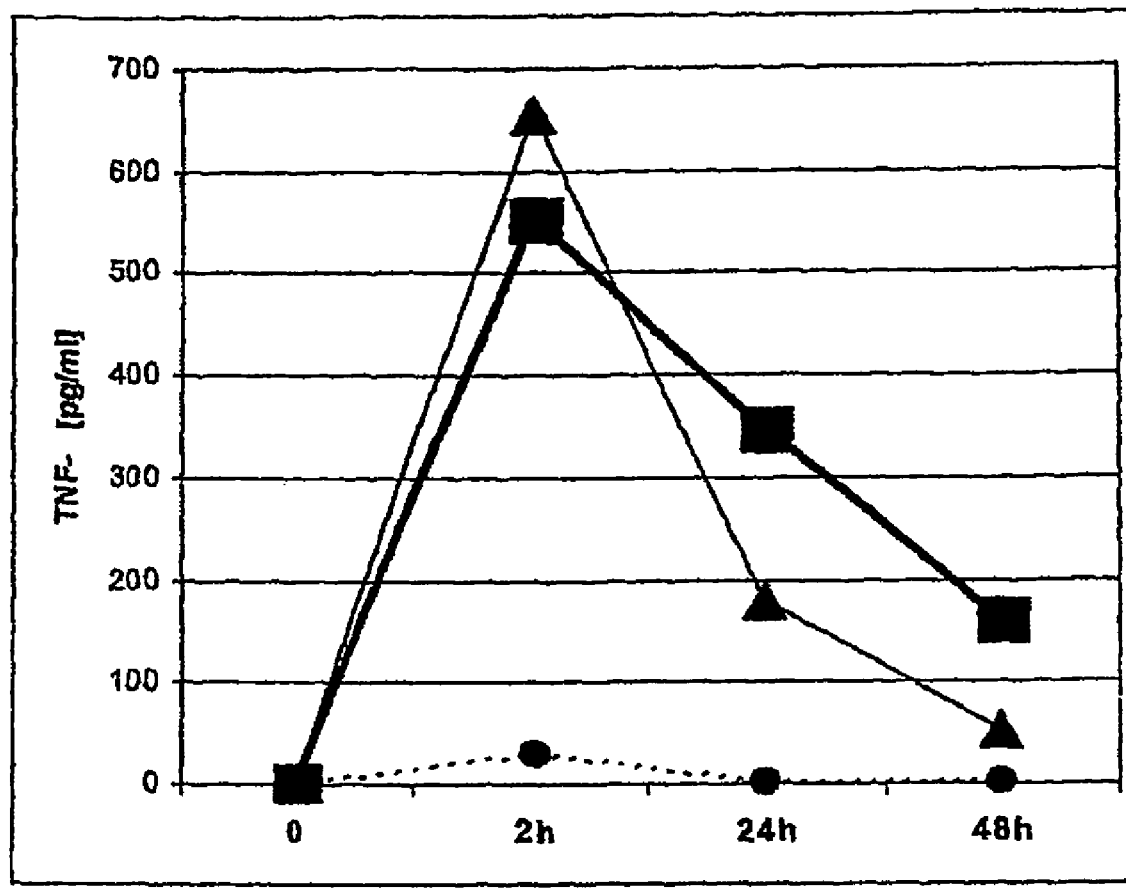

FIG. 16: Kinetics of TNF-α production on PBMCs

PBMCs from normal donors were stimulated with 5☐1 of buffer (curve with dashed lines and circles) 1 ☐g/ml of ENV-SU (curve in a thick line with squares) or 1 ☐g/ml of LPS (curve in a thin line with triangles) and incubated for 2 h, 24 h or 48 h α-axis), before analysis of the production of TNF-α by ELISA (y-axis in pg/ml).

Figure 17:
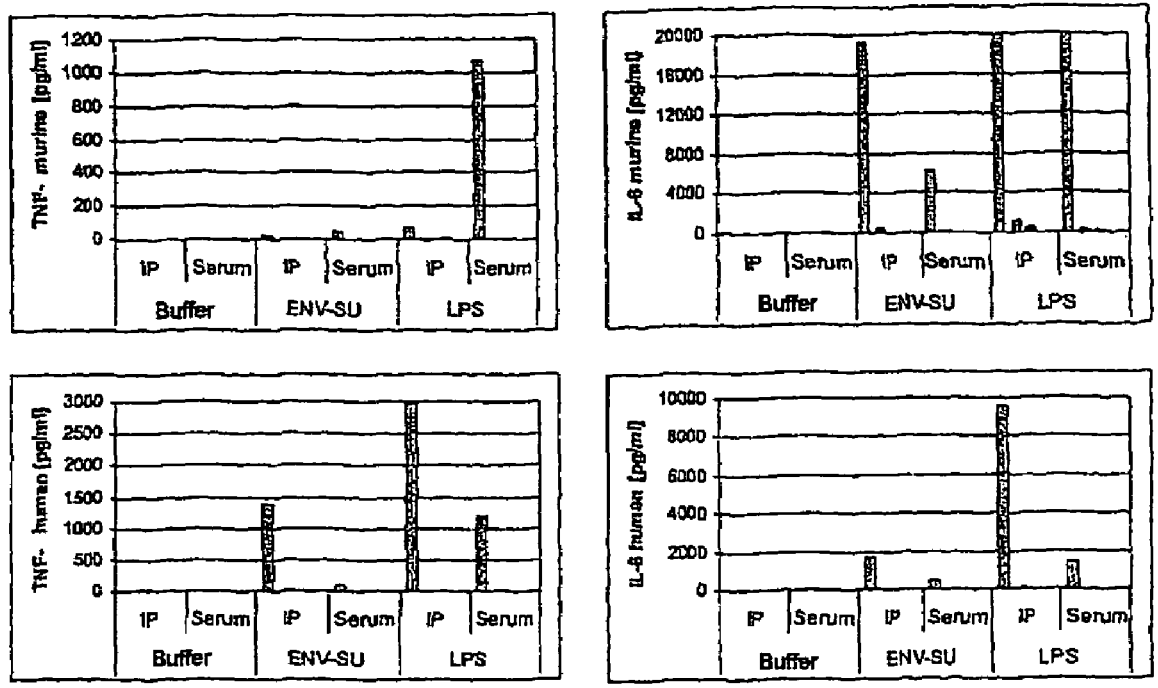

FIG. 17: Pro-inflammatory effects of ENV-SU in humanized SCID.

SCID mice weighing approximately 25 g were given, as indicated along the x-axis, injections of buffer, of 50 ☐g of ENV-SU per animal or of 50 ☐g of LPS per animal. As also indicated along the x-axis for each type of inoculum, the serum or the liquid derived from peritoneal lavage (IP) of the mice sacrificed at 2 h, 24 h and 48 h were analyzed by ELISA.

The graphs on the left represent the dosage of TNF-alpha (pg/ml). The top one represents the dosage of the murine cytokine and the bottom one represents that of the human cytokine.

The graphs on the right represent the dosage of IL-6 (pg/ml). The top one represents the dosage of the murine cytokine and the bottom one represents that of the human cytokine.

Figure 18:
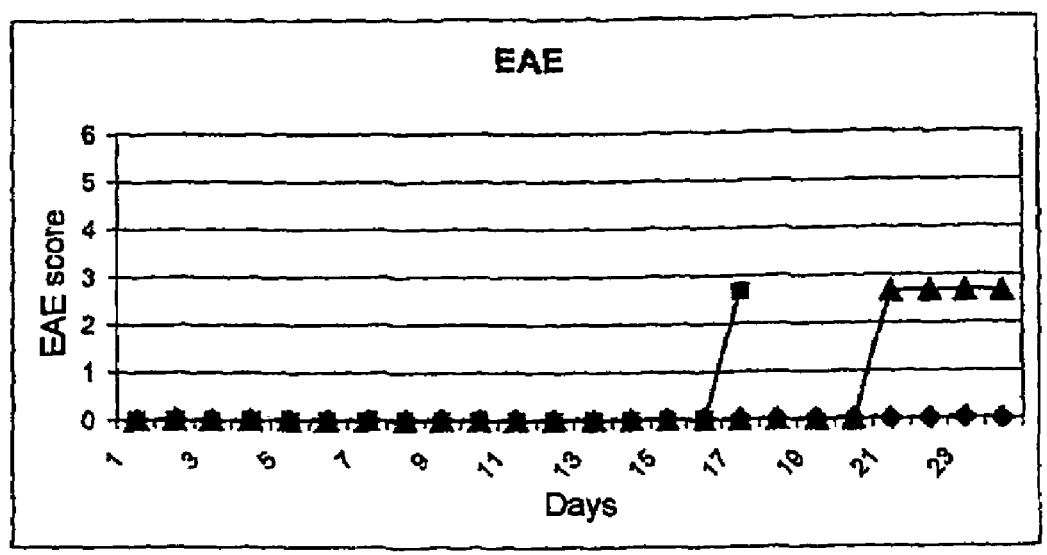

FIG. 18: Induction of EAE with the MSRV ENV protein

FIG. 18 represents the results of a preliminary experiment consisting of induction of EAE with the MSRV ENV protein in C57B16 mice.

The x-axis represents the days after injection. The y-axis represents the average clinical score of the animals studied.

The curve with the squares represents the positive control animals injected with the MOG (myelin oligodendrocyte glycoprotein) autoantigen and complete Freund's adjuvant (containing the extract of *Mycobacterium tuberculosis*). The study of this series was finalized in this case at 18 days.

The curve with the triangles represents the animals injected with the MOG (myelin oligodendrocyte glycoprotein) autoantigen, incomplete Freund's adjuvant (not containing the extract of *M. tuberculosis*) and the MSRV ENV-SU protein. The study of this series was continued in this case up to 25 days.

The curve with the diamonds represents the negative control animals injected with the MOG (myelin oligodendrocyte glycoprotein) autoantigen and incomplete Freund's adjuvant (not containing the extract of *M. tuberculosis*). The study of this series was continued in this case up to 25 days.

Figure 19:
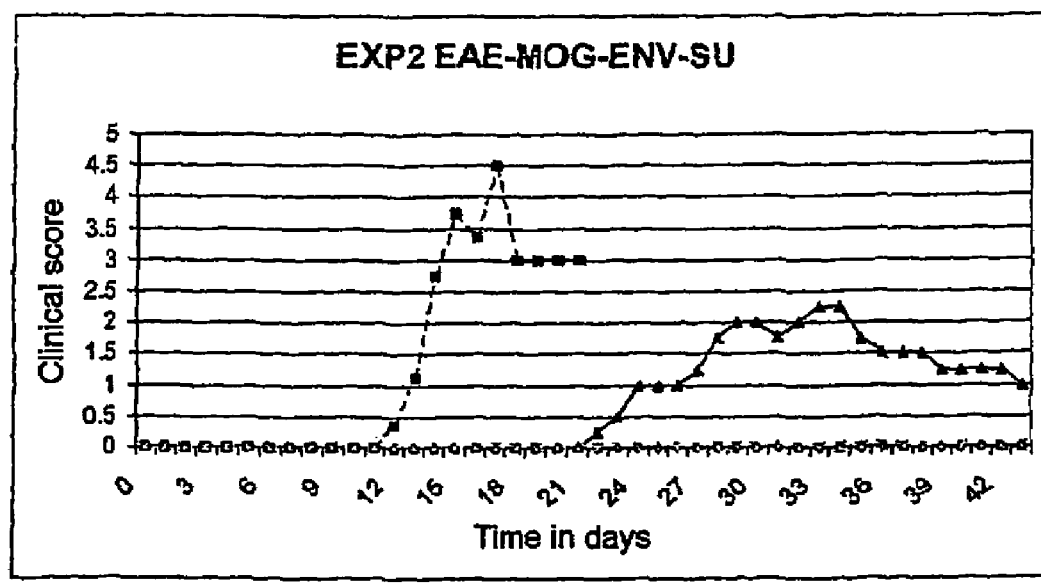

FIG. 19: Reproduction of the induction of EAE with the MSRV ENV protein

FIG. 19 represents the results of an experiment confirming the induction of EAE with the MSRV ENV protein in C57B16 mice.

The x-axis represents the days after injection. The y-axis represents the average clinical score of the animals studied.

The curve with the squares represents the positive control animals injected with the MOG (myelin oligodendrocyte glycoprotein) autoantigen and complete Freund's adjuvant (containing the extract of *Mycobacterium tuberculosis*). The study of this series was finalized in this case at 21 days.

The curve with the triangles represents the animals injected with the MOG (myelin oligodendrocyte glycoprotein) autoantigen, incomplete Freund's adjuvant (not containing the extract of *M. tuberculosis*) and the MSRV ENV-SU protein. The study of this series was continued in this case up to 42 days.

The curve with the diamonds represents the negative control animals injected with the MOG (myelin oligodendrocyte glycoprotein) autoantigen and incomplete Freund's adjuvant (not containing the extract of *M. tuberculosis*). The study of this series was continued in this case up to 42 days.

The curve with the crosses represents the negative control animals injected with the MOG (myelin oligodendrocyte glycoprotein) autoantigen, incomplete Freund's adjuvant (not containing the extract of *M. tuberculosis*) and LPS. The study of this series was continued in this case up to 42 days.

Figure 20:
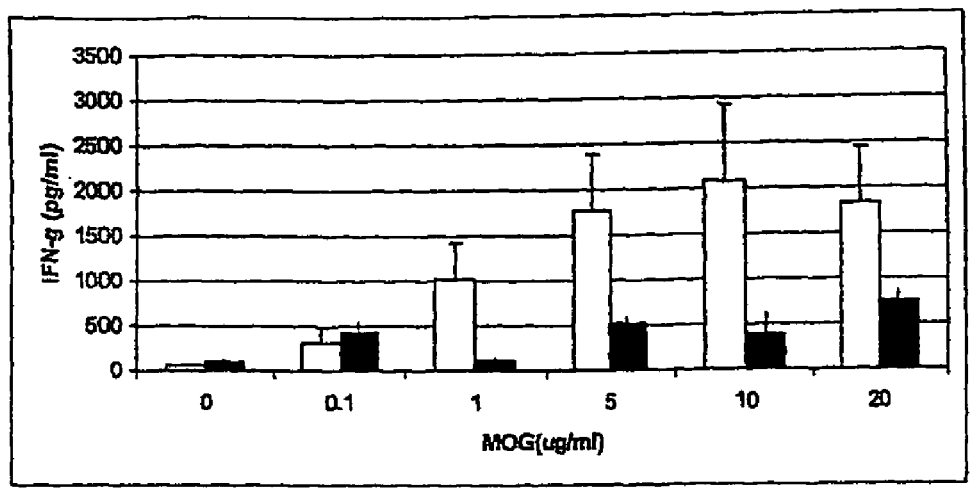

FIG. 20: Assay at 24 h of the autoimmune response to increasing doses of MOG autoantigen in mice of the "EAE/MOG/ENV-SU" model and in the control immunized without ENV.

The x-axis represents the concentrations of MOG autoantigen (microgram/ml) brought into contact with the PBMCs of mice sampled in the course of the protocol illustrated in FIG. 19. The y-axis represents the dosage of interferon gamma secreted in vitro by the autoimmune T lymphocytes present in the PBMCs brought into contact with increasing doses of MOG antigen.

The white bars represent the PBMCs from mice having been given an in vivo injection (at day "0" of the series illustrated in FIG. 19) of the MOG (myelin oligodendrocyte glycoprotein) autoantigen, incomplete Freund's adjuvant (not containing the extract of *M. tuberculosis*) and the MSRV ENV-SU protein.

The black bars represent the PBMCs of control mice having been given an in vivo injection (at day "0" of the series illustrated in FIG. 19) of the MOG (myelin oligodendrocyte glycoprotein) autoantigen and incomplete Freund's adjuvant (not containing the extract of *M. tuberculosis*).

Figure 21:
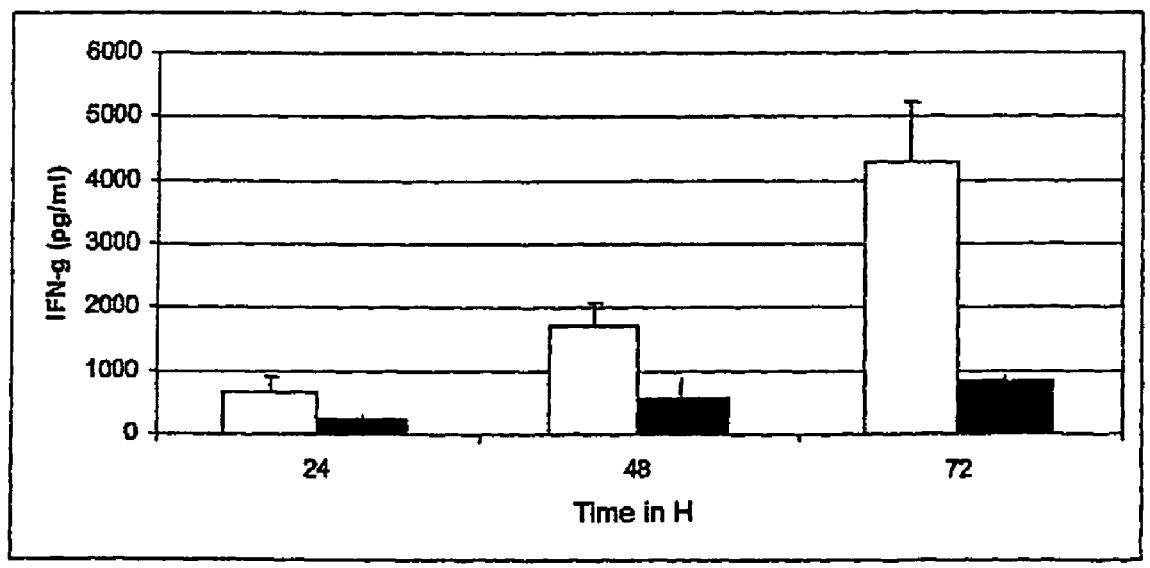

FIG. 21: Kinetics of the anti-MOG autoimmune T lymphocyte response revealed by the secretion of interferon gamma in the mice of the "EAE/MOG/ENV-SU" model and in the control immunized without ENV.

The x-axis represents the period post-inoculation of the "MOG and adjuvants" preparation (in hours) at which the samples of PBMCs are taken from the mice of the series illustrated in FIG. 19. The y-axis represents the dosage of interferon gamma secreted in vitro by the autoimmune T lymphocytes present in the PBMCs.

The white bars represent the PBMCs from mice having been given an in vivo injection (at day "0" of the series illustrated in FIG. 19) of the MOG (myelin oligodendrocyte glycoprotein) autoantigen, incomplete Freund's adjuvant (not containing the extract of *M. tuberculosis*) and the MSRV ENV-SU protein.

The black bars represent the PBMCs from control mice having been given an in vivo injection (at day "0" of the series illustrated in FIG. 19) of the MOG (myelin oligodendrocyte glycoprotein) autoantigen and incomplete Freund's adjuvant (not containing the extract of *M. tuberculosis*).

Figure 22:
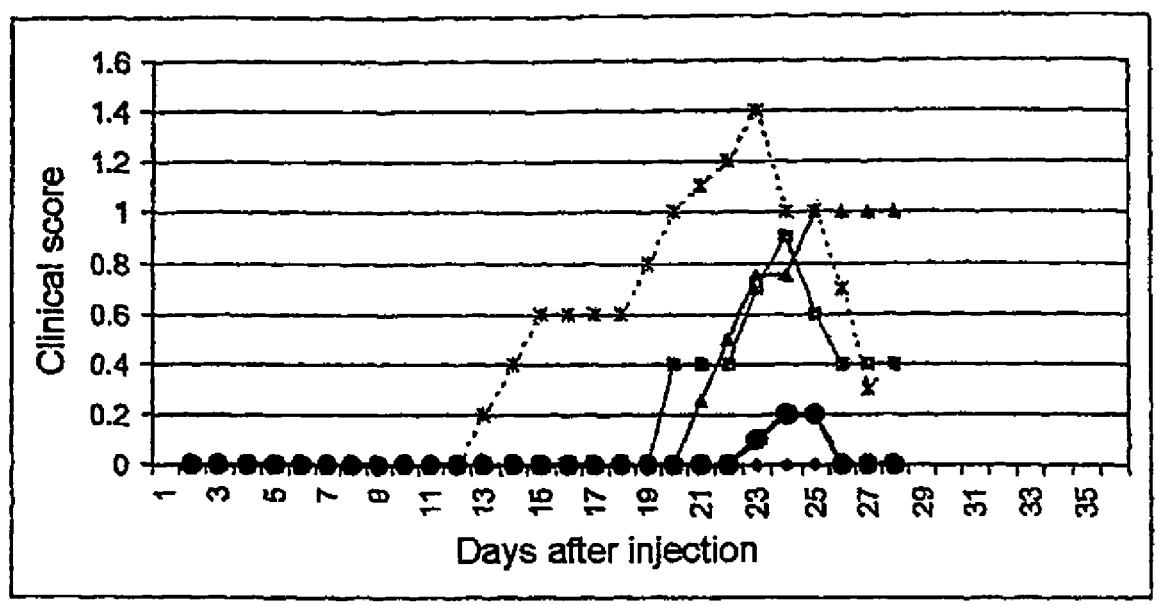

FIG. 22: Therapeutic activity of the anti-MSRV ENV antibodies selected for their inhibitory effect on the pro-inflammatory activation of ENV-SU, demonstrated in an MS model developed and validated in the present invention.

FIG. 22 represents the results of an experiment confirming the induction of EAE with the MSRV ENV protein in C57B16 mice and the inhibitory effect of the monoclonal anti-MSRV/HERV-W ENV antibodies selected beforehand in the assay for inhibition of the pro-inflammatory activity mediated by TLR4, induced by the soluble fragment ENV-SU of the ENV protein.

The x-axis represents the days after injection. The y-axis represents the average clinical score of the animals studied.

The curve with the squares represents the positive control animals injected with the MOG (myelin oligodendrocyte glycoprotein) autoantigen and complete Freund's adjuvant (containing the extract of *Mycobacterium tuberculosis*). The study of this series was finalized in this case at 28 days.

The curve with the triangles represents the animals injected with the MOG (myelin oligodendrocyte glycoprotein) autoantigen, incomplete Freund's adjuvant (not containing the extract of *M. tuberculosis*) and the MSRV ENV-SU protein. The study of this series was continued in this case up to 28 days.

The curve with the diamonds represents the negative control animals injected with the MOG (myelin oligodendrocyte glycoprotein) autoantigen and incomplete Freund's adjuvant (not containing the extract of *M. tuberculosis*). The study of this series was continued in this case up to 28 days.

The curve as a dashed line with the crosses represents the animals injected with the MOG (myelin oligodendrocyte glycoprotein) autoantigen, incomplete Freund's adjuvant (not containing the extract of *M. tuberculosis*) and the MSRV ENV-SU protein. These animals were, in addition, given a dose of 50 micrograms per kilo, i.e. one microgram for a mouse weighing 20 grams, of anti-MSRV GAG control antibody 3H1H6. The study of this series was continued in this case up to 28 days.

The curve with the circles represents the animals injected with the MOG (myelin oligodendrocyte glycoprotein) autoantigen, incomplete Freund's adjuvant (not containing the extract of *M. tuberculosis*) and the MSRV ENV-SU protein. These animals were, in addition, given a dose of 50 micrograms per kilo, i.e. one microgram for a mouse weighing 20 grams, of anti-MSRV ENV control antibody 3B2H4. The study of this series was continued in this case up to 28 days.

Figure 23:
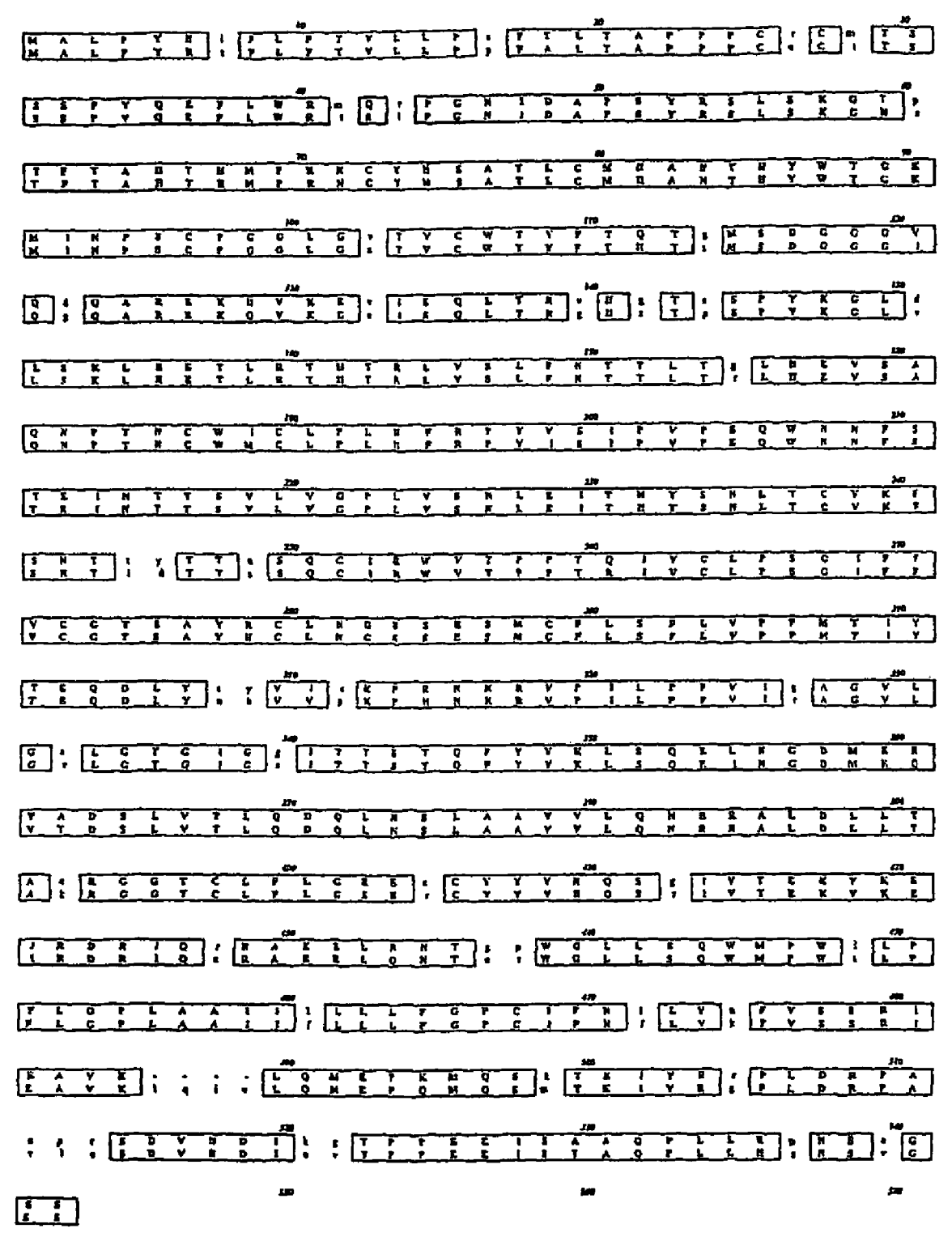

FIG. 23: Amino acid sequences compared between the MSRV ENV protein (lower line) (SEQ ID NO: 5) and the ENV protein encoded by the HERV-W7q copy (upper line) (SEQ ID NO: 4); the sequences boxed in correspond to conserved regions.

Figure 24:
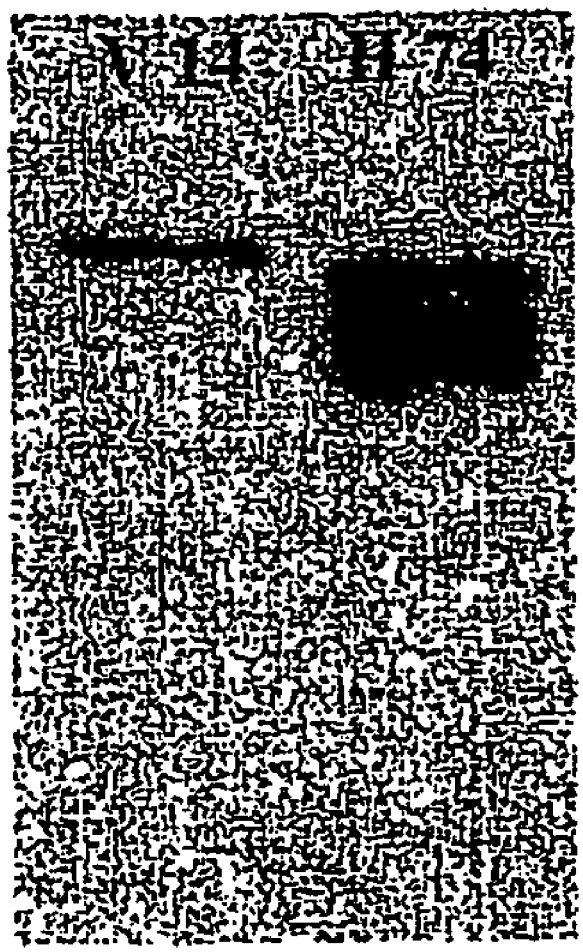

FIG. 24: Western blotting analysis.

Antigenic cross reactivity between the MRSV ENV protein and the ENV protein encoded by the env orf of the HERV-W copy located ubiquitously on the 7q chromosome, V14=ENV recombinant protein encoded by the clone MSRV pV14, H74=ENV recombinant protein encoded by the clone HERV-W7q pH74.

3C1D5: monoclonal antibody obtained after immunization with recombinant proteins derived from MSRV clones.

The arrow shows the level of the bands detected. 60 Kda indicates the level of the corresponding molecular weight.

Figure 25A:
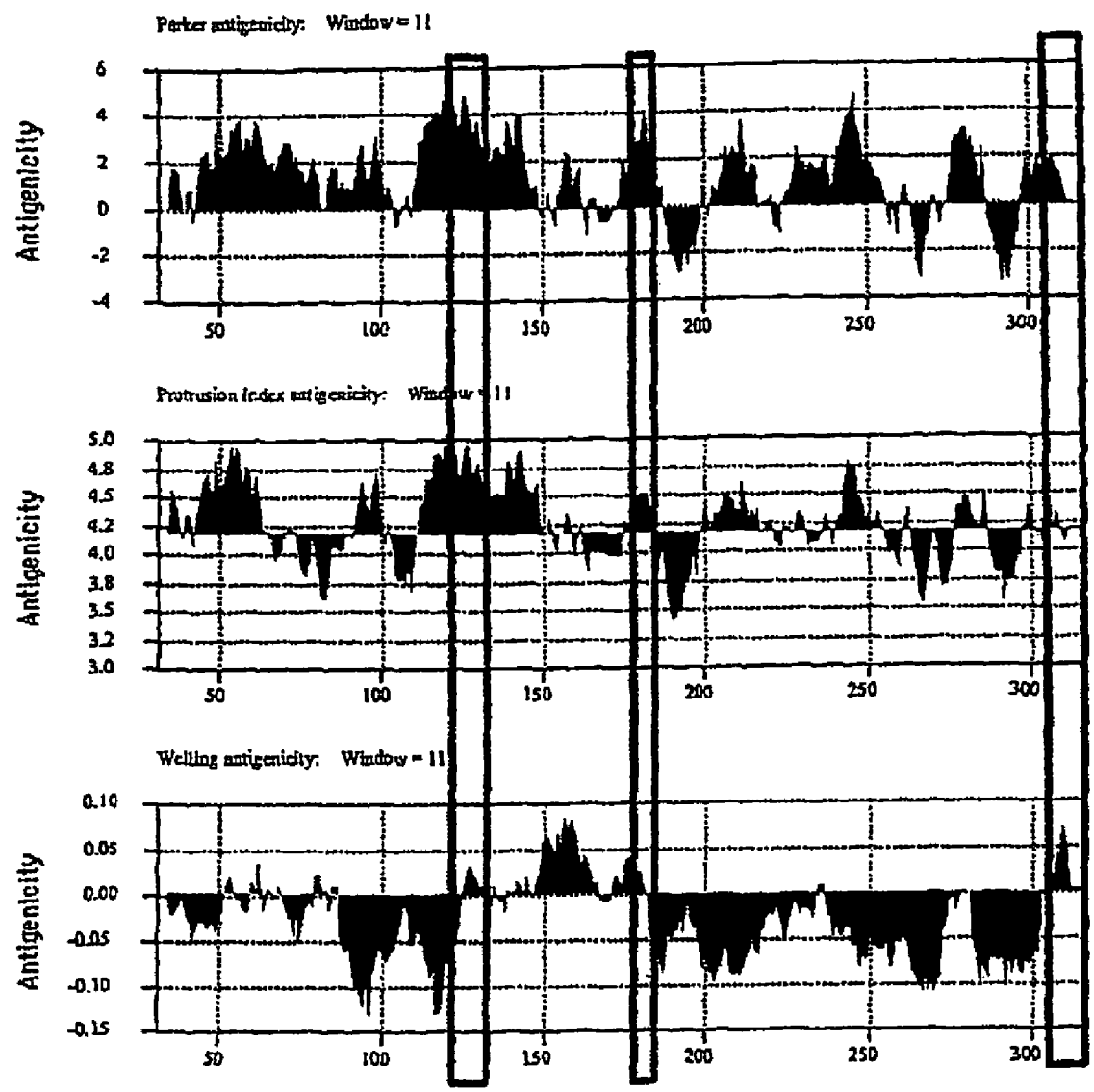
Figure 25B:
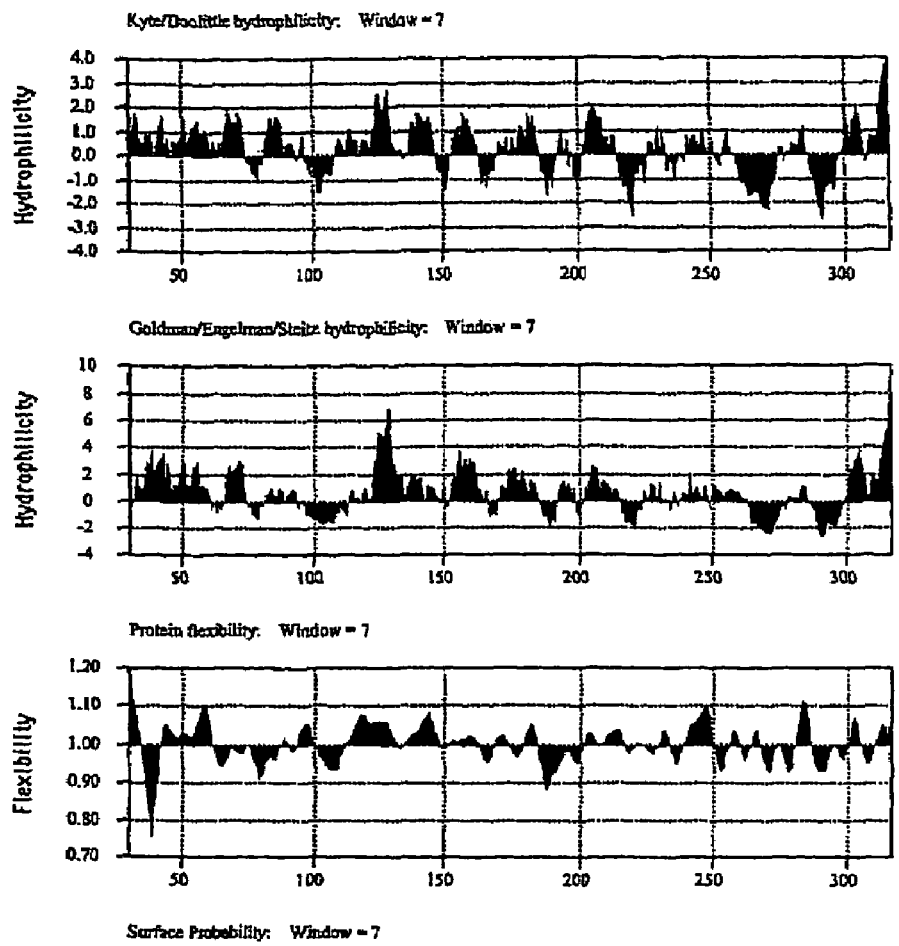
Figure 25C:
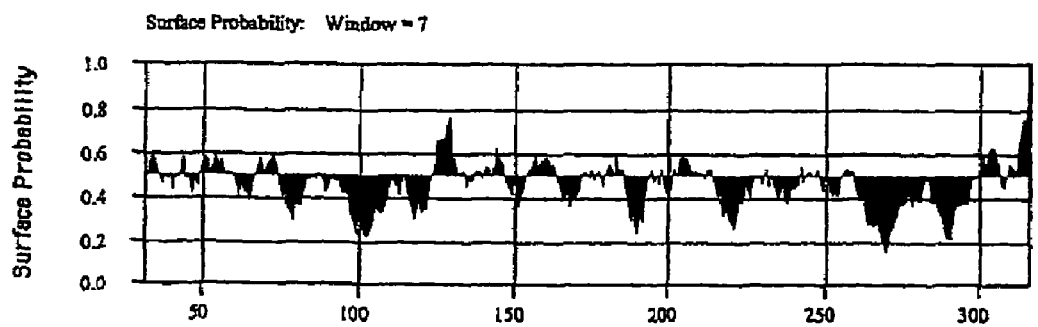

FIG. 25: Analysis of the antigenic properties of the ENV-SU protein

Analysis by Western blotting

FIGS. 25 a, b and c represent the analysis of the amino acid sequence of the MSRV ENV-SU protein using the "Mac Vector" analytical software, with the "Protein analysis toolbox" function. The regions boxed in by the 3 vertical rectangles represent the three most probable antigenic regions according to an analysis of the primary and secondary sequences.

25*a*, three graphs which illustrate the antigenicity of the "ENV-SU" regions. The shaded areas above "0" on the y-axis have a positive antigenicity, those below do not (negative antigenicity).

25*b*, the top two graphs illustrate the hydrophilicity of the "ENV-SU" regions. The shaded areas above "0" on the y-axis have a positive hydrophilicity, those below have a negative hydrophilicity.

The bottom graph illustrates the flexibility of the "ENV-SU" regions. The shaded areas above "0" on the y-axis have a positive flexibility, those below have a negative flexibility.

25*c*, the graph illustrates the surface probability of the "ENV-SU" regions. The shaded areas above "0" on the y-axis have a positive flexibility, those below have a negative surface probability.

EXPERIMENTAL SECTION

In Vitro Studies

Materials and Methods

Proteins and Toxins

The surface protein of the MSRV envelope (Env-SU) corresponds to a protein sequence of 287 amino acids (SEQ ID NO: 1) of the total envelope protein (Env pV14, GenBank AF331500). The structures and the amino acid sequences of Env, pV14 and of Env-SU are respectively represented in FIGS. 1(*a*) and 1(*b*) (SEQ ID NO: 3). The recombinant MSRV Env-SU protein is expressed in *E. coli* and purified on an FPLC column. The quality and the purity of the protein are confirmed by mass spectrometry and Western blotting.

Casein kinase is used as an autologous negative control. This control protein was produced and purified under the same conditions as Env-SU.

The two proteins are tested for the presence of endotoxins by means of a Limulus amebocyte lysate (LAL) test carried out by the company CleanCells (Bouffere, France). All the fractions are below the detection threshold of 5 IU/ml. The *staphylococcus* enterotoxin B (SEB) obtained from Toxin Technology (Sarasota, Fl, USA) was 95% pure. The lipopolysaccharide (LPS) of *E. coli* strain 026:B6 is obtained from Sigma Aldrich.

Culture Medium

The culture medium is the RPMI 1640 medium (Gibco) supplemented with:

1% L-glutamine (Sigma-Aldrich),

1% penicillin/streptomycin (Sigma-Aldrich),

1% sodium pyruvate (Sigma-Aldrich),

1% nonessential amino acids (Sigma-Aldrich), and

10% heat-inactivated FCS (fetal calf serum) (BioWest).

For the T cell proliferation assays, a human AB serum (Sigma-Aldrich) was used instead of the FCS.

Isolation of the Cells and Preparation

Human peripheral blood mononuclear cells (PBMCs) are isolated from normal donors by Ficoll Paque density gradient centrifugation. The monocytes of the PBMCs are purified by removing the T cells, the B cells, the dendritic cells, the NK cells and the basophils using the monocyte isolation kit sold by the company Miltenyi Biotec. In summary, the PBMCs are first incubated with a cocktail of monoclonal antibodies and of anti-human immunoglobulin conjugated to a hapten and labeled magnetically (anti-CD3, anti-CD7, anti-CD19, anti-CD45RA, anti-CD56 and anti-IgE), and then with microbeads (MACs MicroBeads) coupled to anti-hapten monoclonal antibodies. The magnetically labeled cells are finally removed by retaining them on a column in a magnetic field. The purity of the monocyte population recovered is always greater than 95%, as determined by the expression of CD14 by flow cytometry analysis. For the generation of monocyte-derived dendritic cells (MDDCs), the purified-monocytes are cultured for 5 days on 6-well plates containing IL-4 at 25 ng/ml and GM-CSF at 50 ng/ml in 2 ml of culture medium. At day D3 of the culture, the complete amount of cytokines is added to the cells. As shown by morphological analysis and by flow cytometry, the resulting cell preparation contains more than 90% of CD1a-positive dendritic cells.

Cell Stimulation

The cells(PBMCs, monocytes or MDDCs) are placed in 24-well plates, at a concentration of $1\times10^6$ cells per well, in 1 ml of culture medium before stimulation with Env-SU, LPS, SEB or the autologous control. They are then incubated at 37° C. in a humidified atmosphere at 5% $CO_2$. When indicated, the cells were preincubated either with 10 μg/ml of polymyxin B (Sigma-Aldrich), 20 μg/ml and 5 μg/ml of anti-CD14 monoclonal antibody, 20 μg/ml and 5 μg/ml of anti-TLR-4 antibody (HTA125, eBioscience) or with a control IgG of 2a isotype (IgG2a) (eBM2a, eBioscience) before the cell stimulation. In certain experiments, Env-SU, the autologous control, LPS and SEB are boiled for 30 minutes before the cell treatment.

In order to determine the specificity of the results, 1 μg of Env-SU, LPS, SEB and of the autologous control is preincubated at 4° C. for 1 hour with 30 μg/ml of monoclonal antibodies directed either against Env-SU (13H5A5; IgG1; biomérieux) or against GAG (3H1H6; IgG1, biomérieux).

Next, the cells are incubated for 24 hours at 37° C., and the culture supernatants are then harvested for analysis of the secretion of TNF-α, IL-1β and IL-6 by ELISA.

T Cell Proliferation Assays

The stimulated monocytes and MDDCs are used as T-cell stimulators. The allogenic T cells are used at $1\times10^5$ cells per well, as “responder” cells, in 96-well round-bottomed microplates. The stimulator cells are added to the T cells in increasing doses and the cultures are carried out in triplicate in a final volume of 200 μl of culture medium. After incubation for 5 days at 37° C., the T cell proliferation is evaluated by measuring the radioactivity incorporated. To do this, in the final 18 hours of incubation, 1 μCi of $^3$H thymidine is added to each well. The cells are then recovered on glass filter layers in order to measure the radioactivity incorporated.

Labeling by Immunofluorescence and Flow Cytometry

The cells are harvested, washed in PBS and then stained for different surface markers. The following monoclonal antibodies (Becton-Dickinson, San Jose, Calif.) were used: anti-CD1a allophycocyanin (HI149-APC), anti-CD14 fluorescein isothiocyanate (MOP9-FITC), CD40 phycoerythrin (5C3-PE), CD80 phycoerythrin (L307.4-PE), CD86 phycoerythrin (IT2.2-PE) and HLA-DR peridine chorophyll (L243-PerCP).

The direct immunofluorescence staining of the cells is carried out in ice-cooled PBS supplemented with 2% FCS, with the various antibodies at the concentrations recommended by the manufacturers. After 30 minutes at 4° C., the cells are washed and then analyzed using a FACS Calibur (trade name) and the CellQuest software (trade name) (Becton Dickinson).

Cytokine-production Assays

The culture supernatants are collected and conserved at −20° C. before analysis of the cytokine secretion. The amounts of cytokines are measured using the OptEIA (trade name) ELISA kits (Pharmigen) for IL-1beta, IL-6, IL-10, IL-12p40, IL-12p40 and TNF-alpha, observing the manufacturer’s instructions.

Results

Env-SU induces the production of the pro-inflammatory cytokines from human PBMCs.

The ability of the recombinant Env-SU protein to stimulate the secretion of cytokines in the PBMC cultures was tested. The PBMCs from normal donors were incubated for 24 hours with increasing doses of the recombinant Env-SU protein and the secretion of the cytokines TNF-α, IL-1β and IL-6 was evaluated by ELISA. The amounts of cytokines secreted were compared with those obtained with the autologous control, SEB (a well-characterized bacterial superantigen) and LPS, well known to have pro-inflammatory properties on human PBMCs. All the proteins and the toxins were used at a concentration of 1 μg/ml (optimal concentration for the induction of pro-inflammatory cytokines, determined by dose/response experiments). The results show that Env-SU induces the secretion of the three cytokines in a dose-dependent manner, even at doses as low as 10 ng/ml. As shown in FIG. 2, the cytokine secretion kinetics obtained with Env-SU are closer to those of LPS than those of SEB. In fact, the stimulation with Env-SU under the conditions of the in vitro assay developed and described here differs entirely from the superantigenic stimulation represented here with the SEB antigen: (i) no early secretion of interferon gamma (which signals the activation of T lymphocytes, specifically recognized at the level of the T-cell receptor (TCR) by the superantigens, (ii) substantial and early secretion of IL-6 (secreted by the monocytes-macrophages and not by the T lymphocytes) and of TNF-α, which are not produced under the conditions of our in vitro assay with a superantigen (as shown here with the example of SEB). Furthermore, the examples showing the activity, on the purified monocytes and the dendritic cells, of the MSRV/HERV-W Env protein, via its Env-SU region, confirm that these effects do not involve the TCR, which is not present on these cells, and therefore that the specific proinflammatory effect described here is indeed different from the pro-inflammatory activation caused by a superantigen function which, by definition, involves binding to the TCR and T lymphocytes. The pro-inflammatory activation pathway of the MSRV/HERV-W Env protein claimed here involves the "Toll-like receptor 4" (TLR4), optionally with the assistance of its coreceptor CD14, which is activated upstream of the activation of T lymphocytes, as illustrated in FIG. 8. This pro-inflammatory (TLR4) pathway mobilizes the "innate" component of the immune system, which is mobilized well upstream of the T-lymphocyte-related immunity (adaptive immunity). This upstream pathway can, after activation of the dendritic cells, influence, downstream, the state of activation of the adaptive immunity (Th1 or Th2) profiles, by means of the cytokines secreted in response to the activation of a receptor of innate immunity, such as TLR4. The latter effect shows, besides the fact that the innate immunity pathway is activated upstream of the T-lymphocyte-mediated adaptive immunity, that even the resulting downstream effect on the T lymphocytes does not involve the TCR receptor. This clearly illustrates the difference between the effect of the MSRV/HERV-W Env (Env-SU) protein observed at this level (TLR4) and the superantigen effect (illustrated by the SEB superantigen in this example) which involves the T lymphocyte receptor (TCR). Now, the TLR4 pathway excludes a primary activation of T lymphocytes at this stage and therefore involves other cells (monocyte-macrophages, dendritic cells, B lymphocytes). The activation pathway observed here is therefore upstream of the superantigen effect, which corroborates the kinetics which correspond to the reference "LPS" rather than "SEB" in the cell assay used here.

In fact, Env-SU and LPS are capable of inducing the secretion of large amounts of TNF-α, of IL-6 and of IL-1β right from 24 hours, whereas SEB induces only the secretion of TNF-α, even after 72 hours of incubation.

It is interesting to note that Env-SU and LPS reach their TNF-α secretion peak, whereas SEB induces a constant secretion of TNF-α. With respect to IL-1β, Env-SU and LPS induce a secretion profile similar to that of TNF-α, characterized by a secretion peak around 24 hours of incubation followed by a constant decrease. SEB, which is known to activate a large population of T lymphocytes bearing the same TCR Vβ specificity, does not induce any IL-1β. IL-6 is secreted constantly by the PBMCs stimulated with Env-SU and LPS, but not with SEB. IL-6 and IL-1β are two cytokines preferentially released by activated monocytes/macrophages. These data show that, in a manner similar to that of LPS, Env-SU targets the cells of the innate immune system, such as monocytes and macrophages, for the release of pro-inflammatory cytokines, and that T lymphocytes are not targeted at this level of activation.

To eliminate the possibility of a contamination with endotoxins of the Env-SU recombinant protein, the human PBMCs were either treated with an LPS inhibitor, polymyxin B (PB), before stimulation, or incubated with boiled proteins and toxins. In parallel, an autologous control produced and purified under the same conditions, with the same reactants and material: human casein kinase CK2, was also added.

After incubation for 24 hours, the culture supernatants were harvested and analyzed for TNF-α secretion. As shown in FIG. 4, the TNF-α induced by Env-SU and SEB is only partially inhibited by PB, whereas the effects of LPS are completely abolished. The control autologous protein does not induce any cytokine secretion. The release of TNF-α is also inhibited significantly when the Env-SU proteins are boiled for 30 minutes, whereas the LPS activity is not affected. This is in accordance with the negative results obtained during the quality control analysis carried out both on purified samples of Env-SU and of the autologous control using the LAL test, approved by the Food and Drug Administration.

These results demonstrate that the pro-inflammatory effects observed early on are not due to a contamination with endotoxins and that the component responsible for these effects is indeed a protein.

To confirm the specificity of the pro-inflammatory properties of Env-SU, the effects of monoclonal antibodies were studied. The PBMCs were incubated for 24 hours with the autologous control, Env-SU or LPS preincubated at 4° C. for 1 hour either with a monoclonal antibody directed against Env-SU, or with a monoclonal antibody directed against Gag. The Gag protein used to develop this monoclonal antibody does not exhibit any pro-inflammatory activity and constitutes an appropriate control. As shown in FIG. 4, the anti-Env-SU monoclonal antibody specifically blocks the secretion of TNF-α mediated by Env-SU, but not that mediated by LPS. The secretion of cytokines is not affected by the anti-Gag monoclonal antibody. These results demonstrate the specificity of Env-SU on the induction of cytokines and the cell activation.

Env-SU has the ability to induce pro-inflammatory cytokines in PBMC cultures. It has subsequently been verified that Env-SU is capable of directly activating purified monocytes. The purified monocytes were stimulated with the autologous control, Env-SU or LPS for 24 hours and various activation markers, such as CD80 and CD86 were evaluated by flow cytometry. Compared with the autologous control, Env-SU induces an upstream regulation of the two markers and the expression levels obtained are similar to those with LPS (FIG. 5a). Large amounts of TNF-α, of IL-Lβ, of IL-6 and of IL-12p40 are produced in response to Env-SU (FIG. 5b). These results show that Env-SU induces a rapid and direct activation of monocytes, associated with a production of pro-inflammatory cytokines.

The dendritic cells are antigen-presenting cells linking innate immunity and adaptive immunity with the unique ability to control the activation of naive T cells. The ability of Env-SU to directly activate monocyte-derived dendritic cells (MDDCs) was studied.

The dendritic cells were generated, in vitro, from highly purified monocytes stimulated for 24 hours with the autologous control, Env-SU or LPS. Env-SU is capable of drastically increasing the activation of the CD80, CD86, CD40 and HLA-DR markers (FIG. 6a). The pro-inflammatory cytokines IL-6, TNF-α, IL-12p40 and IL-12p70 are secreted at higher levels. It is shown that MDDCs stimulated with Env-SU are capable of inducing allogenic proliferation of T cells to a greater degree than the autologous control, even when the number of stimulatory cells is low (FIG. 6c). Therefore, similarly to LPS (positive control), Env-SU is capable of inducing the maturation of dendritic cells secreting IL-12 and is therefore capable of inducing primary specific immune responses.

To determine whether Env-SU uses the same activation pathway as LPS, the levels of TNF-α, secreted by human PBMCs after stimulation, with or without preincubation with anti-CD14 or anti-TLR4 neutralizing antibodies, were measured. The results presented in FIG. 7a show that the blocking of CD14 results in a significant dose-dependent inhibition of Env-SU and of the secretion of TNF-α mediated by LPS (83% and 56% respective inhibition with 20 μg of anti-CD14 antibodies). SEB, which is known to activate T cells and antigen-presenting cells via the T cell receptor and HLA-DR, is not inhibited. The blocking of TLR4 results in a 37% inhibition with respect to the effects of Env-SU and a 43% inhibition with respect to the effects of LPS, with 20 μg of anti-TLR4 antibodies (FIG. 7b). No inhibition effect is observed for the control antibodies in the two experiments. The CD14 and TLR4 receptors are therefore involved in the pro-inflammatory properties mediated by Env-SU.

In conclusion, the soluble fraction of the MSRV/HERV-W envelope protein stimulates an innate immune response via the CD14 and TLR4 recognition receptors and it is shown in the present invention that the immunopathological cascade that results in inflammatory lesions can be blocked at a very early stage by administration of a therapeutic composition or medicament comprising at least one antibody chosen from anti-Env-SU and/or anti-TLR4 antibodies.

Thus, in the present invention, after having tested various monoclonal antibodies produced by bioMé/rieux against the MSRV/HERV-W envelope proteins, the cell assay set up and developed in the present invention made it possible to identify those which have the property of inhibiting the pro-inflammatory effect activating the TLR4 pathway and to select, among the inhibitory antibodies, those which have an inhibitory potential closest to 100%. Among these antibodies, the antibodies 3B2H4 and 12H5A5 are the preferred antibodies.

It has thus been possible to identify the properties of inhibition of the early pathways of inflammation which are involved in pathologies such as MS and SCZ at a level a long way upstream of a pathogenic cascade which diverges further downstream in the processes of these two diseases, as is illustrated in FIGS. 8 and 9.

The usefulness of these antibodies, corresponding to the definitions given above, for the preparation of a pharmaceutical composition or of a medicament therefore obviously emerges since they make it possible to block, a long way upstream, a pathogenic cascade in pathologies such as MS or SCZ. Their advantage is also demonstrated by their inhibitory effect which lies before the interaction with the TLR-4 receptor, since the inhibition is equivalent to that obtained with the anti-TLR4 antibody in the same cell assay dedicated to the study of its early activation. This effect upstream of the activation of T lymphocytes thus makes it possible to block a pathological agonist which, at this stage, is common to autoimmune pathologies such as MS and non-autoimmune pathologies such as SCZ (cf.: FIG. 9). Thus, the antibodies of the invention make it possible to block, upstream, pathogenic cascades which differ downstream in pathologies such as MS and SCZ. FIG. 8 shows the target toward which the antibodies of the invention are directed in the pathogenic cascade of MS, which anticipates all the targets toward which the existing therapeutic agents are currently directed. In fact, at the stage at which the antibodies of the invention intervene, there is only one agonist (MSRV/HERV-W Env) and one receptor (TLR4), whereas, after activation of the receptor, hundreds of agonists in the form of bioactive molecules (cytokines, enzymes, free radicals, etc.) become involved in the inflammatory process, and then, in the case of MS, thousands of molecular and cellular agonists become involved after the phase consisting of activation of autoimmune T lymphocyte clones. In the case of schizophrenia (SCZ), it is not the T lymphocytes which are activated in an autoimmune pathway, but the pro-inflammatory mediators produced after the activation of the TLR4 pathway in a cell of the brain gray matter which cause excitotoxicity at the level of the adjacent neurons. These phenomena of excitotoxicity induced by the pro-inflammatory molecules are well described and cause an abnormal release of neuromediators which, in the frontal cortex of an individual, cause hallucinatory phenomena. It is even more advantageous to realize that these excitotoxic phenomena often result in a neurotoxicity which is reflected by neuronal death. Now, this neuronal death is known in SCZ and is objectified by virtue of ventricular enlargements typically visualized by MRI imaging in patients at an advanced stage of the pathology. In fact, the progressive loss of neurons in the brain of these patients is compensated for by an increase in the volume of the brain ventricles, which becomes detectable by MRI after a certain period of evolution of the disease. FIGS. 8 and 9 therefore clearly illustrate the fact that the anti-Env antibodies identified and selected by means of the cell assay developed in the context of the present invention really block the "primary" stimulus most upstream in this cascade, after the activation of one or more pathogenic copies of the MSRV/HERV-W family.

In order to confirm even more precisely the association between the expression of an envelope protein (Env) of the MSRV/HERV-W retroviral family and the MS and SCZ pathologies, studies were carried out using the innate immunity activation assay described in the present invention, in order to search for a bias in immunological activation in MS or SCZ patients, compared with normal controls.

Ex vivo Studies

Ex vivo Study in Patients Suffering from Multiple Sclerosis (MS)

Env-SU-induced IL-6 secretion is increased in blood mononuclear cells taken ex vivo from MS patients and correlates with their clinical score (EDSS).

In this study, the reactivity with respect to Env-SU of PBMCs from MS patients and from normal donors was compared. Thirty-two patients were included, twenty being in the acute phase and 12 in the stable phase according to an analysis made by MRI. Their level of disability was also determined according to the EDSS (extended disability score) criteria. In parallel, 19 normal donors were tested. Briefly, $1 \times 10^6$ PBMCs were incubated by Env-SU or with the Mock control for 24 hours, and then the culture supernatants were analyzed for the secretion of cytokines such as IFN-γ, TNF-α, IL-1β, IL-6 and IL-10. The results obtained (Env-SU-Mock) were first of all compared between the groups. No significant difference was observed for IFN-γ, TNF-α, IL-1β and IL-10 (FIG. 10). On the other hand, considerable differences were obtained with IL-6 and IL12p40, which are increased in the patients (FIG. 11). Furthermore, a positive correlation was observed between the level of secretion of IL-6 or of IL-12p40 obtained and the clinical score of the patients (FIG. 12). No other correlation was obtained with other cytokines or clinical data (age, sex, treatment). In FIG. 12, the absence of correlation between the induced IL-6 and the duration of the disease, and also the absence of correlation between interferon gamma and the EDSS are given as an example.

As regards the interferon gamma which is here secreted exclusively by the T lymphocytes, it is very interesting to note that, contrary to the cytokines associated with innate immunity, secreted here by the monocytes/macrophages, it does not correlate with the clinical score (EDSS). This clearly shows that, as was demonstrated in vitro with the cell assays, the effect revealed ex vivo clearly correlates an effect which is not mediated at this stage by T lymphocytes, and is therefore not related to a superantigen effect.

These results suggest that MS patients exhibiting the most advanced clinical signs (high EDSS) are "hypersensitive" to retroviral factors such as Env-SU, but may also suggest a role for Env-SU in the pathogenesis of MS via the pro-inflammatory cytokines and IL-6.

This confirms the data obtained with the MSRV viral load in the CSF of MS patients, in the study by Sotgiu et al. [10], which showed a gradual increase in the MSRV viral load with the worsening of the disease. According to the results of the invention, the response induced by the MSRV envelope protein increases, in a correlated manner, with the seriousness of the disease, measured by EDSS. These two independent studies carried out ex vivo on MS patients, with different approaches (firstly, assaying of MSRV nucleic acids by RT-PCR and, secondly, assaying of an immunological response to the MSRV envelope protein) confirm the association between the process of the disease itself and the MSRV retrovirus.

Ex vivo Study in Patients Suffering from Schizophrenia (SCZ)

Env-SU-induced IL-12p40 secretion is increased in the blood mononuclear cells taken ex vivo from SCZ patients, and, in addition, makes it possible to identify, at the highest levels, a subpopulation of patients resistant to anti-psychotic therapeutics and/or having particularly evolutive forms of SCZ.

In this study, the reactivity with respect to Env-SU of PBMCs from SCZ patients and from normal donors was compared. Twenty-five patients were included. In parallel, 15 normal donors were tested according to a protocol identical to that of the previous study with MS patients.

The culture supernatants were analyzed for the secretion of cytokines such as TNF-α, IL-12p40, IL-1β, IL-6 and IL-10. At this stage of the study, a notable difference was observed between some of the patients suffering from SCZ and all the controls, for various cytokines tested. The results are presented in Tables 1 and 2 which follow. Table 1 represents the various normal donors, whose code is indicated in the lines of the first column with, in each line, the amounts in ng/ml assayed for the various cytokines indicated at the top of the column with the two conditions indicated in the following line for their respective columns (Mock and ENV-SU stimulation). Table 2 represents the various MS patients, whose code is indicated in the lines of the first column with, in each line, the amounts in ng/ml assayed for the various cytokines indicated at the top of the column with the two conditions indicated in the following line for the respective columns (Mock and ENV-SU stimulation). In Tables 1 and 2, the bottom two lines (mean and St Dev) indicate, respectively for each column, the mean and the standard deviation of the data measured.

TABLE 1

|  | TNF-a Mock | ENV1 | IL-6 Mock | ENV1 | IL-10 Mock | ENV1 | IL-12p40 Mock | ENV1 | IL-1b Mock | ENV1 |
|---|---|---|---|---|---|---|---|---|---|---|
| ND 151003 | 24 | 500 | 216 | 3493 | 12 | 59 | 0 | 245 | 38 | 1149 |
| ND 291003 | 14 | 1491 | 166 | 14230 | 14 | 337 | 0 | 398 | 32 | 1677 |
| ND 011003 | 114 | 969 | 3727 | 12141 | 38 | 478 | 1 | 99 | 214 | 1712 |
| ND 300402 | 18 | 58 | 172 | 601 | 20 | 21 | 9 | 31 | 69 | 193 |
| ND 020702 | 0 | 139 | 111 | 1028 | 3.5 | 44 | 5 | 16 | 99 | 392 |
| ND 180602 | 48 | 264 | 92 | 1816 | 16 | 32 | 20 | 57 | 110 | 424 |
| ND 070801 | 0 | 124 | 84 | 1028 | 6 | 31 | 20 | 42 | 25 | 235 |
| ND 180901 | 1 | 228 | 39 | 2328 | 7 | 60 | 0 | 113 | 21 | 651 |
| ND 060701 | 30 | 260 | 345 | 3263 | 17 | 155 | 8 | 38 | 33 | 277 |
| ND 110901 | 0 | 328 | 70 | 7352 | 14 | 214 | 11 | 169 | 9 | 587 |
| ND 280801 | 7 | 58 | 77 | 882 | 20 | 30 | 4 | 57 | 52 | 168 |
| ND 190603 | ND | ND | 21 | 123 | 0 | 6 | 1 | 12 | 16 | 58 |
| ND 180602 (40 | 15 | 541 | 30 | 7569 | 6 | 171 | 11 | 107 | 8 | 723 |
| ND 2 (1) | ND | ND | 2870 | 8863 | 125 | 187 | 124 | 291 | ND | ND |
| ND 140504 | ND | ND | 185 | 803 | ND | ND | 8 | 8 | ND | ND |
| Mean | 22.58 | 413.33 | 547.00 | 4368.00 | 21.32 | 130.36 | 14.87 | 112.20 | 65.85 | 634.31 |
| St Dev | 20.94 | 307.94 | 733.73 | 3775.33 | 17.19 | 108.55 | 16.00 | 87.33 | 41.33 | 421.61 |

TABLE 2

| patients code Schizo | TNF-a Mock | ENV1 | IL-6 Mock | ENV1 | IL-10 Mock | ENV1 | IL-12p40 Mock | ENV1 | IL-1b Mock | ENV1 |
|---|---|---|---|---|---|---|---|---|---|---|
| 1 | 46 | 475 | 298 | 3491 | 82.9 | 25.6 | 9.5 | 302 | 8 | 835 |
| 2 | 40 | 1570 | 787 | 21956 | 73 | 389 | 29 | 559 | 84.6 | 5532 |
| 3 | 587 | 1639 | 9588 | 30299 | 124.6 | 800 | 171 | 438 | 988 | 6237 |
| 6 | 33 | 863 | 408 | 8494 | 88.9 | 139 | 36 | 152 | 46 | 1459 |
| 9 | 40 | 238 | 338 | 2819 | 34.5 | 22 | 63 | 24 | 111 | 932 |
| 10 | 10 | 310 | 527 | 7552 | 92.9 | 216 | 2 | 75 | 5 | 458 |
| 12 | 11 | 950 | 769 | 22510 | 14.9 | 769 | 87 | 158 | 70 | 1614 |
| 13 | 1031 | 2840 | 27022 | 38290 | 94 | 580 | 271 | 481 | 2396 | 10309 |
| P2 | NT | NT | 738 | 2857 | 34.01 | 68.75 | 3 | 12 | NT | NT |
| P3 | NT | NT | 3362 | 12521 | 193 | 259 | 32 | 93 | NT | NT |
| P4 | NT | NT | 3481 | 14305 | 189 | 273 | 72 | 84 | NT | NT |
| P5 | NT | NT | 903 | 4141 | 33 | 133 | 13 | 210 | NT | NT |
| P9 | NT | NT | 579 | 7925 | 14 | 109 | 7 | 28 | NT | NT |
| P16 | NT | NT | 787 | 1009 | 5 | 16 | 0 | 9 | NT | NT |
| P17 | NT | NT | 113 | 432 | 0 | 0 | 0 | 0 | NT | NT |
| P18 | NT | NT | 3168 | 10755 | 125 | 236 | 2 | 44 | NT | NT |
| P20 | NT | NT | 57 | 90 | 0 | 0 | 10 | 0 | NT | NT |
| P22 | NT | NT | 2461 | 8793 | 40 | 134 | 26 | 107 | NT | NT |
| P23 | NT | NT | 880 | 837 | 0 | 0 | 0 | 9 | NT | NT |
| P24 | NT | NT | 895 | 6833 | 8 | 101 | 4 | 38 | NT | NT |
| P27 | NT | NT | 3039 | 6816 | 132 | 230 | 57 | 49 | NT | NT |
| P28 | NT | NT | 99 | 135 | 2 | 7 | 3 | 11 | NT | NT |
| P30 | NT | NT | 2332 | >15000 | 189 | 785 | 28 | 734 | NT | NT |
| P32 | NT | NT | >15000 | >15000 | 233 | 805 | 40 | 584 | NT | NT |
| P33 | NT | NT | >15000 | >15000 | 249 | 452 | 11 | 18 | NT | NT |
| Mean | 224.75 | 1110.38 | 2723.04 | 9766.36 | 82.07 | 262.37 | 39.02 | 168.88 | 463.58 | 3434.50 |
| St Dev | 292.13 | 679.47 | 2897.37 | 7479.22 | 64.68 | 220.85 | 39.03 | 170.02 | 614.21 | 2968.63 |

Compared with the MS population previously studied, a difference is already observed spontaneously in culture for certain patients (illustrated in FIGS. 13 and 14 for IL-10 and IL-12p40. This attests to an unexpected datum, namely that, although SCZ is not a systemic inflammatory disease, and even less an autoimmune disease, certain SCZ patients exhibit a degree of spontaneous immunological activation in their PBMCs which exceeds both that of the normal controls and that of the MS patients under the same conditions. This introduces an important datum into the notion of systemic activation of immunity in these patients and therefore confirms the reality of this pro-inflammatory immunological component in this disease.

The response to the stimulation with Env-SU is, overall, further increased in the series of SCZ patients, and certain patients respond with cytokine secretion levels that are clearly greater than the mean of the normal controls and even sometimes greater than the maximum observed in the series of controls (as illustrated in FIGS. 13 and 14, for IL-10 and IL-12p40). This also confirms that the response to Env-SU is significantly increased in certain patients suffering from SCZ and that Env-SU is therefore capable of revealing an immunological bias involving the components of innate immunity activated via the TLR4 pathway, in some of these patients whose clinical status coincides.

However, in these patients, the increase, after stimulation with Env-SU, relative to the spontaneous cytokine level (stimulated level−spontaneous level/spontaneous level) is, overall, less in the SCZ patients than in the normal controls; this being the case even when the level of secretion induced by ENV-1 exceeds that of all the normal controls (as illustrated in FIGS. 14 b and c, for IL-12p40). This introduces a new element with regard to that which has been described in a pathology such as MS, in relation to the etiopathogenic role of a retroviral element of the MSRV/HERV-W family. In fact, the role of a retroviral element of this MSRV/HERV-W family in SCZ has also been demonstrated and confirmed by several independent teams with different approaches [3, 14, 31, 54], but SCZ is not a disease with an autoimmune pathological component like MS. Thus, the results obtained with the Env-SU protein on the PBMCs from SCZ patients show that, although the consequences downstream of the immunological activation which concern T lymphocytes (cells responsible for autoimmunity) are different from MS, a pathway of early activation of innate immunity involving the TLR4 receptor (which is not present in T lymphocytes) may nevertheless constitute an initial pathogenic pathway, between these two diseases and the MSRV/HERV-W retroviral family.

As was previously mentioned, the role of an MSRV/HERV-W envelope protein in these patients now becomes objectified by the specific immunological reactivity of their blood mononuclear cells (PBMCs) with respect to the Env-SU protein.

The most advantageous and the most relevant differences with regard to the clinical data of patients suffering from SCZ, at this stage of the study, were observed for IL12p40 (FIG. 14).

In fact, it was verified that the patients exhibiting one of the highest Env-SU-induced IL-12p40 levels (here, greater than 400 pg/ml, therefore at the maximum level of the normal controls tested in this series) comprise all the patients resistant to the antipsychotic therapeutics of the series tested and with particularly evolutive forms of schizophrenia.

This shows that, with a profile different from that obtained previously with MS patients, there exists at least one subpopulation of patients suffering from evolutive forms and/or forms resistant to existing treatments which is identifiable and characterized by virtue of an Env-SU-induced IL12p40 secretion greater than the average.

The fact that at least the IL12p40 induced by the Env-SU activation in the PBMCs from SCZ patients is at a maximum in the evolutive forms and/or forms resistant to current treatments demonstrates, in addition to the association between criteria of evolution and of severity of the disease, a novel therapeutic target for these patients, namely the MSRV/HERV-W Env protein associated with this immunological bias in the patients.

As is, moreover, demonstrated for the MS models, antibodies capable of inhibiting the activation of the immune system before involvement of the "upstream" pathway mediated by the TLR4 receptor are of therapeutic interest and their target is very advantageous in the newly identified clinicobiological context.

Contrary to MS, where the subsequent consequence of these effects is an autoimmune reactivity which targets the antigenic components of myelin, the mediators produced at this early stage of activation of innate immunity (TLR4) with a spontaneous level ex vivo higher than in MS, have an excitotoxic potential on cortical neurons [17, 21, 23-25, 29, 50, 51, 55].

Thus, the activation of an MSRV/HERV-W provirus by various cofactors can activate the expression of the MSRV/HERV-W Env protein in brain cells [56] and, depending on the nature of the cofactor and the circumstances, target different areas of the brain. Under these conditions, an activation in the regions of the frontal cortex can bring about neuronal excitotoxicity reflected by various hallucinations depending on the areas affected.

In the case of an activation in the (myelinated) white matter, the early inflammation produced by the Env protein at the level of the macrophages and/or the microgliocytes is capable of stimulating myelin degradation and therefore, after contribution from the T lymphocytes, of inducing autoimmunity against the autoantigens of myelin.

These various notions revealed are illustrated in FIG. 9. This shows that, in the clinicobiological context thus identified in patients suffering from schizophrenia, it is useful to inhibit this neurotoxic inflammatory component obviously related to the symptoms of the disease.

Furthermore, as is also illustrated in FIG. 8, the level at which these antibodies inhibit the biological effects of the Env protein is clearly upstream of all the pathological mediators which are produced downstream and which are the usual targets of conventional anti-inflammatory therapeutics (cytokines, free-radicals, redox compounds, enzymes, prostaglandins, pro-inflammatory proteins and lipids, activated T lymphocytes, etc.). At this stage, the only agonist is the MSRV/HERV-W Env protein itself and preventing it from activating the TLR4 receptor blocks the initial route of entry of the various immunobiological cascades which result therefrom downstream, as illustrated in FIGS. 8 and 9.

It is within the scope of those skilled in the art to undertake the preclinical development studies, such as:
  monoclonal antibody humanization, according to the methods used for known therapeutic antibodies such as the anti-TNF-alpha REMICADE. The optimization of the intracerebral passage of therapeutic antibodies is carried out according to techniques that are now well known, most of which are described in numerous scientific and medical publications, as described, for example, by Merlo et al., or by Pranzatelli [57, 58];
  verification of the inhibitory activity of these humanized or modified antibodies with the test for pro-inflammatory activation by the Env-SU protein on PBMCs, as described in the present invention;

verification of the therapeutic effect of the antibodies on animal models demonstrating the behavioral effects of the abnormal expression of the MSRV/HERV-W Env protein in the brain [59].

Thus, the elements of the present invention, namely:

the demonstration of the "TLR4" receptor for the MSRV/HERV-W envelope protein as a route of entry for "upstream" pro-inflammatory activation at the level of the cells of innate immunity, the cell assay which makes it possible to detect and measure these effects, the anti-Env monoclonal antibodies capable of inhibiting the effects of this protein, the pieces of biological evidence of these effects at the level of the blood immune cells taken ex vivo from patients suffering from schizophrenia, the pieces of biological evidence linking these effects to the pathology allow those skilled in the art to carry out, with the knowledge, techniques and animal models known to date, the preclinical development steps and to tackle the clinical studies in humans under the appropriate conditions. Furthermore, the biological tests described in the present invention allow an ex vivo biological investigation of the parameters targeted by these therapeutic antibodies, before, during or after treatment of the patients, by means of a simple blood sample.

Such therapeutic guidance provides a very valuable advantage for the definition of the patients eligible for a treatment at a given moment or in a given subgroup, and makes it possible to adjust the therapy in terms of dose and frequency according to the biological results.

Animal Models

Production of a model for studying the pharmacokinetic distribution and the toxicology of the therapeutic antibodies and of controls in an animal model Antibodies:

1. Nature of the Antibodies:

In order to prevent too rapid and too great a degradation in the liver, the antibodies of interest are used in the form of fragments of Fab' or Fab2 type, obtained from monoclonal antibodies according to the techniques known to those skilled in the art [60]. The anti-MSRV/HERV-W Env antibodies, which inhibit the pro-inflammatory effect mediated by TLR4, are the antibodies 13H5A5 and 3B2H4. The anti-MSRV/HERV-W Gag control antibody is the antibody 3H1H6.

2. Antibody Labeling Protocol:

The fragments are first of all diluted. 100 µl at a concentration of 1 µg/µl are thus prepared and then brought into contact with sodium iodide (NaI$^{125}$ NEN, at 5 mCi/50 µl) adsorbed onto beads (Iodobeads No. 28665 Pierce Rockford, Ill., USA), as recommended by the manufacturers.

After incubation for 10 minutes, the solution is removed and transferred to a tube free of beads. This process makes it possible to stop the reaction and thus to avoid oxidation of the active site of the antibody, which would result in a loss of function.

The sample is then neutralized with 10 µl of a 4 mg/ml solution of sodium pyrosulfite (Fluka). Finally, the sodium iodide is entrained using 10 µl of cold entraining agent at a dose of 250 nM/ml.

3. Purification

The purification is carried out by the anion-exchange-column separation technique. This method uses an anion exchange column intended to bind the free iodine. Firstly, it is activated with 2 ml of a 0.9% NaCl solution (Aguettant), the migration buffer. The purification is carried out in four passes, entrained with 0.5 ml of 0.9% NaCl. The radioactivity contained in the four tubes is then counted.

4. Yield

The results are reported in Table 3, which represents the percentage recovery of each antibody after the purification.

The labeling yield is correct after 10 minutes of incubation. It does not increase over time. The percentage obtained for all the fragments is between 70% and 80%.

The ion-exchange purification allows good recovery of the labeled antibodies. For the 3B2H4 Fab2 fragment, the ratio is only 50%.

Evaluation of Biodistribution:

1. Mice

The animals involved in the experiment are 7-week-old BALB/c mice provided by the Charles River Laboratories (Wilmington, N.C., USA). The supplier guarantees that the animals are healthy.

They are maintained, while awaiting experimentation, in an installation under temperate conditions and with cyclical lighting, with care.

2. Protocol

The batches consist of three 7-week-old BALB/c white mice for each fragment tested.

In a first step, they are anesthetized with pentobarbital or with a volume-for-volume mixture of 2% ketamine-xylamine 10 g/100 ml, administered at a dose of 1 µl/g of weight.

They are then injected intravenously (IV) with 0.15 mg of antibody labeled at 700 µCi/mg (the mice are inoculated with the fragments of one of the three antibodies tested (3B2H4, 13H5A5 and 3H1H6)).

A reading is carried out at 10, 45, 90 and 210 minutes after injection.

After these 210 minutes, the mouse is sacrificed and the following are removed: spleen, liver, kidneys, brain, heart, lungs and blood. The tail is also kept in order to adjust the values obtained.

3. Results

No tissue pathology evoking an acute toxicity related to these antibodies was observed.

The results of biodistribution of the antibodies are reported in Table 4, which represents the distribution of the dose of labeled antibody in the various organs 210 minutes after IV injection.

Table 4 demonstrates that none of the fragments tested bind abnormally in a tissue.

These results demonstrate that the antibodies have no acute toxicity, and can be assayed in the biological fluids and tissues, and that their distribution corresponds to that expected by those skilled in the art.

Thus, any optimization of the biodistribution of these antibodies and/or any verification of these constants after their modification can be evaluated in relation to its pharmacokinetic and toxicological relevance according to the same protocol or its equivalent.

TABLE 3

Percentage recovery of the antibody fragments during the labeling with iodine 125

| | Recovery percentages Antibodies | | | | |
|---|---|---|---|---|---|
| | 3H1H6 | | 3B2H4 | | 13H5A1 |
| | Fab' | Fab2 | Fab' | Fab2 | Fab' |
| After binding | 72.69% | 82.00% | 74.36% | 75.95% | 74.22% |
| After purification | 62.70% | 73% | 75.10% | 41.70% | 76.20% |

TABLE 4

Mean percentage of the dose of antibody found in the various organs 210 minutes after injection in the BALB/c mouse

| | 3H1H6 Fab' | 3B2H4 Fab' | 3B2H4 Fab2 | 13H5H1 Fab' |
|---|---|---|---|---|
| Spleen | 1.28 | 1.68 | 2.26 | 1.30 |
| Brain | 0.18 | 0.28 | 0.60 | 0.17 |
| Kidney | 7.07 | 16.34 | 12.88 | 20.64 |
| Liver | 1.31 | 1.24 | 1.80 | 0.97 |
| Blood | 2.98 | 3.28 | 5.54 | 2.87 |
| Heart | 0.00 | 1.30 | 1.87 | 0.95 |
| Lungs | 0.00 | 2.14 | 2.68 | 0.60 |

In parallel with the direct study of the patients, animal models were produced, which make it possible to confirm that:

The "pro-inflammatory" pathology corresponding to the activation pathways "innate immunity alone" (model SCID-hu and Env-SU protein) or "innate immunity and superantigen effect on T lymphocytes" (model SCID-hu and virion), produced by an MSRV/HERV-W Env protein, is clearly observed in vivo and can be analyzed by means of objective criteria. The pathway "innate immunity/TLR4+/−CD14 activation pathway" is the subject matter of this invention and has the advantage of blocking the pro-inflammatory cascade upstream.

The autoimmune pathology directed against myelin autoantigens as in MS is clearly obtained with the MSRV/HERV-W Env protein (model EAE MOG Env-SU) and can be analyzed.

The use of anti-Env monoclonal antibodies selected for their inhibitory properties, and of fragments thereof bearing the immunological recognition specificity, is compatible with a therapeutic composition exhibiting a measurable organic distribution and a lack of organic toxicity in the animal (model BALB/c radiolabeled antibody).

The therapeutic use of anti-Env antibodies obtained by means of a prior selection of the anti-Env monoclonals in the test for "cellular" activation of the TLR4/innate immunity pathway. This use is illustrated in a model such as "EAE" (experimental allergic encephalomyelitis) in the presence of "MOG" (myelin oligodendrocyte glycoprotein) autoantigen induced by Env, and makes it possible to inhibit, beyond the inhibition of the pro-inflammatory activation phase well described here, the pathological consequences much further downstream (cf.: inhibition by the anti-Env antibodies in the EAE-MOG model).

Furthermore, after a selection of the anti-Env antibodies which inhibit the pro-inflammatory effect by means of the in vitro cell assay described in the present invention, the animal models make it possible to select, from this first selection, the therapeutic antibodies which have no harmful side effects following their therapeutic use in the pathological context. In fact, as was shown for an antibody which potentiates the neurological damage in the example "EAE-MOG" (cf.: example EAE-MOG and antibody 3H1H6), some antibodies can prove to be unsuitable for therapy irrespective of their specificity, and, even if they inhibit a pathological target, these side effects must cause them to be eliminated or modified before therapeutic use in a specific context. The tools developed during the present invention therefore make it possible to identify these possible harmful effects in the pathological context of use and therefore contribute, in an original and suitable manner, to the selection and to the validation of the suitable therapeutic antibodies.

Inflammatory Models on Cells and Animals:

Materials and Methods

Proteins and Toxins

The lipopolysaccharide (LPS) of the *E. coli* strain 026:B6 was obtained from Sigma (St Louis, Mich). The recombinant Env-SU protein represents a fraction of the whole MSRV envelope protein, ENV pV14, of approximately 33 kDa and 287 amino acids. Env-SU was produced in *E. coli*, purified by chromatography and analyzed by Western blotting (Protein Expert, Grenoble). An LAL test (limulus amebocyte lysate, Clean Cell, Bouffere, France) was carried out in order to detect the possible presence of endotoxins. The results were negative, below the detection threshold of 5 IU/ml. The buffer used for conserving the protein will be used in the experiments as a negative control. It consists of 50 mM Tris, pH 8, 0.3M NaCl, 1 mM β-mercaptoethanol, 2% sucrose, 2% glycerol and 5.3 mM urea.

Cell Culture

Preparation of PBMCS

The PBMCs were prepared from citrated fresh whole blood from normal donors (citrated whole blood bags, Centre de Transfusion Sanguine [Blood Bank] of Valence, France) by Ficoll (Amersham Biosciences, Freiburg, Germany) density gradient. The dilution of 25 ml of blood with 10 ml of PBS-2% FCS (fetal calf serum), carefully deposited onto 15 ml of Ficoll, is centrifuged at 2400 rpm for 20 min at ambient temperature (AT). The bands containing the cells are recovered and the PBMCs are washed three times with 50 ml of PBS-2% FCS (FIG. 11). After counting with trypan blue, the cells are frozen at −80° C. in a 90% dFCS-10% DMSO mixture and used directly in culture for cell assays or for injection into mice.

Preparation of Murine Splenocyte Suspensions

After sacrifice of the mice by cervical dislocation, the spleens are removed and ground on a metal filter in RPMI. The cell suspensions are centrifuged at 1200 rpm for 10 min at 4° C. The cell pellet is then taken up in approximately 4 ml of physiological saline or of dFCS (for, respectively, injection into C57B16 mice or freezing). Trypan-blue counting is carried out and the cell concentration is then adjusted. The cells are then frozen or used for the animal models. For injection into mice, gentamycin is added at a concentration of 0.2 mg/ml. Finally, 500 μl, i.e. 50×10$^6$ cells, are injected IP (intraperitoneally) into each of the C57B16 mice.

Freezing and Thawing of Cells

The cell suspensions are washed once in 50 ml of PBS (bioMérieux, France) at 4° C. and centrifuged at 1400 rpm for 7 min at 4° C. The cells were then taken up in a few ml of FCS and counted. The cell concentration is then adjusted to $20\times10^6$ in general. 500 µl of this solution are placed in cryotubes and then 500 µl of freezing solution (80% dFCS-20% DMSO (Sigma)) are added. Thus, the cells are conserved in 1 ml of 90% FCS-10% DMSO solution. The cryotubes are placed in a freezing dish containing isopropanol so as to obtain a slow decrease in temperature, and placed at −80° C.

The cell suspensions are thawed in a water bath at 37° C. The tubes are washed with alcohol before they are opened. The cells are rapidly transferred into 50 ml of RPMIc-10% dFCS and centrifuged at 1400 rpm for 7 min at 4° C., and then two other washes are carried out with RPMIc-10% FCS.

Culture Maintenance

The cell (PBMC) cultures are incubated in a humid atmosphere under 5% $CO_2$ at 37° C. The culture medium used consists of RPMI 1640 (Gibco, Rockeville, Md.) supplemented with 1% of L-glutamine, 1% of penicillin-streptomycin, 1% of sodium pyruvate, 1% of nonessential amino acids (Sigma) and 10% of fetal calf serum (Biowest, Nuaille, France) decomplemented (dFCS) by heating at 56° C. for 30 min.

Cell Stimulations

The cell suspensions (PBMCs or splenocytes) are thawed and trypan-blue counting is carried out: the cell concentration is adjusted to $1\times10^6$ cells/ml. The cultures are realized in 48-well plates (500 µl of cell suspension per well) or in 24-well plates (1 ml of cell suspension per well). After the cells have been deposited in the plates, the various substances to be tested are added and the cells are incubated for varying periods of time. The supernatants are harvested by centrifugation of the cell suspensions at 6000 rpm for 10 min at AT. They are then frozen in an Eppendorf tube at −20° C. Unless indicated, the concentrations of Env-SU and of LPS used for the cell assays were 1 µg/ml. For some experiments, Env-SU and the LPS were boiled for 30 min. Polymyxin B (PB) was used at 25 g/ml, and preincubated 45 min at 37° C. with the cells before addition of the buffer, LPS or Env-SU. For the experiments requiring the use of antibodies, preincubations, at 4° C. or 37° C., of the cells with the antibodies, or of Env-SU, LPS or buffer with the antibodies, were required, for various periods of time. The anti-Env-SU (13H5A5 and 3B3H4) and anti-Gag (3H1H6) IgG monoclonal antibodies (bioMérieux) were obtained by culture of hybridomas after immunization of the mice with, respectively, the recombinant Env-SU or Gag proteins. The specificity of the anti-Env-SU antibodies was verified by ELISA. Unless indicated, the concentrations of 13H5A5, 3B2H4 and 3H1H6 used for the cell assays were 30 □g/ml.

Animal Models

Maintenance of Mice

The C57B16, BalbC or SCID mice (Charles River, L'Arbresle, France) are purchased at 5 or 6 weeks old and are kept for one week, resting after receipt. They are housed in sterile filtering cages at a temperature of 24° C. All handling is carried out under a laminar flow hood.

Humanization of SCID mice and Preparation of C57B16 Mice

After one week of adaptation, the SCID mice are given an intraperitoneal (IP) injection of $50\times10^6$ fresh human PBMCs in 2 ml of RPMI without phenol red (Eurdbio, Les Ulis, France) supplemented with gentamycin at a concentration of 0.25 mg/ml, and are again left to rest for one week. In order to guarantee good humanization, 50 µl of anti-NK antibodies (25 µl of pure antibodies diluted in 25 microl of physiological saline) are injected via the RO route two days before the injection of the PBMCS. One week after the humanization, a blood sample is taken, via the RO route, from each mouse and the serum is conserved at −80° C. in order to be able to test the degree of humanization of the mice.

The C57B16 mice are given, after one week of adaptation, an intraperitoneal (IP) injection of $50\times10^6$ fresh murine splenocytes in 2 ml of RPMI without phenol red, supplemented with gentamycin at a concentration of 0.25 mg/ml, and are again left to rest for one week. During the IP injections, in the SCID mice as in the C57B16 mice, the liquid is rapidly resorbed, but some loss is observed.

Assaying of Human IgGs in the Humanized SCID Mice

The assaying of the human IgGs in the serum of the SCID mice is carried out by the radial immunodiffusion method according to the manufacturer's instructions (The binding site, Birmingham, UK). The measurement of the diameter of the precipitate 96 h after deposition of the serum onto the gel makes it possible, by means of a calibration curve, to relate the square thereof to the IgG concentration of the sample tested.

Injections of the Various Substances and Samples Taken From the Mice

At D0, the proteins (Env-SU), toxins (LPS) or buffer are assigned to the mice by IP injection after dilution of the substances in 1 ml of physiological saline (Fresenius Kabi, Bad Homburg, Germany), to the desired concentration. For the injections of anti-Env-SU or anti-GaG antibodies, the latter are incubated beforehand for 3 h at 4° C. with Env-SU, LPS or buffer. The control mice are given 1 ml of physiological saline. The samples are taken a few hours (1 h, 2 h) or days (24, 48, 72 h) later. After the mice had been anesthetized with ether, the maximum amount of blood (approximately 1 ml) is taken via the retroorbital (RO) route with a Pasteur pipette. 2 ml of physiological saline are then injected into the intraperitoneal (IP) cavity, and after massaging of the abdomen, the maximum amount of liquid is withdrawn (1 to 1.5 ml). Finally, the mice are sacrificed by cervical dislocation and the spleen is removed. The various protocols used are presented in FIGS. 12, 13 and 14. All the mice are observed clinically until the end of the experiment. Signs of inflammation and signs of nervous system damage are particularly noted.

Treatments of the Samples Taken from the Mice

The removed spleen is divided into two fragments. A part thereof is suspended by grinding on a screen in RPMI. After centrifugation at 1200 rpm for 10 min at 4° C., the cells are taken up in 50 ml of PBS at 4° C. and then centrifuged and frozen in a cryotube in 1 ml of freezing solution (10% DMSO-90% FCS). Another part of the spleen is frozen, as it is, in an Eppendorf at −80° C. The liquid withdrawn IP is centrifuged at 6000 rpm for 10 min at AT in order to remove the cell pellet, and frozen at −80° C. in an Eppendorf tube. After washing in PBS, the cells removed from the peritoneal cavity are, in turn, frozen. The blood is centrifuged at 6000 rpm for 10 min at AT in order to recover the serum. The latter and also the cell pellet are frozen separately in an Eppendorf tube at −80° C.

Treatment of Results

Cell Labeling and Flow Cytometry

The cell suspensions are thawed and the cells are taken up in 50 ml of PBS-2% dFCS-1 mM EDTA and centrifuged at 1400 rpm for 7 min at 4° C. Trypan-blue counting is carried out and the cells are deposited into 96-well plates (approximately $1\times10^6$ per well). After centrifugation of the plate at 4000 rpm for 1 min at 4° C., the supernatants are removed and 50 µl of the cocktail of surface marker antibodies (dilution in PBS-2% dFCS-1 mM EDTA) are added to each well. The cells are resuspended and incubated for 30 min at 4° C. They are then washed by adding 100 µl of PBS-2% FCS-1 mM EDTA per well and centrifuged at 4000 rpm for 1 min at 4° C. The supernatants are removed and 200 µl of PBS-2% FCS-1 mM EDTA are added per well. The cells are resuspended and transferred into tubes for the FACS analysis (FIG. 15). For the antibodies requiring streptavidin-APC second labeling, the same cycle is carried out one more time. The antibodies (Pharmingen, San Diego, Calif.) and dilutions used for labeling the murine cells are: CD3-FITC (1/500), CD4-PE (1/1000), CD8-cy-chrome (1/600), CD25-APC (1/1000), CD69-APC (1/500, biotinylated at the start). For labeling the human cells, 2□1 of each antibody are used: CD3-cy-chrome, CD4-APC, CD8-PE, CD25-PE, CD69-FITC.

Assaying of Cytokines

The culture supernatants, sera and liquids derived from the intraperitoneal lavages were conserved at −20° C. before assaying the cytokines by ELISA. The human or murine cytokine (TNF-α and IL-6) assays using the ELISA method were carried out according to the manufacturer's (Pharmingen) instructions.

Selection of the Anti-envelope Antibodies which Inhibit the Pro-inflammatory Effect Induced by the MSRV Envelope Protein at the Level of the Cells of Innate Immunity (via the TLR4 Activation Pathway)

Various anti-MSRV/HERV-W envelope antibodies produced in the monoclonal antibody laboratory of the company bioMérieux were tested in cultures of blood mononuclear cells (PBMCS) from normal donors, with assaying of cytokines (IL-6 and/or TNF-alpha), in the absence or presence of Env-SU protein, in order to determine their effect on the activation of monocytes/macrophages present in the culture, via a pathway which we verified, moreover, to be that of the "TLR4" receptor, according to the protocols described in the present invention, and in particular with the antibodies produced by the hybridomas 3H10F10, 13H5A5, 6A2B2, 2A12A5, 3C1D5 and 3B2H4.

Some anti-Env antibodies had no detectable inhibitory activity in these assays (6A2B2 and 2A12A5), or moderate inhibitory activity (3C1D5) or an activity which was unequal according to the experiments carried out with PBMCs from various donors (3H10F10). Examples of these assays are shown in FIG. 15 (15a, b, c and d), which illustrate the effects of these antibodies with respect to the pro-inflammatory activation produced by the Env-SU protein in various experiments.

Furthermore, an antibody such as that produced by the hybridoma 2A12A5, in the absence of inhibitory activity on the Env-SU protein, paradoxically produced a nonspecific immunostimulation in the assay, even in the absence of Env-SU protein.

Control antibodies, tested in these same assays, did not show any particular inhibitory or stimulatory activity, in particular the anti-GAG antibody 3H1H6.

The anti-MSRV/HERV-W Env monoclonal antibodies produced by the hybridomas 13H5A5 and 3B2H4 proved to be constantly inhibitory with respect to the effect of the Env-SU protein on the PBMCs of various normal human donors, without any paradoxical pro-inflammatory effect or any significant variation between assays carried out with the PBMCs of various normal donors, detectable under the conditions realized.

An example of the inhibitory activity of the antibodies 3B2H4 and 13H5A5 and of the absence of effect of the anti-MSRV GAG antibody 3H1H6 is shown in FIG. 15a. The conditions of specificity of the inhibition are validated in relation to another ligand which stimulates this activation pathway (LPS), on which these antibodies have no effect. FIG. 15b shows that the conditions of specificity of activation by the Env-SU protein are validated by the absence of effect of a control (mock) protein produced and purified under identical conditions, and by the tests confirming the absence of contamination, of the Env-SU sample used, with bacterial LPS (inhibition by heating at 100° C., which denatures the proteins and not the LPS, and absence of inhibition by polymyxin B, which inhibits the effect of LPS).

Thus, after having tested the various monoclonal antibodies obtained by bioMérieux against the MSRV/HERV-W envelope proteins, the cell assay set up and developed in the present invention made it possible to identify those which are capable of inhibiting the pro-inflammatory effect activating the TLR4 pathway and of selecting, from the inhibitory antibodies, those which have an inhibitory potential closest to 100%. Among these antibodies, the antibodies 3B2H4 and 13H5A5 are preferred. The usefulness of these antibodies or of other antibodies which can be produced by conventional techniques within the scope of those skilled in the art, as described above, is therefore confirmed.

Effect of the MSRV Env Protein on the Human Immune System, in an Animal Model Grafted with a Functional Human Lymphoid System Preparation of the Mice:

The following experiment involves seventeen 6-week-old female C57B16 mice. The first step consists in injecting, IP, 50 million human PBLs. The mice are irradiated beforehand and are given an injection of anti-NK antibodies (Firouzi et al., Journal of Neurovirology 2003). The mice are left to rest for one week, the period of time necessary for the stabilization of the immune system.

Preparation of Human PBLs

The cell suspensions are grouped together in a 50 ml tube, and centrifuged for 10 min at 4° C. and at 1200 rpm. The cell pellet is then taken up in approximately 4 ml of physiological saline. Trypan-blue counting is carried out and the concentration of the cells is then adjusted. Gentamycin is added at a concentration of 0.2 mg/ml. Finally, 500 µl, i.e. 50×10⁶ cells, are injected, IP, into each of the 17 C57Bl6 mice. Constitution of the inoculation batches:

The mice are divided up into groups of 3 or 4. Each batch thus formed is named in the following way:

3*"C" for the negative control group which will be given the ENV1 buffer.

3*"LPS" for the group which will be given an injection of LPS, positive controls for an inflammatory reaction.

3*"Env" for the batch which will be injected with a solution of the envelope protein of the MSRV virus.

4*"2GR412" for the batch which will be infected with the MSRV virus inactivated by heating for 30 min at 56° C. (to test the effect of the envelope protein of the virion, in the absence of viral replication).

4*"GRE" for the batch which will be infected with the GRE virus that has been heat-inactivated and highly diluted in negative control (to evaluate any possible effect of contamination of a biological sample with this virion, in the case of blood pools for the transfusion of derived products containing a viremic donor).

The mice of each batch are infected with a suitable volume of solution in a single IP administration (the amounts of LPS and of Env correspond to the concentration used for the assays on PBMCs). The solutions will be titered in the following way: "LPS": 50 µg/mouse; "Env": 50 µg/mouse (injection of 500 µl; "2GR412" and "GRE": 100 µl of the ultracentrifugation pellet/mouse.

All the necessary dilutions are prepared in sterile physiological saline.

Observations and Samples:

D+1 h/D+2h/D+24h/D3: sacrifices and samples.

In each group, one mouse is sacrificed. 2 ml of physiological saline are injected IP, the abdomen is tapped, and the maximum amount of liquid is withdrawn (1-1.5 ml maximum). The suspension is centrifuged (6000 rpm/10 min/AT) in order to remove the possible cell pellet, and frozen at −80° C. in an Eppendorf tube.

The maximum amount of blood is taken via the retroorbital route, with a Pasteur pipette, into a heparin tube. The blood is centrifuged at 6000 rpm, 10 min, AT. The plasma and the cell pellet are recovered and frozen separately in an Eppendorf tube at −80° C.

The removed spleen is divided into two fragments. One part is made into a suspension (in order to carry out the human and murine phenotyping thereof by FACs): grinding on a screen in approximately 10 ml of RPMI, centrifugation at 1200 rpm/4° C./10 min, washing with approximately 15 ml of PBS/4° C. and then centrifugation, and freezing in a cryotube in 1 ml of freezing solution (10% DMSO-90% FCS), and another part is frozen, as it is, in a Eppendorf at −80° C. (for a possible PCR).

This process is carried out after 24 h and 48 h, unless clinical signs have appeared earlier (the mice are monitored and recovered just before death). For the remaining two mice of the "2GR412" and "GRE" batches, they are sacrificed after 15-20 days or recovered immediately after their death if this occurs earlier.

This distribution of samples makes it possible to cover the immediate (2 h), early (24 h) and delayed (10-15 days) immune reactions.

The samples of biological fluids are assayed for human and murine cytokines (Il-6 and TNFα) and are also assayed for the "Env" protein and/or titered with respect to the virus, by ELISA and by bioassay on cell cultures.

The analyses make it possible to evaluate the immune reaction: inflammation (cytokines) and cell distribution (FACS), and to search for any viral replication (ELISA, bioassay).

Clinical Observations

All the mice are observed clinically until the end of the experiment. Signs of inflammation and signs of neurological damage are particularly noted.

Results:

The aim of this section is to study in vivo on a humanized SCID model, the properties of Env-SU by virtue of the parameters determined by means of a feasibility study carried out beforehand.

Pro-inflammatory Effects of Env-SU on Cultures of PBMCs

Initially, we studied the kinetics of production of TNF-alpha induced by Env-SU and LPS in a culture of human PBMCS. The proteins and toxins were used at a concentration of 1 µg/ml (FIG. 16). We can observe that the production of cytokine reaches a peak at 2 h post-injection and then gradually decreases to become zero after 48 h. The detection of TNF-alpha post-injection with Env-SU is very significant. Specifically, the cells incubated with buffer produce only a very small production of TNF-alpha, barely reaching 30 pg/ml at 2 h. The stimulation with Env-SU produces a production of 550, 350, then 160 pg/ml at, respectively, 2 h, 24 h and 48 h post-stimulation. The action of LPS is slightly greater, producing a production of 650, 180, then 50 pg/ml at 2 h, 24 h and 48h. This study made it possible to confirm the pro-inflammatory properties of the Env-SU protein on PBMCs, as already shown. It also makes it possible to observe that the production of TNF-alpha is at a maximum 2 h post-injection. These data make it possible to define the kinetics of sampling to be adopted for the study on the SCID model, namely 2 h, 24 h and 48 h.

Pro-inflammatory Effects of Env-SU in the Humanized SCID Mouse (SCID-h)

After having observed the pro-inflammatory effects caused by the Env-SU protein on various human and murine cell cultures, we evaluated, in vivo, the pathogenicity of these same substances on SCID-hu mice. A group of 16 mice was grafted, IP, with 50×10$^6$ human PBMCs after having been given 50 microliters of anti-NK via the retroorbital route. One week later, blood was taken from each mouse in order to assay the human IgGs in their serum, with the aim of validating the humanization of the mice. We were able to determine, by radial immunodiffusion assay, that the concentration of human IgGs in the serum of all the SCID-hu mice was much higher than 4.5 mg/l. The IgG half-life in an SCID-hu mouse is 12 days. In our case, we can therefore assert that the humanization of the mice was successful.

The mice are then divided up into five batches, each batch comprise three mice injected with, respectively, 0.2 ml of buffer, 50 µg of Env-SU or 50 µg of LPS, diluted in 2 ml of physiological saline. One of the mice of each batch were sacrificed at 2 h, 24 h and 48 h after the injections. All the mice remained alive and no outside sign of the nervous system being affected was visible up until their sacrifice.

The human and murine TNF-alpha and IL-6 cytokines were assayed by ELISA. The results in FIG. 17 show that the production of human or murine cytokines follows the same tendency: it is abruptly detected at 2 h post-injection, and then it becomes zero over the following days. Overall, these kinetics are identical to those observed in vitro on PBMCs. The mice injected with buffer show no significant production of cytokines. The assaying of murine TNF-alpha reveals only one large peak: the mouse having been given LPS shows a TNF-α level greater than 1000 pg/ml in its serum. As regards the assaying of murine IL-6, a level of approximately 20 000 pg/ml is reached in the IP fluid of the mice injected with Env or LPS. The concentrations found in the serum of these mice reach, respectively, 6200 pg/ml and more than 20 000 pg/ml.

The assaying of the human cytokines reveals cytokine detection in the IP fluid that is higher than in the serum. This is because, since the mice were grafted only about ten or so days before the administration of the proteins and toxins, the PBMCs have had only a short period of time to migrate and colonize the spleen and the secondary lymphoid organs (the amount of migrating cells remains relatively low). Furthermore, Env-SU mainly targets monocytes, which differentiate rapidly to macrophages in the tissues. These cells are very adherent and will preferentially "stick" to the peritoneum rather than colonizing the secondary lymphoid organs. It therefore appears to be logical to find a greater production of cytokines at the very site of grafting of the cells, in the intraperitoneal (IP) cavity.

The human TNF-α assay reveals a concentration reaching 1400 pg/ml, IP, for the mouse injected with Env-SU and 3000 pg/ml, IP, and also 1200 pg/ml in the serum for the mouse injected with LPS. The same tendencies are observed for the IL-6 assay, with 1700 pg/ml detected IP in the mouse injected with Env-SU and 9600 pg/ml and 1400 pg/ml, respectively, IP and in the serum of the mouse injected with LPS.

The decision to assay the murine cytokines in SCID-hu mice may appear to be surprising, since the latter lack T and B lymphocytes. However, the monocyte-macrophage population remains active and contributes to the production of TNF-α and IL-6 in these mice. Thus, it is shown that the murine IL-6 concentrations detected are always greater than the human IL-6 concentrations, which is not the case for TNF-α. The latter point therefore perfectly illustrates, in vivo, the direct effect of the MSRV envelope on the innate immunity component, in the absence of functional lymphocytes in this SCID model (for the murine component).

The object of this study was to evaluate, in vivo, the pathogenicity associated with the recombinant envelope protein, Env-SU, after having provided proof of a pathogenicity effect in vitro on human PBMCs. The pro-inflammatory effects of the Env-SU protein and of LPS, characterized by a massive and isolated production (2 h post-injection) of TNF-α and/or of IL-6, are observed in the SCID-hu mice. Subsequent to the results obtained, it is possible to validate the experimental protocols for taking samples and for analyzing the cytokine production (in the serum and by IP lavage) for use on the humanized SCID mice, as developed on a murine model in a prior "technical" feasibility study on C57B16 mice.

EAE Model

The EAE model is an animal model of multiple sclerosis based on the induction, peripherally, of an autoimmunity directed against myelin determinants.

This model is, to date, the reference model used for all the protocols for "preclinical" validation of therapeutic molecules intended for the treatment of multiple sclerosis.

This model is characterized by the presence of autoreactive T lymphocytes and demyelination resulting in serious neurological symptoms.

The development thereof is conventionally based on the injection of C57b16 mice with a myelin peptide coupled to a suitable adjuvant (complete Freund's adjuvant), associated with an injection of pertussis toxin.

The adjuvant, which is composed of inactivated mycobacteria, allows the tolerance against the injected myelin to be broken and promotes the development of autoreactive T lymphocytes.

The pertussis toxin promotes opening of the blood-brain barrier but also plays a role in the breaking of tolerance.

It was shown that Env-SU activated the innate immune system via the TLR4 receptor and was capable of inducing the development of Th1 type lymphocyte responses. Env-SU could therefore play the role of an adjuvant for triggering the mechanisms of autoimmunity and of demyelination associated with MS. This potential role was studied in the EAE model.

Three different experiments were carried out.

1—Preliminary Experiment

Materials and Methods

The active ingredient of complete Freund's adjuvant (inactivated mycobacteria) normally used for the multiple sclerosis model "EAE" conventionally implemented was replaced with the Env-SU fraction of the MSRV envelope protein.

Material

Eight C57B16 mice (Charles River).
Myelin peptide MOG (myelin oligodendrocyte glycoprotein) 35-55 immunograde from Neosystem.
Complete Freund's adjuvant (CFA) from SIGMA.
Incomplete Freund's adjuvant (IFA) from SIGMA.
Pertussis toxin (salt free *bordetella pertussis*) from Calbiochem.
Env-SU from Protein Expert.

Method

Subcutaneous injection of 200 µl of:
Positive control:
150 µg MOG+CFA: 3 mice tested.
Negative control:
150 µg MOG+IFA: 2 mice tested.
Env-SU:
150 µg MOG+IFA+Env-SU (50 µg): 3 mice tested;

then injection of 200 µl (IV) of pertussis toxin (200 ng) at D0 and D2.

The neurological signs are then measured daily.

The various stages are listed below according to the neurological signs observed.

Stage 0 signifies no clinical signs,
stage 1 signifies soft tails,
stage 2 signifies problems walking,
stage 3 signifies partial paralysis of the rear limbs,
stage 4 signifies total paralysis of the rear limbs,
stage 5 signifies paralysis of the rear limbs and partial paralysis of the front limbs,
stage 6 signifies moribund or dead animals.

Results:

MOG (150 µg)+CFA: 2 mice out of 3 developed the disease (stage 4).
MOG (150 µg)+IFA: no sign observed.
MOG (150 µg)+Env-SU (50 µg): 3 mice out of 3 developed the disease (stages 1 to 6).

The results of the preliminary study are represented in FIG. 18.

This preliminary study shows that Env-SU, which activates the immune system via the TLR4 receptor, can be used as an adjuvant for the development of the MS model, EAE.

The positive control with a "conventional" adjuvant (CFA) validates the experiment. The negative control with an incomplete adjuvant that has no potential for inducing autoimmunity (IFA) validates the need to stimulate the immune system according to specific pathways in order to induce an autoimmune reaction.

Thus, right from this preliminary stage, it is obvious that the Env protein of the MSRV/HERV-W retrovirus is therefore clearly capable of causing an autoimmune sensitization with an effect on the central nervous system like the "experimental" adjuvant currently used for the EAE model.

The major difference with CFA, the active ingredient of which is a lysate of *Mycobacterium tuberculosis*, is that this bacterium is in no way associated with multiple sclerosis in humans, whereas the MSRV retrovirus and its genetic analogs of the HERV-W family are clearly associated with multiple sclerosis in humans [2, 7, 8, 10, 61-63]. Furthermore, the expression and the circulation in the biological fluids of the virions bearing this envelope protein correlates with the progression of the disease [10].

Consequently, and right from this preliminary stage, it is obvious that any therapeutic agent capable of inhibiting the "autoimmunity-inducing" immunological potential of the Env envelope protein of this retroviral family is particularly advantageous, what is more if it has been selected for its inhibitory activity with respect to the anti-inflammatory effects as described in the present invention with the in vitro cell assays. In fact, the monoclonal antibodies directed against the MSRV/HERV-W Env proteins are implicitly inhibitors of the "autoimmunity-inducing" effects of these proteins when they are expressed at the surface of the virions detectable in patients suffering from MS [8, 10, 62]. Their use in human therapy is obvious and technically within the scope of those skilled in the art, according to known methods for therapeutic antibodies currently authorized and sold for human therapy, such as the anti-TNF alpha antibody sold under the name REMICADE which is prescribed for the treatment of rheumatoid arthritis in particular. It is interesting, in addition, to note here that this therapeutic antibody, which is commercially available, targets a "downstream" product of the pro-inflammatory activation cascade, whereas, according to the invention, the therapeutic target is inhibited well before the induction of TNF-α, in particular via TLR4.

It is also important to note that the therapeutic agents currently proposed in MS therapy (corticosteroids, interferon beta, or the like) act on only a limited portion of the pro-inflammatory components produced subsequent to the initiation of the immunopathological cascade, which explains their partial and relative effectiveness in the treatment of patients.

On the other hand, by inhibiting the primary effect of the MSRV/HERV-W Env protein before activation of the TLR4 receptor pathway and therefore of the innate immunity involved in this initial phase, the only immunopathogenic agonist present at this stage is inhibited, which is no longer the case with the multitude of pro-inflammatory products secreted after primary activation of this pathway (FIG. 8). This "biological" advantage provides a unique potential for effectiveness in the patients, all the more so since it targets a "key" agent in the etiopathogenesis of MS, and not just one of the by-products of activation for which the effectiveness was measured in an EAE model induced with the tuberculosis agent (*M. tuberculosis* in complete Freund's adjuvant) which has nothing) to do with the human disease MS.

2—Experiment 2

The same type of experiment was carried out in order to confirm the preliminary results observed.

Method
    Subcutaneous injection with 200 µl of:
    MOG (150 µg)+CFA: 4 mice tested.
    MOG (150 µg)+IFA: 3 mice tested.
    MOG (150 µg)+IFA+Env-SU (50 µg): 4 mice tested.
    MOG (150 µg)+IFA+LPS (20 µg): 4 mice tested;

and then injection of 200 µl (IV) of pertussis toxin (200 ng) at D0 and D2.

Measurement of the Clinical Signs

The spleens of all the mice were subsequently recovered and then cell suspensions were frozen.

The brains of 2 mice were recovered and then frozen after perfusion with 4% PFA (brain of one Env mouse stage 3; brain of one LPS mouse stage 0).

Characteristic inflammatory lesions were visualized by histological analysis in the brain of the mice having been given the Env protein and not in that of the mouse having been given the injection of LPS.

Results:
    Monitoring of the Neurological Signs:
    MOG (150 µg)+CFA: 4 mice out of 4 developed the disease (stages 2 to 6).
    MOG (150 µg)+IFA: no sign observed.
    MOG (150 µg)+Env-SU (50 µg): 4 mice out of 4 developed the disease (stages 1 to 5).
    MOG (150 µg)+LPS (20 µg): no sign observed.

The results are illustrated in FIG. 19.

These results confirm that Env-SU can have an adjuvant role in the induction of the neurological signs observed during the development of the MS model represented by EAE.

In addition to the above controls LPS (bacterial lipopolysaccharide) was used, since it stimulates the same receptor at the surface of antigen-presenting cells as the MSRV Env protein: TLR4. The absence of autoimmunity-inducing effect of LPS under these conditions shows that the immunological potentiality of the Env protein is much greater than that of other TLR4 ligands and that, logically, an inhibitor that targets this protein will be a better therapeutic tool than molecules that nonspecifically inhibit certain pathways activated by the latter.

Functional Studies:

The spleens were thawed and the splenocytes were then restimulated with MOG peptide in vitro, and then the production of IFN-g was measured (kinetics and dose response).

$2 \times 10^6$ splenocytes/ml of c-RPMI+10% FCS.

The means of 3 mice for Env and 2 for IFA and LPS are presented.

FIG. 20 illustrates the response as a function of the dose of MOG (dose effect), by means of the dosage of interferon gamma which signals the activation of T lymphocytes in the presence of the specific autoantigen and clearly shows that a real autoimmune response is induced in this model by the MSRV-HERV-W Env protein, using the Env-SU fragment which specifically stimulates the TLR-4 pathway under these conditions. In this model of MS, the T lymphocyte response does not result from direct activation by MSRV/HERV-W Env, for example via the T receptor (TCR), as in the case of a superantigen, but from activation much further upstream, at the level of the cells of innate immunity (monocytes/macrophages, dendritic cells, etc.), as shown by the numerous results of the present invention (absence of IFN-gamma secretion, stimulation of purified monocytes and dendritic cells, stimulation of murine "macrophagic" cytokines in the SCID model which does not comprise any functional murine lymphocytes, IL-6 kinetics parallel to those of LPS, absence of IL-6 and TNF-alpha but clearly interferon gamma induced under the same conditions by a reference superantigen -SEB-, etc.).

This is also confirmed by the study of the kinetics, over time, of the autoimmune T lymphocyte response against the myelin antigen MOG added at 10 micrograms/ml to the culture medium used to test the splenocytes taken from the "EAE/MOG/Env-SU" animals and the "Env-free" controls with incomplete Freund's adjuvant (IFA, without *M. tuberculosis* extract) and MOG. This is illustrated by FIG. 21, which shows the very significant progression of the anti-MOG autoimmune response over time in the only mice to have been given Env-SU.

These results therefore clearly show that a stimulation with Env-SU associated with an autoantigen allows, downstream of the cascade initiated by Env-SU at the level of the TLR4 receptor on the antigen-presenting cells (APCs, which include monocytes/macrophages, dendritic cells, brain microgliocytes, etc.), the development of autoreactive T lymphocytes which are the sole cause of the interferon gamma (IFN-g) released in very high amounts (see graph) and therefore of an autoimmunity mediated by these T lymphocytes in vivo.

3—Experiment 3

The same type of experiment was carried out in order to confirm the preliminary results observed, but also to test, in vivo, the therapeutic effects (on the clinical consequence measured in the model) of the anti-Env-SU antibodies (represented here by the monoclonal antibody 3B2H4), in parallel with antibodies of the same isotype but not with an equivalent specificity (represented here by the anti-GAG monoclonal antibody 3H1H6).

Method

Subcutaneous injection of a dose of 200 microliters of antibodies at 5 micrograms/ml, i.e. 1 microgram of antibodies per mouse weighing approximately 20 grams, i.e. of 50 micrograms per kg:

MOG (150 µg)+CFA: 5 mice tested.
35.
MOG (150 µg)+IFA: 5 mice tested.
MOG (150 µg)+IFA+Env-SU (50 µg): 5 mice tested.
MOG (150 µg)+IFA+Env-SU (50 µg): 5 mice tested. These mice were also given 1 mg of Ab 3B2H4, IV (200 µl);

then injection of 200 µl (IP) of pertussis toxin (200 ng) at D0 and D2 and measurement of the clinical signs.

Results:

The results obtained are illustrated in FIG. 22.

In order to test conditions closer to the development of a progressive autoimmunity as in MS, the results are obtained under conditions that are more "moderate" than the previous ones, since the toxin was injected IP and not IV as previously.

The "MOG+CFA" positive control corresponds here to 4/5 mice with clinical signs, and the "MOG+IFA" negative control corresponds to 0/5 mice affected.

With the Env protein, as with the "MOG+CFA" positive controls, the mean clinical score is here reduced compared with the previous conditions. However, the net reduction in the pathogenic effect of this protein in the presence of anti-Env antibodies is illustrated by the minimum damage observed in the treated mice.

It is thus noted that the "anti-Gag" antibody has no inhibitory effect on the immunopathological effect induced by the Env protein, or even slightly potentiates this effect through its presence, whereas the antibody 3B2H4 has a very clear inhibitory effect which causes the curve observed to move the most toward that of the "MOG+CFA" negative controls. The in vivo inhibitory effect of the "T lymphocyte-mediated autoimmunity-inducing" effects of EAE type is therefore linked to the presence of the anti-MSRV/HERV-W Env antibody through 3B2H4.

In the multiple sclerosis model "EAE", it is the clinical effects (neurological damage) which are measured, in particular, and not only the associated biological parameters. The effect studied is therefore no longer only a biological effect as described above, but the clinical translation thereof in the context of a dedicated pathological model. Therefore, what is measured here is indeed a therapeutic effect. Now, it is well known to those skilled in the art that these are the qualitative limits of the "preclinical" therapeutic validation for human therapy, since any subsequent therapeutic validation on the human disease must be carried out on humans on the basis of the criteria obtained on an animal model.

Once the candidate therapeutic agents have been identified and selected and the dedicated animal models developed and validated, as in the present invention, a "quantitative" extension of the test series carried out can implicitly be carried out, developing the tools and the models already obtained with suitable controls well known to those skilled in the art and common to pharmacological studies, in order to satisfy the preclinical criteria.

The elements obtained are therefore necessary and sufficient to finalize the preclinical validations and develop a therapeutic experimentation in humans.

Moreover, the analysis of the amino acid sequence of the MSRV ENV (SEQ ID NO: 5) and HERV-W7q ENV (syncitin)(SEQ ID NO: 4) proteins shows the strong homology and the conservation of the main amino acid motifs in the MSRV/HERV-W family (FIG. 23). This is reflected by a cross reactivity with the anti-ENV monoclonal antibodies (FIG. 24).

The sequence analysis (cf. FIG. 25) also makes it possible to evaluate antigenic regions of interest in the sequence of the ENV-SU protein referenced in SEQ ID NO: 1, corresponding to the regions defined by amino acids 122-131 (inclusive) and/or 312-316 (inclusive) and/or 181-186 (inclusive) of SEQ ID NO: 3.

Consequently, it has been confirmed, in this animal model of MS, that a monoclonal antibody directed against the Env envelope protein of retroviruses of the MSRV/HERV-W family, and in particular of its prototype member MSRV, especially selected for its inhibitory properties on the pro-inflammatory pathway initiated by the TLR4 receptor in a cell assay, constitutes a therapeutic agent capable of inhibiting the immunopathological potential, in particular "autoimmunity-inducing" immunopathological potential, of the ENV envelope protein of this retroviral family.

It has therefore now been proved that:

1) Enveloped MSRV virions are detected in patients suffering from multiple sclerosis [4, 8, 10, 62, 64].
2) Their expression correlates with the evolution of the disease [10].
3) The immunological response to the MSRV Env protein correlates with the progression and the severity of the disease [65].
4) The MSRV virions possess an RNA encoding the MSRV Env protein [66].
5) The Env proteins of the MSRV/HERV-W family have a very strong homology at the level of their amino acid sequence and at the level of the genetic sequences which encode them [2, 5, 66].
6) The MSRV Env protein and the Env protein encoded by the HERV-W copy in the region of human chromosome 7q21-22 (HERV-W7q) have pro-inflammatory properties in vitro and in vivo (examples of the present patent application and [11, 12, 59]).
7) The MSRV Env protein is capable of reproducing the well known model of multiple sclerosis (MS), namely experimental allergic encephalomyelitis (EAE), in the presence of an autoantigen of the central nervous system derived from myelin (myelin oligodendrocyte glycoprotein, MOG, example of the present patent application).
8) This experimental model is conventionally initiated artificially with an antigenic extract of Mycobacterium tuberculosis, the bacterial agent for tuberculosis, which has nothing to do with the etiology of human multiple sclerosis. The obtaining of this model with the envelope protein of the MSRV retrovirus, belonging to the endogenous retroviral family HERV-W, the expression of which can be detected in correlation with the disease, in the form of virions [8, 10, 62] or in the form of Env protein specifically expressed in the demyelination lesions characteristic of MS [59, 67], constitutes a novel and unique animal model which makes it possible to study the therapeutic agents that target a retroviral agent involved in the immunopathogenesis of the disease.

9) The pro-inflammatory effects associated with the activation of T lymphocytes described on human cells are also clearly found at the level of the murine T lymphocytes of the EAE model induced with the MSRV Env protein, as attested to by the assays for interferon gamma production (example of the present patent application)

10) The pro-inflammatory effects of the MSRV Env protein are mediated by lymphoid cells and antigen-presenting cells, and therefore by the immune system (examples of the present patent application, [11, 12]).

11) Anti-MSRV Env monoclonal antibodies (3B2H4 and 13H5A5) are capable of specifically inhibiting the pro-inflammatory effects of the MSRV Env protein on human blood lymphoid cells (lymphocytes and monocytes (examples of the present patent application).

12) The "specific inhibitory" effect of a monoclonal antibody (3B2H4) directed against the MSRV Env protein is confirmed in the animal model of EAE induced with MSRV ENV. This effect is reflected by a notable clinical improvement of the animals treated compared with the nontreated animals or animals treated with an irrelevant antibody of the same isotype (example of the present patent application).

The anti-MSRV/HERV-W Env monoclonal antibodies can therefore have an inhibitory effect on the inflammation, on the autoimmunity and on the neurological clinical problems induced with such a protein of a retroviral agent associated with the disease.

It is therefore obvious that the antibodies whose properties were verified in vitro and in vivo constitute novel therapeutic agents for the human disease, multiple sclerosis, in an unmodified form or in a form improved by biological techniques, in particular genetic engineering techniques.

The cell assays and the animal models suitable for the preclinical evaluation of these therapeutic antibodies are described here and now allow those skilled in the art to carry out the required validation steps before the therapeutic trials in humans and to adjust them to various pathologies associated with the MSRV/HERV-W retroviral family.

BIBLIOGRAPHICAL REFERENCES

1. Conrad. B., et al., *A human endogenous retroviral superantigen as candidate autoimmune gene in type I diabetes.* Cell, 1997, 90(2); p. 303-13.
2. Perron, H., et al., *Molecular identification of a novel retrovirus repeatedly isolated from patients with multiple sclerosis. The Collaborative Research Group on Multiple Sclerosis.* Proc Natl Acad Sci USA, 1997. 94(14): p. 7583-8.
3. Deb-Rinker, P., et al., *Molecular characterization of a MSRV-like sequence identified by RDA from monozygotic twin pairs discordant for schizophrenia.* Genomics, 1999. 61(2): p. 133-44.
4. Perron, E., et al., *Isolation of retrovirus from patients with multiple sclerosis [letter].* Lancet, 1991. 337(8745): p. 862-3.
5. Blond, J. L., et al., *Molecular characterization and placental expression of HERV-W, a new human endogenous retrovirus family.* J Virol, 1999. 73(2): p. 1175-85.
6. Perron, H., et al., *Particle-associated retroviral RNA and tandem RGH/HERV-W copies on human chromosome 7q: possible components of a 'chain-reaction' triggered by infectious agents in multiple sclerosis?* J Neurovirol, 2000. 6(Suppl 2): p. S67-75.
7. Dolei, A., et al., *Multiple sclerosis-associated retrovirus (MSRV) in Sardinian MS patients.* Neurology, 2002. 58(3): p. 471-3.
8. Garson, J. A., et al., *Detection of virion-associated MSRV-RNA in serum of patients with multiple sclerosis [letter] [see comments].* Lancet, 1998. 351(9095): p. 33.
9. Olsson, P., et al., *Retroviral RNA related to ERV9/MSRV in a human serum: a new sequence variant.* AIDS Res Hum Retroviruses, 1999. 15(6): p. 591-3.
10. Sotgiu, S., et al., *Multiple sclerosis-associated retrovirus and MS prognosis: an observational study.* Neurology, 2002. 59(7): p. 1071-3.
11. Perron, H., et al., *Multiple sclerosis retrovirus particles and recombinant envelope trigger an abnormal immune response in vitro, by inducing polyclonal Vbeta16 T-lymphocyte activation.* Virology, 2001. 287(2): p. 321-32.
12. Firouzi, R., et al., *Multiple Sclerosis Associated Retrovirus Particles Cause T-Lymphocyte Dependent Death with Brain Hemorrhage, in* Humanized SCID Mice Model. Journal of Neurovirology, 2003. 9: p. 79-93.
13. Lin, A., et al., *The inflammatory response system in treatment-resistant schizophrenia: increased serum interleukin-6.* Schizophr Res, 1998. 32(1): p. 9-15. 6: Stevens J R. Neuropathology of schizophren . . . [PMID: 7125843] Related Articles, Links.
14. Karlsson, H., et al., *Retroviral RNA identified in the cerebrospinal fluids and brains of individuals with schizophrenia.* Proc Natl Acad Sci USA, 2001. 98(8): p. 4634-9.
15. Perron, H., *Microbial Agents triggering Endogenous Retroviruses within Genetic Susceptibility Loci, Resulting in Expression of Superantigen and Gliotoxic Molecules: a Plausible a "Immunovirogenetic" Cascade causing Multiple Sclerosis?* Modern Aspects of Immunobiology, 2001. 1(5): p. 198-203.
16. Liu, Y., et al., *Dextromethorphan protects dopaminergic neurons against inflammation-mediated degeneration through inhibition of microglial activation.* J Pharmacol Exp Ther, 2003. 305(1): p. 212-8. 2: Gao H M et al. Synergistic dopaminergic neur . . . [PMID: 12598611] Related Articles, Links.
17. Morimoto, K., T. Murasugi, and T. Oda, *Acute neuroinflammation exacerbates excitotoxicity in rat hippocampus in vivo.* Exp Neurol, 2002. 177(1): p. 95-104. 5: Stoll G. Inflammatory cytokines in the . . . [PMID: 12407295] Related Articles, Links.
18. Guillemin, G. J. and B. J. Brew, *Applications of the kynurenine pathway and quinolinic acid in Alzheimer's disease.* Redox Rep, 2002. 7(4): p. 199-206. 7: Kim E J et al. Neuroprotective effects of pr . . . [PMID: 12237868] Related Articles, Links.
19. Kim, W. G., et al., *Regional difference in susceptibility to lipopolysaccharide-induced neurotoxicity in the rat brain: role of microglia.* J Neurosci, 2000. 20(16): p. 6309-16. 15: Czlonkowska A et al. Inflammatory changes in the s . . . [PMID: 10894230] Related Articles, Links.
20. Licinio, J. and M. L. Wong, *The role of inflammatory mediators in the biology of major depression: central nervous system cytakines modulate the biological substrate of depressive symptoms, regulate stress-responsive systems, and contribute to neurotoxicity and neuroprotection.* Mol Psychiatry, 1999. 4(4): p. 317-27. 18: Cotter R L et al. Insights into the neurodegene . . . [PMID: 10204569] Related Articles, Links.
21. Cotter, R. L., et al., *Insights into the neurodegenerative process of Alzheimer's disease: a role for mononuclear phagocyte-associated inflammation and neurotoxicity.* J Leukoc Biol, 1999. 65(4): p. 416-27. 19: Heese K et al. Inflammatory signals induce n . . . [PMID: 9453564] Related Articles, Links.
22. Heese, K., C. Hock, and U. Otten, *Inflammatory signals induce neurotrophin expression in human microglial cells.* J Neurochem, 1998. 70(2): p. 699-707. 20: Sasser L B et al. Subchronic toxicity evaluation. [PMID: 8600286] Related Articles, Links.
23. Chao, C. C., et al., *Interleukin-1 and tumor necrosis factor-alpha synergistically mediate neurotoxicity: involvement of nitric oxide and of N-methyl-D-aspartate receptors.* Brain Behav Immun, 1995. 9(4): p. 355-65. 22: Chao C C et al. Tumor necrosis factor-alpha p . . . [PMID: 7705222] Related Articles, Links.
24. Chao, C. C. and S. Hu, *Tumor necrosis factor-alpha potentiates glutamate neurotoxicity in human fetal brain cell cultures.* Dev Neurosci, 1994. 16(3-4): p. 172-9.
25. Bal-Price, A. and G. C. Brown, *Inflammatory neurodegeneration mediated by nitric oxide from activated glia-inhibiting neuronal respiration, causing glutamate release and excitotoxicity.* J Neurosci, 2001. 21(17): p. 6480-91. 5: Obrenovitch T P. Quinolinic acid accumulation . . . [PMID: 11462760] Related Articles, Links.
26. Obrenovitch, T. P., *Quinolinic acid accumulation during neuroinflammation. Does it imply excitotoxicity?* Ann N Y Acad Sci, 2001. 939(1-10.): p. Law A et al. Say NO to Alzheimer's disease . . . [PMID: 11245887] Related Articles Links.
27. Werner, P., D. Pitt, and C. S. Raine, *Glutamate excitotoxicity—a mechanism for axonal damage and oligodendrocyte death in Multiple Sclerosis?* J Neural Transm Suppl, 2000(60): p. 375-85. 8: Pitt D et al. Glutamate excitotoxicity in a . . . [PMID: 10613826] Related Articles, Links.
28. Pitt, D., P. Werner, and C. S. Raine, *Glutamate excitotoxicity in a model of multiple sclerosis.* Nat Med, 2000. 6(1): p. 67-70. 9: Carlson N G et al. Inflammatory cytokines IL-1 a . . . [PMID: 10490998] Related Articles, Links.
29. Carlson, N. G., et al., *Inflammatory cytokines IL-1 alpha, IL-1 beta, IL-6, and TNF-alpha impart neuroprotection to an excitotoxin through distinct pathways.* J Immunol, 1999. 163(7): p. 3963-8. 10: Wang Y S et al. The bacterial endotoxin lipop . . . [PMID: 9930737] Related Articles, Links.
30. Wang, Y. S. and T. D. White, *The bacterial endotoxin lipopolysaccharide causes rapid inappropriate excitation in rat cortex.* J Neurochem, 1999. 72(2): p. 652-60. 11: Chao C C et al. Tumor necrosis factor-alpha p . . . [PMID: 7705222] Related Articles, Links.
31. Yolken, R. E., et al., *Endogenous retroviruses and schizophrenia.* Brain Res Brain Res Rev, 2000. 31(2-3): p. 193-9.
32. Kleine, T. O., et al., *Approach to discriminate subgroups in multiple sclerosis with cerebrospinal fluid (CSF) basic inflammation indices and TNF-alpha, IL-1beta, IL-6, IL-8'.* Brain Res Bull, 2003. 61(3): p. 327-46. 2: Aarli J A. Role of cytokines in neurolog . . . [PMID: 12871095] Related Articles, Links.
33. Aarli, J. A., *Role of cytokines in neurological disorders.* Curr Med Chem, 2003. 10(19): p. 1931-7. 3: Vladic A et al. Cerebrospinal fluid and serum . . . [PMID: 12445803] Related Articles, Links.
34. Miljkovic, D., et al., *Nitric oxide metabolites and interleukin-6 in cerebrospinal fluid from multiple sclerosis patients.* Eur J Neurol, 2002. 9(4): p. 413-8. 5: Clerici M et al. Single-cell analysis of cytok . . . [PMID: 11730945] Related Articles, Links.
35. Fedetz, M., et al., *The −174/−597 promoter polymorphisms in the interleukin-6 gene are not associated with susceptibility to multiple sclerosis.* J Neurol Sci, 2001. 190(1-2): p. 69-72. 7: Stelmasiak Z et al. IL-6 and sIL-6R concentration . . . [PMID: 11535934] Related Articles, Links.
36. Vandenbroeck, K., et al., *High-resolution analysis of IL-6 minisatellite polymorphism in Sardinian multiple sclerosis: effect on course and onset of disease.* Genes Immun, 2000. 1(7): p. 460-3. 9: Stelmasiak Z et al. Interleukin-6 concentration i . . . [PMID: 11208463] Related Articles, Links.
37. Stelmasiak, Z., et al., *Interleukin-6 concentration in serum and cerebrospinal fluid in multiple sclerosis patients.* Med Sci Monit, 2000. 6(6): p. 1104-8. 10: Schonrock L M et al. Interleukin-6 expression in h . . . [PMID: 110445B3] Related Articles, Links.
38. Cornford, E. M. and M. E. Cornford, *New systems for delivery of drugs to the brain in neurological disease.* Lancet Neurol, 2002. 1(5): p. 306-15. 4: Schmidt J et al. Drug targeting by long-circul . . . [PMID: 12805101] Related Articles, Links.
39. Schmidt, J., et al., *Drug targeting by long-circulating liposomal glucocorticosteroids increases therapeutic efficacy in a model of multiple sclerosis.* Brain, 2003. 126(Pt B): p. 1895-904. 5: Fournier E et al. Therapeutic effectiveness of . . . [PMID: 12767096] Related Articles, Links.
40. Pardridge, W. M., *Blood-brain barrier drug targeting enables neuroprotectlon in brain ischemia following delayed intravenous administration of neurotrophins.* Adv Exp Ned Biol, 2002. 513(397-430.): p. Watanabe S et al. Chemotherapeutic targeting of . . . [PMID: 12575735] Related Articles, Links.
41. Watanabe, S., et al., *Chemotherapeutic targeting of etoposide to regions of the brain on the basis of polyamine level.* J Drug Target, 2002. 10(6): p. 457-61. 13: Lahiri D K et al. A critical analysis of new mo . . . [PMID: 12558063] Related Articles, Links.
42. Scherrmann, J. M., *Drug delivery to brain via the blood-brain barrier.* Vascul Pharmacol, 2002. 38(6): p. 349-54. 15: Wang J X et al. Enhanced brain targeting by s . . . [PMID: 12445558] Related Articles, Links.
43. Wang, J. X., X. Sun, and Z. R. Zhang, *Enhanced brain targeting by synthesis of 3',5'-dioctanoyl-5-fluoro-2'-deoxyuridine and incorporation into solid lipid nanoparticles.* Eur J Pharm Biopharm, 2002. 54(3): p. 285-90. 16: Mahar Doan K M et al. Passive permeability and P-gl . . . [PMID: 12438524] Related Articles, Links.
44. Hosoya, K., S. Ohtsuki, and T. Terasaki, *Recent advances in the brain-to-blood efflux transport across the blood-brain barrier.* Int J Pharm, 2002. 248(1-2): p. 15-29. 18: Mora M et al. Design and characterization o . . . [PMID: 12425459] Related Articles, Links.
45. Mora, M., et al., *Design and characterization of liposomes containing long-chain N-acylPEs for brain delivery: penetration of liposomes incorporating GM1 into the rat brain.* Pharm Res, 2002. 19(10): p. 1430-8.
46. Perron, H., et al., *Herpes simplex virus ICP0 and ICP4 immediate early proteins strongly enhance expression of a retrovirus harboured by a leptomeningeal cell line from a patient with multiple sclerosis.* J Gen Virol, 1993. 74(Pt 1): p. 65-72.
47. Soldan, S., et al., *Association of human herpes virus 6 (HHV-6) with multiple sclerosis: increased IgM response to HHv-6 early antigen and detection of serum HHV-6 DNA.* Nat Med, 1997. 3: p. 1394-1397.
48. Haahr, S., et al., *Is multiple sclerosis caused by a dual infection with retrovirus and Epstein-Barr virus?* Neuroepidemiology, 1992. 11(4-6): p. 299-303.

49. Bergstrom, T., O. Andersen, and A. Vahlne, *Isolation of herpes simplex virus type I during first attack of multiple sclerosis*. Ann Neurol, 1989. 26: p. 283-285.

50. Marx, C. E., et al., *Cytokine effects on cortical neuron MAP-2 immunoreactivity: implications for schizophrenia*. Biol Psychiatry, 2001. 50(10): p. 743-9. 2: Maes M et al. Effects of atypical antipsych . . . [PMID: 10706993] Related Articles, Links.

51. Minagar, A., et al., *The role of macrophage/microglia and astrocytes in the pathogenesis of three neurologic disorders: HIV-associated dementia, Alzheimer disease, and multiple sclerosis*. J Neurol Sci, 2002. 202(1-2): p. 13-23. 9: Jeohn G H et al. Go6976 protects mesencephalic . . . [PMID: 12076986] Related Articles, Links.

52. Gaser, C., et al., *Ventricular enlargement in schizophrenia related to volume reduction of the thalamus, striatum, and superior temporal cortex*. Am J Psychiatry., 2004. 161: p. 154-156.

53. Kurtzke, J., *Disability rating scales in multiple sclerosis*. Ann N Y Acad. Sci., 1984. 436: p. 347-60.

54. Karlsson, H., et al. *HERV-W-related RNA detected in plasma from individuals with recent-onset schizophrenia or schizoaffective disorder*. Mol Psychiatry, 2004. 9: P. 12-13.

55. Qiu, Z. and D. L. Gruol, *Interleukin-6, beta-aymloid peptide and NMDA interactions in rat cortical neurons*. J Neuroimmunol, 2003. 139(1-2): p. 51-7. 2: Jenner P. Oxidative stress in Parkinson . . . [PMID: 12666096] Related Articles, Links.

56. Lafon, M., et al., *Human Viral superantigens: to be or not to be transactivated?* Trends in Immnunology, 2002. 23(5): p. 238-239.

57. Pranzatelli, M., *Innovations in drug delivery to the central nervous system*. Drugs Today (Barc). 1999. 35: p. 435-448.

58. Merlo, A., J. Mueller-Brand, and H. Maecke, *Comparing monoclonal antibodies and small peptidic hormones for local targeting of malignant gliomas*. Acta Neurochir., 2003. 88: p. 83-91.

59. Antony, J., et al., *Human endogenous retrovirus glycoprotein-mediated induction of redox reactants causes oligodendrocyte death and demyelination*. Nat. Neurosci., 2004. 7(10): p. 1088-95.

60. Ng, P. and Y. Osawa, *Preparation and characterization of the F(ab)2 fragments of an aromatase activity-suppressing monoclonal antibody*. Steroids., 1997. 62: p. 776-81.

61. Perron, H., et al., *In vitro transmission and antigenicity of a retrovirus isolated from a multiple sclerosis patient*. Res Virol, 1992. 143(5): p. 337-50.

62. Serra, C., et al., *Multiple sclerosis and multiple sclerosis-associated retrovirus in Sardinia*. Neurol Sci, 2001. 22(2): p. 171-3.

63. Zawada M Fau-Liwien, I., et al., *MSRV pol sequence copy number as a potential marker of multiple sclerosis*. Pol J Pharmacol, 2003. 55(5): p. 869-75.

64. Perron H Fau-Garson, J. A., et al., *Molecular identification of a novel retrovirus repeatedly isolated from*. Proc Natl Acad Sci USA, 1997. 94(14): p. 7583-8.

65. Rolland, A., et al., *Correlation between disease severity and in vitro cytokine production mediated by MSRV(Multiple Sclerosis Associated Retroviral Element) envelope protein in patients with multiple sclerosis*. J Neuroimmunol, 2004. In press (Published Online Dec. 2004.).

66. Komurian-Pradel, P., et al., *Molecular cloning and characterization of MSRV-related sequences associated with retrovirus-like particles*. Virology, 1999. 260(1): p. 1-9.

67. Perron, H., et al., *Human Endogenous Retrovirus (HERV)-W Env And Gag Proteins: Physiological Expression In Human Brain And Pathophysiological Modulation In Multiple Sclerosis Lesions*. J. Neurovirology, 2005. In press.

---

The invention claimed is:

1. A composition comprising:
   at least one selected from the group consisting of:
   anti-multiple sclerosis-associated retrovirus/human endogenous retrovirus-W envelope protein soluble fraction antibodies (anti-MSRV/HERV-W Env-SU antibodies), and
   mixtures of anti-MSRV/HERV-W Env-SU antibodies and anti-toll-like receptor 4 antibodies (anti-TLR4 antibodies) capable of binding specifically to the TLR4 receptor for the soluble fraction of the multiple sclerosis-associated retrovirus/human endogenous retrovirus-W envelope protein (MSRV/HERV-W Env protein), and
   a pharmaceutically acceptable carrier;
   wherein the soluble fraction of the MSRV/HERV-W Env protein comprises the sequence set forth in SEQ ID NO:3 and the antibody or mixture of antibodies inhibits an interaction between the soluble fraction of the MSRV/HERV-W Env protein and the TLR4 receptor.

2. The composition of claim 1, further comprising a pharmaceutically acceptable vector.

3. The composition of claim 1, wherein the composition comprises the mixture of at least one anti-MSRV/HERV-W Env-SU antibody and at least one anti-TLR4 antibody.

4. A method of treating multiple sclerosis, the method comprising administering to an individual having multiple sclerosis the composition of claim 1.

5. A method of inhibiting an interaction between a soluble fraction of a multiple sclerosis-associated retrovirus/human endogenous retrovirus-W envelope protein (MSRV/HERV-W Env protein) and a toll-like receptor 4 (TLR4) for the soluble fraction, the method comprising:

administering to an individual in need thereof a composition comprising:
   at least one selected from the group consisting of:
   anti-multiple sclerosis-associated retrovirus/human endogenous retrovirus-W envelope protein soluble fraction antibodies (anti-MSRV/HERV-W Env-SU antibodies), and
   mixtures of anti-MSRV/HERV-W Env-SU antibodies and anti-toll-like receptor 4 antibodies (anti-TLR4 antibodies) capable of binding specifically to the TLR4 receptor, and
   a pharmaceutical carrier;
   wherein the soluble fraction of the MSRV/HERV-W Env protein comprises the sequence set forth in SEQ ID NO:1.

6. The method of claim 5, wherein the composition comprises the mixture of at least one anti-MSRV/HERV-W Env-SU antibody and at least one anti-TLR4 antibody.

7. An antibody capable of specifically binding to a region selected from the group consisting of:
   amino acid residues 122-131 of SEQ ID NO:3;
   amino acid residues 312-316 of SEQ ID NO:3; and
   amino acid residues 181-186 of SEQ ID NO:3.

8. The antibody according to claim 7, wherein the antibody is produced by a culture of hybridomas from mice cells after immunization with a soluble fraction of a multiple sclerosis-associated retrovirus/human endogenous retrovirus-W envelope protein (MSRV/HERV-W Env protein), wherein soluble fraction comprises the sequence set forth in SEQ ID NOs: 1 or 3.

* * * * *